(12) United States Patent
Booth

(10) Patent No.: US 11,021,435 B2
(45) Date of Patent: Jun. 1, 2021

(54) SEROTONIN RECEPTOR-TARGETING COMPOUNDS AND METHODS

(71) Applicant: Northeastern University, Boston, MA (US)

(72) Inventor: Raymond G. Booth, Arlington, MA (US)

(73) Assignee: Northeastern University, Boston, MA (US)

( * ) Notice: Subject to any disclaimer, the term of this patent is extended or adjusted under 35 U.S.C. 154(b) by 694 days.

(21) Appl. No.: 15/311,905

(22) PCT Filed: May 19, 2015

(86) PCT No.: PCT/US2015/031523
§ 371 (c)(1),
(2) Date: Nov. 17, 2016

(87) PCT Pub. No.: WO2015/179366
PCT Pub. Date: Nov. 26, 2015

(65) Prior Publication Data
US 2017/0081273 A1    Mar. 23, 2017

Related U.S. Application Data

(60) Provisional application No. 62/000,286, filed on May 19, 2014.

(51) Int. Cl.
| | |
|---|---|
| *C07C 211/42* | (2006.01) |
| *C07C 217/74* | (2006.01) |
| *C07C 215/64* | (2006.01) |
| *A61K 31/135* | (2006.01) |
| *C07D 217/04* | (2006.01) |
| *C07D 307/52* | (2006.01) |

(52) U.S. Cl.
CPC .......... *C07C 211/42* (2013.01); *A61K 31/135* (2013.01); *C07C 215/64* (2013.01); *C07C 217/74* (2013.01); *C07D 217/04* (2013.01); *C07D 307/52* (2013.01); *C07C 2601/08* (2017.05); *C07C 2602/10* (2017.05)

(58) Field of Classification Search
None
See application file for complete search history.

(56) References Cited

U.S. PATENT DOCUMENTS

| | | |
|---|---|---|
| 8,236,845 B2 | 8/2012 | Garcia-Lopez et al. |
| 2010/0227934 A1 | 9/2010 | Booth |
| 2012/0149693 A1 | 6/2012 | Booth |
| 2014/0155490 A1 | 6/2014 | Booth |

FOREIGN PATENT DOCUMENTS

| | | |
|---|---|---|
| WO | 96/34849 A1 | 11/1996 |
| WO | 2008/095689 A1 | 8/2008 |
| WO | 2008/116663 A2 | 10/2008 |
| WO | 2008/154044 A1 | 12/2008 |
| WO | 2008156707 | 12/2008 |
| WO | 2009/061436 A1 | 5/2009 |
| WO | 2010129048 | 5/2010 |

OTHER PUBLICATIONS

Holmberg, P. et al., J. Med. Chem. (2004), vol. 47, pp. 3927-3930.*
Vermeulen, E. et al., J. Med. Chem. 2003 vol. 46, pp. 5365-5374.*
Carey, F. "Organic Chemistry," New York McGraw-Hill 2000, excerpt p. 266.*
Silverman, R. "The Organic Chemistry of Drug Design and Drug Action," 2004, NY Elsevier, pp. 29-32.*
Ghoneim O et al. Novel ligands for the human histamine H1 receptor: Synthesis, pharmacology, and comparative molecular field analysis studies of 2-dimethylamino-5-(6)-phenyl-1,2,3,4-tetrahydronaphthalenes. Bioorg & Med. Chem., 14 (2006):6640-6658. Abstract.
PubChem, Compound Summary for SID 75012495, Create Date: Jun. 11, 2009. [retrieved on Sep. 22, 2015]. Retrieved from the Internet <URL: pubchem.ncbi.nlm.nih.gov/substance/75012495>.
PubChem, Compound Summary for SID 104161862, Create Date: Jan. 21, 2011. [retrieved on Sep. 22, 2015]. Retrieved from the Internet <URL: pubchem.ncbi.nlm.nih.gov/substance/104161862>.
Holmberg P et al. Novel 2-Aminotetralin and 3-AminoChroman Derivatives as Selective Serotonin 5-HT7 Receptor Agonists and Antagonists. J. Med. Chem., 2004, 47 (16): 3927-3930. Abstract.
Lepailleur A et al. Molecular Modeling Studies Focused on 5-HT~ versus 5-HT1A Selectivity. Discovery of Novel Phenylpyrrole Derivatives with High Affinity for 5-HT7 Receptors. J. Chem. Inf. Model. 2005, 45, 1075-1081.
Vermeulen, E.S. et al., "Characterization of the 5-HT7 Receptor. Determination of the Pharmacophore for 5-HT7 Receptor Agonism and CoMFA-Based Modeling of the Agonist Binding Site", Journal of Medicinal Chemistry, 2003, 46, 5365-5374.
E. Badarau, et al., "SAR studies on new bis-aryls 5-HT7 ligands: Synthesis and molecular modeling", Bioorganic & Medicinal Chemistry, Mar. 1, 2010, vol. 18, No. 5, pp. 1958-1967.
Guscott, M. et al., "Genetic knockout and pharmacological blockade studies of the 5-HT7 receptor suggest therapeutic potential in depression", Neuropharmacology, (2005), vol. 48, pp. 492-502.

* cited by examiner

*Primary Examiner* — Heidi Reese
(74) *Attorney, Agent, or Firm* — Verrill Dana, LLP

(57) ABSTRACT

This invention relates to, in part, compositions and methods that are useful for, inter alia, the treatment of various diseases, including those linked to binding at a serotonin receptor. The compositions include chiral tetrahydronaphthalen-2-amine derivatives. Accordingly, the present invention provides for compositions and methods that agonize or antagonize one or more serotonin receptors and which find use in the treatment of various neuropsychiatric diseases or disorders including, without limitation, autism spectrum disorder (ASD) or associated symptoms.

19 Claims, 11 Drawing Sheets

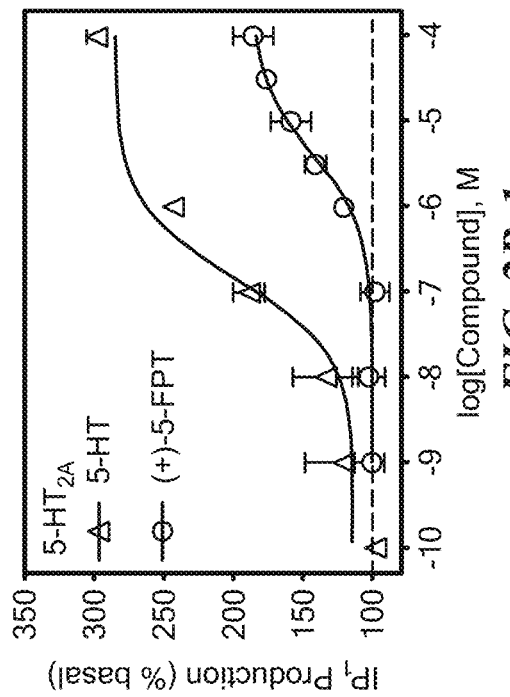
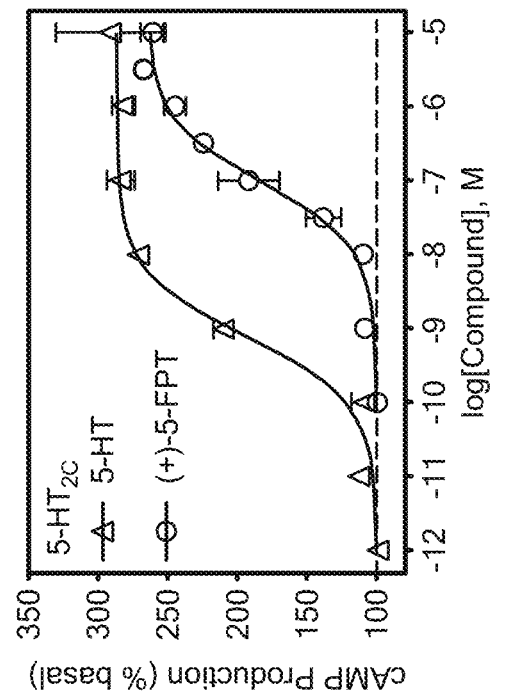
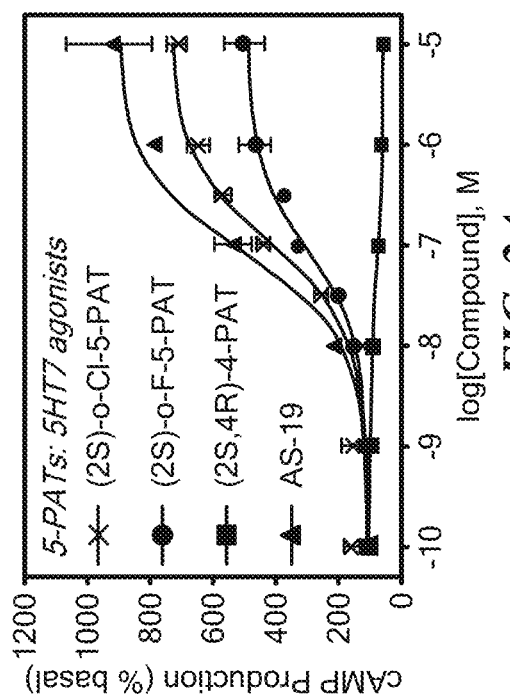
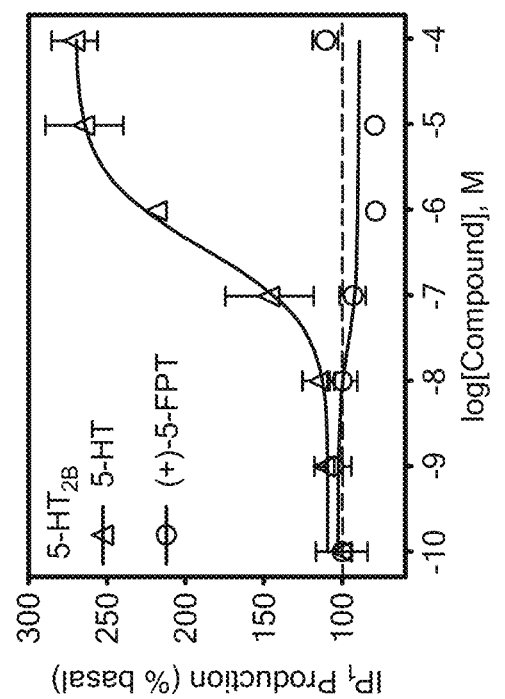
FIG. 2A
FIG. 2B-1
FIG. 2B-2
FIG. 2B-3

Fig. 12

| Receptor | 5-HT$_7$ | | | 5-HT$_{1A}$ | | | 5-HT$_{2A}$ | | |
|---|---|---|---|---|---|---|---|---|---|
| Compound | Avg (nM) | Std Dev | SEM | Avg (nM) | Std Dev | SEM | Avg (nM) | Std Dev | SEM |
| - 5PAT | 9.5 | 1.2 | 0.4 | 7.3 | 1.5 | 0.7 | 556.0 | 86.4 | 49.9 |
| + 5PAT | 4371.0 | 1861.1 | 930.5 | 813.0 | 234.8 | 166.0 | 753.3 | 46.0 | 26.6 |
| - 5PAT oF | 460.3 | 105.4 | 52.7 | 1035.0 | 302.7 | 174.8 | 134.5 | 44.3 | 18.1 |
| + 5PAT oF | 6.2 | 1.8 | 0.7 | 21.8 | 5.7 | 2.5 | 885.7 | 157.3 | 64.2 |
| - 5PAT oCl | 57.8 | 26.2 | 11.7 | 225.8 | 23.9 | 10.7 | 3874.3 | 868.1 | 434.0 |
| + 5PAT oCl | 5.8 | 1.5 | 0.6 | 36.0 | 10.2 | 4.6 | 490.0 | 172.1 | 70.3 |
| - 5PAT di mCF3 | 912.0 | 519.5 | 299.9 | 2298.7 | 746.0 | 430.7 | >10,000 | | |
| +5PAT di mCF3 | >10,000 | | | | | | >10,000 | | |
| ± 5PAT di mCl | 401.3 | 109.5 | 54.8 | 2222.3 | 948.9 | 474.5 | 1239.7 | 228.4 | 161.5 |
| ± 5PAT mF | 33.7 | 10.7 | 6.2 | 23.0 | 7.0 | 4.0 | 772.0 | 56.6 | 40.0 |
| ± 5PAT pF | 117.8 | 37.5 | 16.8 | 30.3 | 11.9 | 6.9 | 939.3 | 239.2 | 169.1 |
| ± 5PAT CH3-O benzyl | | | | 2660.7 | 608.3 | 351.2 | 431.0 | 87.2 | 61.7 |
| ± 5PAT anthracene | 447.0 | 223.3 | 111.7 | 1338.7 | 657.9 | 379.8 | 928.3 | 347.5 | 200.6 |
| ± 5PAT di mF | 176.4 | 71.2 | 31.8 | 230.7 | 27.2 | 15.7 | 1018.5 | 78.8 | 39.4 |
| + - 7', 8' OME 5PAT | | | | | | | 120.5 | 29.8 | 14.9 |
| + - cyclopentyl 5PAT | 236.7 | 60.5 | 34.9 | 98.0 | 13.1 | 7.6 | 807.7 | 241.3 | 120.6 |
| +- 2' Furanyl 5PAT | 123.7 | 4.7 | 2.7 | 172.0 | | | 1369.0 | 283.2 | 141.6 |
| +- napthalene 5PAT | 22.0 | 3.5 | 2.0 | 169.5 | 88.4 | 62.5 | 1854.0 | 297.0 | 148.5 |
| - napthalene 5PAT | 18.6 | 4.4 | 2.0 | 57.3 | 21.9 | 12.7 | | | |
| + napthalene 5PAT | 31.2 | 10.2 | 4.6 | 171.0 | 77.2 | 44.6 | | | |
| +- isoquinoline 5PAT | 97.3 | 18.2 | 10.5 | 542.0 | | | | | |
| +- oNH3 5PAT | | | | 382.0 | | | | | |
| ± AT | 275.8 | 50.00 | 25.00 | | | | 2270.8 | 636.88 | 318.44 |
| ± 5 PAT | 9.6 | 4.39 | 2.53 | 20.0 | 5.00 | 2.50 | 356.0 | 144.12 | 72.06 |
| ± 5 PAT mCF3 | 62.7 | 11.37 | 6.57 | 215.0 | | | 120.0 | 20.35 | 10.17 |
| ± 5 PAT mOMe | 37.0 | 15.72 | 9.07 | 72.7 | 21.22 | 10.61 | 479.3 | 150.59 | 86.94 |
| ± 5 PAT mCl | 18.3 | 4.16 | 2.40 | 101.0 | | | 139.8 | 61.33 | 30.66 |

Fig. 12 (cont.)

| Receptor | 5-HT$_{2B}$ | | | 5-HT$_{2C}$ | | | H1 | | |
|---|---|---|---|---|---|---|---|---|---|
| Compound | Avg (nM) | Std Dev | SEM | Avg (nM) | Std Dev | SEM | Avg (nM) | Std Dev | SEM |
| - 5PAT | 65.5 | 12.0 | 8.5 | 546.5 | 40.3 | 28.5 | 861.2 | 746.6 | 527.9 |
| + 5PAT | 26.5 | 3.5 | 2.5 | 200.7 | 12.1 | 7.0 | 1180.0 | 1017.1 | 719.2 |
| - 5PAT oF | 684.3 | 262.9 | 131.4 | 2856.4 | 1551.4 | 633.3 | 1997.8 | 1189.9 | 841.4 |
| + 5PAT oF | 61.8 | 18.0 | 7.4 | 267.0 | 36.8 | 16.5 | 1223.5 | 751.5 | 375.8 |
| - 5PAT oCl | | | | 1441.0 | 504.1 | 291.0 | 1020.0 | 1030.9 | 729.0 |
| + 5PAT oCl | 11.0 | 1.4 | 1.0 | 104.7 | 16.5 | 9.5 | 519.5 | 315.3 | 157.7 |
| - 5PAT di mCF3 | | | | 3867.0 | | | | | |
| +5PAT di mCF3 | | | | 603.5 | 193.0 | 111.5 | 3220.7 | 4397.2 | 3109.3 |
| ± 5PAT di mCl | 95.5 | 10.6 | 6.1 | 272.0 | 19.0 | 11.0 | 1094.7 | 970.8 | 686.5 |
| ± 5PAT mF | 96.0 | 21.2 | 12.2 | 253.0 | 120.1 | 69.3 | 428.1 | 313.9 | 221.9 |
| ± 5PAT pF | 313.0 | 83.4 | 48.2 | 849.3 | 252.0 | 145.5 | 870.8 | 628.2 | 444.2 |
| ± 5PAT CH3-O benzyl | 89.5 | 33.2 | 19.2 | 617.0 | 50.1 | 28.9 | 77.6 | 42.3 | 29.9 |
| ± 5PAT anthracene | 53.0 | 17.0 | 9.8 | 125.7 | 45.5 | 26.3 | 424.1 | 345.8 | 244.5 |
| ± 5PAT di mF | 110.0 | 14.1 | 8.2 | 446.0 | 29.7 | 17.2 | 332.6 | 446.1 | 315.4 |
| + - 7', 8' OME 5PAT | | | | 2688.0 | | | | | |
| + - cyclopentyl 5PAT | | | | 187.5 | 50.2 | 35.5 | 94.8 | 83.8 | 59.3 |
| +- 2' Furanyl 5PAT | | | | 230.0 | 22.6 | 16.0 | 16.0 | | |
| +- napthalene 5PAT | | | | 255.0 | 32.5 | 23.0 | 23.0 | | |
| - napthalene 5PAT | | | | 348.5 | 82.7 | 58.5 | | | |
| + napthalene 5PAT | | | | 177.0 | 67.9 | 48.0 | | | |
| +- isoquinoline 5PAT | | | | 1419.5 | 167.6 | 118.5 | | | |
| +- oNH3 5PAT | | | | | | | | | |
| ± AT | 342.3 | 207.50 | 119.80 | 1299.75 | 404.10 | 202.05 | 1011.76 | 594.38 | 420.29 |
| ± 5 PAT | 28.8 | 8.42 | 4.21 | 83.00 | 2.65 | 1.53 | 762.91 | 448.65 | 317.24 |
| ± 5 PAT mCF3 | 34.0 | 17.83 | 8.92 | 58.25 | 16.15 | 8.08 | 1088.27 | 720.20 | 509.26 |
| ± 5 PAT mOMe | 14.0 | 3.00 | 1.50 | 70.67 | 12.34 | 7.13 | 956.78 | 653.54 | 462.12 |
| ± 5 PAT mCl | 16.8 | 0.96 | 0.55 | 32.25 | 6.85 | 3.42 | 585.08 | 385.60 | 272.66 |

SEROTONIN RECEPTOR-TARGETING COMPOUNDS AND METHODS

RELATED APPLICATIONS

This application claims the benefit of U.S. Provisional Patent Application No. 62/000,286, filed May 19, 2014, the contents of which are hereby incorporated by reference in their entirety.

STATEMENT REGARDING FEDERALLY SPONSORED RESEARCH OR DEVELOPMENT

This invention was made with government support under Grant Numbers DA023928, DA030989, and MH081193 awarded by the National Institutes of Health. The government has certain rights in the invention.

FIELD OF THE INVENTION

This invention relates to, in part, compositions and methods that are useful for the treatment of various diseases, including those linked to serotonin receptor binding, including, for example, neuropsychiatric diseases or disorders.

BACKGROUND

Many converging lines of evidence point to a prominent direct or modulatory role for the serotonin (5-hydroxytryptamine, 5-HT) system in a variety of neuropsychiatric diseases or disorders. For example, blood 5-HT levels and 5-HT transporter genotype correlate with the presence of stereotypy, an uncontrolled, rigid and repetitive, low-order, motor behavior (e.g. hand waving and body rocking) that is considered a robust diagnostic marker of autism spectrum disorder (ASD) in children. Further, diet-induced reduction of 5-HT (e.g. via depletion of its precursor amino acid tryptophan) in persons with ASD increases stereotypy.

In some clinical trials for ASD, selective serotonin reuptake inhibitors (SSRIs) showed positive effects on stereotypy and compulsions. The effects of SSRIs, however, were mixed and, in some cases, SSRIs worsened stereotypy. Side-effects from SSRI treatment are also highly prevalent, potentially as a result of the shotgun approach, i.e. non-discriminant elevation of 5-HT levels that could have non-therapeutic interactions at multiple 5-HT receptors.

There remains a need for agents that can modulate serotonin receptors (5-hydroxytryptamine receptors or 5-HT receptors) for the treatment of neuropsychiatric diseases or disorders, for instance, via targeting specific 5-HT receptors.

SUMMARY OF THE INVENTION

Accordingly, the present invention provides for compositions and methods that agonize or antagonize one or more serotonin receptors and which find use in the treatment of various neuropsychiatric diseases or disorders including, without limitation, autism spectrum disorder (ASD) or associated symptoms.

In one aspect, the invention provides a compound, or pharmaceutical composition, comprising a therapeutically effective amount of a compound, having the structure of the Formula I':

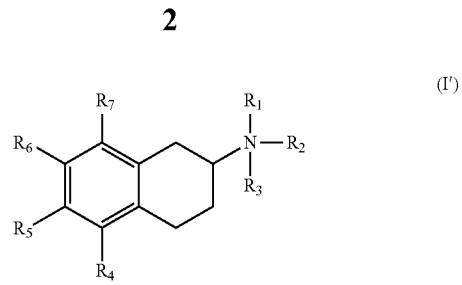

$R_1$ to $R_7$ are independently selected substituents. Suitable substituents are disclosed herein. For example, in some embodiments, one of $R_1$, $R_2$, and $R_3$ is hydrogen and two of $R_1$, $R_2$, and $R_3$ are alkyl or may come together to form a heterocyclic ring and each of $R_4$, $R_5$, $R_6$, and $R_7$ is independently hydrogen, hydroxy, sulfoxy, halo, acyl, acyloxy, alkyl, heteroalkyl, alkenyl, heteroalkenyl, alkynyl, heteroalkynyl, alkoxy, cycloalkyl, heterocycloalkyl, aryl, arylalkyl, arylhalo, arylhydroxy, arylcyano, aryltrifluoromethyl, aryltrifluoromethoxy, arylnitro, aryltrifluoromethoxy, arylnitro, and arylether, arylester, arylsulfonyl, arylsulfinyl, arylsulfonamidyl, arylsulfonate, arylsulfoxyl, arylphosphate ester, arylcarbonyl, arylcarboxylate, arylcarbamate, arylamine, arylimide, heteroaryl, heteroarylalkyl, heteroarylhalo, heteroarylhydroxy, heteroarylcyano, heteroaryltrifluoromethyl, aryltrifluoromethoxy, arylnitro, heteroaryltrifluoromethoxy, heteroarylnitro, and heteroarylether, heteroarylester, heteroarylsulfonyl, heteroarylsulfinyl, heteroarylsulfonamidyl, heteroarylsulfonate, heteroarylsulfoxyl, heteroarylphosphate ester, heteroarylcarbonyl, heteroarylcarboxylate, heteroarylcarbamate, heteroarylamine, heteroarylimide, quinidine, morpholine, and any ring structure is optionally substituted with any of the substituents described herein, with the proviso that any two adjacent substituents can come together to form a carbocydic or heterocyclic ring system.

In various embodiments, any of $R_4$, $R_5$, $R_6$, and $R_7$ is a hydrocarbon or heterocyclic ring system. In some embodiments, the hydrocarbon or heterocyclic ring system is independently selected from phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyazinyl, pyrimidinyl, oxadiazolyl, benzimidazolyl, and triazinyl, each of which may contain substituents (i.e. is optionally substituted). In some embodiments, the heterocyclic ring system may contain one or more heteroatoms selected from the group consisting of oxygen, sulfur, nitrogen, and combinations thereof.

In a specific embodiment, only $R_4$ is a hydrocarbon or heterocyclic ring system which is optionally substituted. In a specific embodiment, only $R_4$ is a hydrocarbon or heterocyclic ring system which is optionally substituted, one of $R_1$, $R_2$, and $R_3$ is hydrogen and two of $R_1$, $R_2$, and $R_3$ are alkyl, and each of $R_5$, $R_6$, and $R_7$ is independently hydrogen, hydroxy, sulfoxy, halo, acyloxy, alkyl, heteroalkyl, alkenyl, heteroalkenyl, alkynyl, heteroalkynyl, acyl, and alkoxy. In some embodiments, the compound of Formula I' is a substantially enantiomerically pure compound. In some embodiments, the compound of Formula I' modulates a serotonin 5-HT receptor. In some embodiments, the compound of Formula I' is a dual partial agonist at the serotonin 5-HT$_7$ and 5-HT$_{1A}$ receptors.

In one aspect, the invention provides a pharmaceutical composition, comprising a therapeutically effective amount of a substantially enantiomerically pure dual partial agonist at the serotonin 5-HT$_7$ and 5-HT$_{1A}$ receptors, the dual partial agonist having the structure of Formula (I):

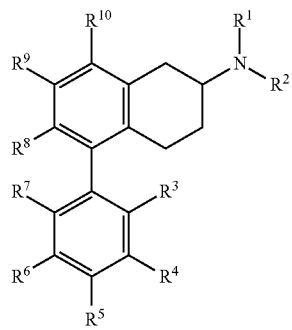

or pharmaceutically acceptable salt, hydrate, or solvate thereof, wherein each of R$^1$ to R$^{10}$ is hydrogen or an independently selected substituent. In some embodiments, each of R$^1$ and R$^2$ is independently hydrogen or alkyl, or R$^1$ and R$^2$ come together to form an optionally substituted heterocyclic ring; each of R$^3$, R$^4$, R$^5$, R$^6$, R$^7$, R$^8$, R$^9$, and R$^{10}$ is independently hydrogen, hydroxy, acyl, acyloxy, alkyl, heteroalkyl, alkenyl, heteroalkenyl, alkynyl, heteroalkynyl, alkoxycarbonyl, cyano, trifluoromethyl, trifluoromethoxy, nitro, amino, and amido, and wherein any two adjacent R groups may optionally come together to form a carbocyclic or heterocyclic ring system; and a pharmaceutically acceptable excipient or carrier. In some embodiments, the substituents are selected from hydrogen, halo, acyl, acyloxy, alkyl, heteroalkyl, alkenyl, heteroalkenyl, alkynyl, heteroalkynyl, alkoxy, alkoxycarbonyl, cycloalkyl, heterocycloalkyl, aryl, arylalkyl, heteroaryl, heteroarylalkyl, hydroxy, cyano, trifluoromethyl, trifluoromethoxy, nitro, and trimethylsilanyl, ether, ester, sulfide, disulfide, sulfonyl, sulfinyl, sulfonamidyl, sulfonate, sulfoxyl, phosphate ester, phosphine, borate ester, carbonyl, carboxylate, carbamate, amine, imide, and quinidine.

In some embodiments, the composition comprises at least about 70%, or at least about 80%, or at least about 85%, or at least about 90%, or at least about 95%, or at least about 97%, or at least about 99% of a single enantiomer. In various embodiments, a least about 85%, or at least about 90%, or at least about 95%, or at least about 97%, or at least about 99% of a single enantiomer. In some embodiments, the single enantiomer has functional properties (e.g. serotonin receptor selectivity and/or receptor affinity) that are not found in a corresponding enantiomer. Accordingly, in some embodiments, the invention does not contemplate racemates or racemic mixtures.

In some embodiments, the dual partial agonist selectively binds to serotonin 5-HT$_7$ receptor and/or serotonin HT$_{1A}$ receptor with a binding affinity (K$_i$) of less than about 100 nM, or less than about 50 nM, or less than about 25 nM, or less than about 20 nM, or less than about 10 nM, or less than about 5 nM, or less than about 2 nM, or less than about 1 nM. In some embodiments, the dual partial agonist provides stereoselective binding to one or more of the serotonin 5-HT$_7$ and 5-HT$_{1A}$ receptors, for instance providing at least about 10-fold, or at least about 20-fold, or at least about 30-fold, or at least about 40-fold, or at least about 50-fold, or at least about 75-fold, or at least about 100-fold higher affinity than one or more of the serotonin 5-HT$_{2A}$ and 5-HT$_{2C}$ receptors. Further, in some embodiments, the dual partial agonist does not bind one or more of the histamine H1 receptor, dopamine D2, and adrenergic $\alpha_{1A}$ and $\alpha_{1B}$ receptors at physiologically-relevant levels. As described herein, the receptor binding (agonist) profile of compounds of the invention provide unique potential for treatment of symptoms, such as by way of non-limitation, stereotypy.

In various embodiments, the therapeutically effective amount of the composition is less than about 100 mg, or less than about 90 mg, or less than about 80 mg, or less than about 70 mg, or less than about 60 mg, or less than about 50 mg, or less than about 40 mg, or less than about 30 mg, or less than about 25 mg, or less than about 20 mg, or less than about 15 mg. As described herein with respect to mouse models, in certain embodiments compounds of the invention are quickly removed from the periphery but will accumulate in the brain. Together with the relatively low affinity of these compound for the 5-HT$_7$ and 5-HT$_{1A}$ receptors, the compounds will provide therapeutic efficacy at relatively low dosages.

In various embodiments, the pharmaceutical compositions of the invention are formulated for long-action or sustained-release. In some embodiments, the formulation is suitable for oral delivery and/or transmucosal delivery (e.g. a capsule, tablet, patch, or lozenge).

In various embodiments, the dual partial agonist accumulates in the brain and a formulation of such delivers a physiological amount of dual partial agonist to the human brain for at least about 6 hours, or at least about 9 hours, or at least about 12 hours, or at least about 15 hours, or at least about 18 hours, or at least about 21 hours, or at least about 24 hours.

In some aspects, the present invention provides a method of selectively modulating serotonin 5-HT$_7$ and 5-HT$_{1A}$ receptors by contacting a cell with a compound or composition described herein, wherein the modulation is partial antagonism. In some aspects, the present invention provides a method of treating or preventing a neuropsychiatric disease or disorder including, by way of non-limiting example, autism, anxiety, depression, obsessive-compulsive disorders, schizophrenia, suicide, migraine, emesis, alcoholism and neurodegenerative disorders, by administering an effective amount of a compound or composition described herein. In various embodiments, the present methods pertain to autism spectrum disorder (ASD); Asperger syndrome, Fragile X syndrome (FXS), Prader-Willi syndrome, Rett syndrome, Tourette syndrome, attention-deficit hyperactivity disorder (ADHD), obsessive-compulsive disorder, psychotic disorders, psychostimulant addiction and generalized anxiety.

In some aspects, the present invention provides a method of treating autism spectrum disorder (ASD), comprising administering an effective amount of a compound or composition described herein to a patient in need thereof.

In some aspects, the present invention provides a method of treating stereotypy, comprising administering an effective amount of a compound or composition described herein to a patient in need thereof.

BRIEF DESCRIPTION OF THE FIGURES

FIG. 2A shows 5-HT$_7$ partial agonist effects of (+)-o-F-PAT (second curve from the bottom), relative to AS-19 (the positive control, a potent agonist at the 5-HT7 receptor, top curve) as well as (+)-o-Cl-PAT (second curve from the top). The bottom curve is a 4-PAT compound negative control. Representative functional assay results show the mean±SEM of the concentration data points. FIG. 2B shows binding affinity of (+)-o-F-PAT at 5-HT$_{2A}$ (FIG. 2B-1), 5-HT$_{2B}$ (FIG. 2B-2), and 5-HT$_{2C}$ (FIG. 2b-3) receptors.

FIG. 12 shows various synthesized 5-PAT compounds and their affinities at serotonin receptor types, 5-HT$_{1A}$, 5-HT$_{2A}$, 5-HT$_{2B}$, 5-HT$_{2C}$, and 5-HT$_7$. Also included are affinities at histamine H1 receptor.

DETAILED DESCRIPTION OF THE INVENTION

Figure 1A:
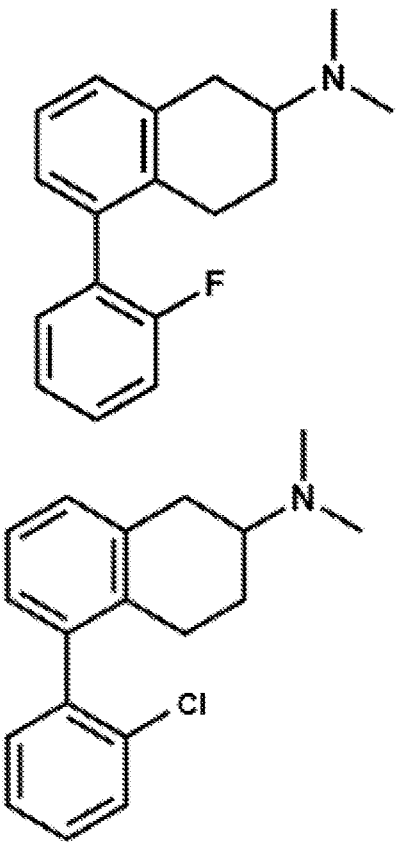
FIG. 1A shows 5-FPT. Racemic 5-FPT (a.k.a. o-F-PAT) was resolved into (+) and (−) optical enantiomers. Also in FIG. 1A, Racemic 5-CIPT (a.k.a. o-Cl-5-PAT), was also resolved into (+) and (−) optical enantiomers.

The present invention is based, in part, on the discovery of novel compounds that steroselectively modulate specific serotonin receptors and, in turn, are useful in treating stereotypy and disorders that are characterized by these symptoms. Related compounds were reported to not warrant chiral resolution in light of poor (H1) receptor binding properties (see, e.g. Ghoneim, Bioorg & Med. Chem., 14 (2006): 6640, the contents of which are hereby incorporated by reference in their entirety).

In some aspects, the invention provides a compound, or a pharmaceutical composition, comprising a compound, having the structure of Formula I':

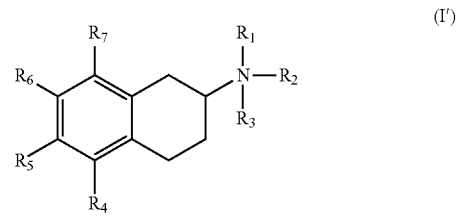

where at least one of R$_1$, R$_2$, R$_3$, R$_4$, R$_5$, R$_6$, and R$_7$ are defined as above.

In various embodiments, any of R$_4$, R$_5$, R$_6$, and R$_7$ is a hydrocarbon or heterocyclic ring system. In some embodiments, the hydrocarbon or heterocyclic ring system is independently selected from phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, oxadiazolyl, benzimidazolyl, and triazinyl, each of which may contain substituents (i.e. is optionally substituted). In some embodiments, the heterocyclic ring system may contain one or more heteroatoms selected from the group consisting of oxygen, sulfur, nitrogen, and combinations thereof.

In a specific embodiment, only R$_4$ is a hydrocarbon or heterocyclic ring system which is optionally substituted. In a specific embodiment, only R$_4$ is a hydrocarbon or heterocyclic ring system which is optionally substituted, one of R$_1$, R$_2$, and R$_3$ is hydrogen and two of R$_1$, R$_2$, and R$_3$ are alkyl, and each of R$_5$, R$_6$, and R$_7$ is independently hydrogen, hydroxy, sulfoxy, halo, acyloxy, alkyl, heteroalkyl, alkenyl, heteroalkenyl, alkynyl, heteroalkynyl, acyl, and alkoxy. In these embodiments, the total number of atoms that comprise R$_4$ may be at least about 5, and not more than about 20 atoms, not including hydrogen atoms (e.g. between about 5 to about 10 non-hydrogen atoms, or between about 5 to about 15 non-hydrogen atoms, or between about 10 to about 15 non-hydrogen atoms).

In some embodiments, the compound of Formula I' is a substantially enantiomerically pure compound.

In some embodiments, the compound of Formula I' is a dual partial agonist at the serotonin 5-HT$_7$ and 5-HT$_{1A}$ receptors.

In some aspects, the invention provides a pharmaceutical composition, comprising a therapeutically effective amount of a substantially enantiomerically pure dual partial agonist at the serotonin 5-HT$_7$ and 5-HT$_{1A}$ receptors, the dual partial agonist having the structure of Formula (I):

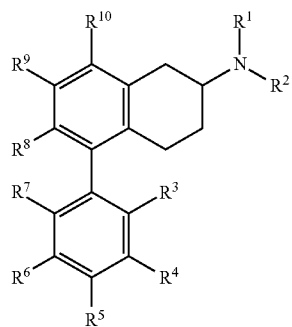

(I)

or pharmaceutically acceptable salt thereof, where each of $R^1$, $R^2$, $R^3$, $R^4$, $R^5$, $R^6$, $R^7$, $R^8$, $R^9$, and $R^{10}$ is hydrogen or a substituent, for example, as defined above.

In some embodiments, each of $R^1$, $R^2$, $R^3$, $R^4$, $R^5$, $R^6$, $R^7$, $R^8$, $R^9$, and $R^{10}$ is independently hydrogen, alkyl, aryl, halo, nitro, amino, heteroaryl, cycloalkyl, heterocyclic, or alkoxy In some embodiments, both $R^1$ and $R^2$ are methyl.

In some embodiments, at least one of $R^3$, $R^4$, $R^5$, $R^6$, and $R^7$ is not hydrogen. In some embodiments, at least one of $R^3$, $R^4$, $R^5$, $R^6$, and $R^7$ is halo. In some embodiments, two of $R^3$, $R^4$, $R^5$, $R^6$, and $R^7$ are halo. In some embodiments, one of $R^3$, $R^4$, $R^5$, $R^6$, and $R^7$ is halo. In some embodiments, the halo is fluoro and is present at one or more of the ortho, para, or meta positions (or, in the case of a naphthyl ring, the halo substitution may be in the 2, 3, 4, 5, 6, or 7 position of the naphthyl ring (where the attachment position to the compounds's core is at position 1 or 8 of the naphthyl ring)). In some embodiments, at least one of $R^3$, $R^4$, $R^5$, $R^6$, and $R^7$ is fluoro. In some embodiments, only $R^3$ is a substituent other than H. In some embodiments, $R^3$ is halo. In some embodiments, $R^3$ is fluoro or chloro.

in some embodiments, ortho substituted compounds (e.g. halo) are better dual partial agonists, e.g. at the serotonin 5-HT$_7$ and 5-HT$_{1a}$ receptors than meta substituted compounds (e.g. halo).

In some embodiments, any one of $R^6$ and $R^7$, $R^5$ and $R^6$, $R^4$ and $R^5$, and $R^3$ and $R^4$ form a phenyl ring, which is substituted or unsubstituted. In various embodiments, if a naphthyl ring results, there is substitution with a halo, optionally selected from fluoro and chloro and optionally at one or more of the 2, 3, 4, 5, 6, or 7 position of the naphthyl ring (where the attachment position to the compounds's core is at position 1 or 8 of the naphthyl ring).

In various embodiments, the phenyl or naphthyl ring is unsubstituted.

In various embodiments, there is an optionally substituted hydrocarbon or heterocyclic ring system, e.g. a phenyl ring or naphthyl ring connected to the 5 position of the bicyclic core of Formula I (the core being the top of the structure, i.e. the tetrahydronaphthyl moiety bearing substituents $R^8$, —$R^{10}$ and the amino group being substituents $R^1$ and $R^2$). In some embodiments, these phenyl or naphthyl rings are substituted with a halo, optionally selected from fluoro and chloro. In some embodiments, the halo substitution is in the ortho, meta, or para position of the phenyl ring or the 2, 3, 4, 5, 6, or 7 position of the naphthyl ring. In some embodiments, the halo substitution is in the ortho of the phenyl ring or the 2 or 7 position of the naphthyl ring (where the attachment position to the compounds's core is at position 1 or 8 of the naphthyl ring).

In various embodiments, the total number of atoms that comprise substituents $R^3$ to $R^7$ are at least about 5, and not more than about 20 atoms, not including hydrogen atoms (e.g. between about 5 to about 10 non-hydrogen atoms, or between about 5 to about 15 non-hydrogen atoms, or between about 10 to about 15 non-hydrogen atoms). In some embodiments, the composition is not a substrate (at physiological levels) for one or more forms of P450. For instance, without wishing to be bound by theory, larger numbers of non-hydrogen atoms that comprise substituents $R^3$ to $R^7$ may prevent metabolism associated with P450 (such metabolism may be, without wishing to be bound by theory, oxidation-mediated). For example, in some embodiments, the composition is not a substrate (at physiological levels) for one or more families of P450 (e.g. CYP1, CYP2, CYP3, CYP4, CYP5, CYP7, CYP8, CYP11, CYP17, CYP19, CYP20, CYP21, CYP24, CYP26, CYP27, CYP39, CYP46, and CYP51). In some embodiments, the composition is not a substrate for one or more of CYP1A2, CYP2C19, CYP2C9, CYP2D6, CYP2E1, and CYP3A4. In these embodiments, the compound is suited for avoiding P450-mediated reduction in a pharmacological effect.

In some embodiments, one of $R^8$, $R^9$, and $R^{10}$ is methoxy. In some embodiments, $R^8$ and $R^9$ or $R^9$ and $R^{10}$ form a phenyl ring, which is substituted or unsubstituted.

In some embodiments, the dual partial agonist is

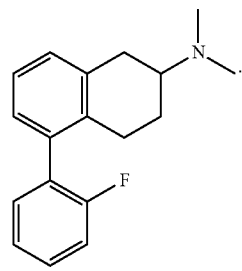 [SMILES: CN(C)C1CCc2c(cccc2-c2ccccc2F)C1]

In some embodiments, the dual partial agonist is the (+) enantiomer of the above compound.

In some embodiments, the dual partial agonist is:

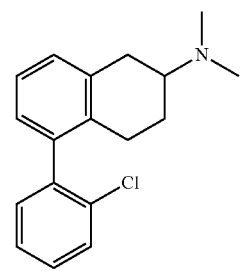 [SMILES: CN(C)C1CCc2c(cccc2-c2ccccc2Cl)C1]

In some embodiments the above compound is the (+) enantiomer of the above compound.

In some embodiments, the dual partial agonist is

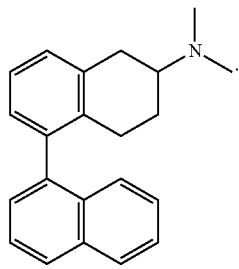 [SMILES: CN(C)C1CCc2c(cccc2-c2cccc3ccccc23)C1]

In some embodiments, the dual partial agonist is the (−) enantiomer of the above compound.

In various embodiments, the compositions of the present invention comprise at least about 70%, or at least about 80%, or at least about 85%, or at least about 90%, or at least about 95%, or at least about 97%, or at least about 99% of a single enantiomer. In various embodiments, a least about 85%, or at least about 90%, or at least about 95%, or at least about 97%, or at least about 99% of a single enantiomer. However, in certain embodiments, such as with ortho substituents (e.g., fluoro or chloro), racemates may be employed in connection with the invention.

In some embodiments, the compositions of the present invention comprises less than about 30%, or less than about 20%, or less than about 15%, or less than about 10%, or less than about 5%, or less than about 3%, or less than about 1% of a single enantiomer.

In some embodiments, the present compounds and compositions are substantially in the form of a single enantiomer and essentially free of the corresponding enantiomer.

In some embodiments, a single enantiomer has functional properties (e.g. serotonin receptor selectivity) that are not found in a corresponding enantiomer. For example, in some embodiments, the (+) enantiomer has serotonin-receptor modulating properties that are not found in the corresponding (−) enantiomer (e.g. the (−) enantiomer does not bind one of more serotonin receptors at physiological levels). By way of further example, in some embodiments, the (−) enantiomer has serotonin-receptor modulating properties that are not found in the corresponding (+) enantiomer (e.g. the (+) enantiomer does not bind one of more serotonin receptors at physiological levels). Such a stereoselectivity, in some embodiments, also applies to (R)- and (S)- and d- and l-. Accordingly, in some embodiments, the invention does not contemplate racemates or racemic mixtures. In some embodiments, the present compounds and compositions find use as entiopure drugs.

In various embodiments, the present invention requires separation of a racemate into its components, the pure enantiomers, i.e. chiral resolution. Techniques to achieve substantially enantiomerically pure compounds are known and include, by way of non-limiting example, crystallization, chromatography (e.g. HPLC), and enzymatic resolution. Various techniques for chiral resolution are found in Proter *Pure Appl. Chem.* 63 (8): 1119-1122, the contents of which are hereby incorporated by reference in their entirety. In various embodiments, measurement of the Eudysmic ratio may assist in determining the final properties of the composition. For example, one enantiomer is the eutomer while the other enantiomer is the distomer and comparison of two may involve the quotient of activity or binding measurements (e.g. $EC_{50}$ or $IC_{50}$).

In further embodiments, the present compounds and compositions are entiopure drugs. However, in instances in which corresponding enantiomers provide different but desirable properties (e.g. physiologically relevant modulation at different serotonin receptors), such enantiomers may be combined as a combination composition of known amounts.

In various embodiments, the present compounds or compositions modulate one or more serotonin receptors, also known as 5-hydroxytryptamine receptors or 5-HT receptors. For example, one or more of $5\text{-}HT_1$ receptors (e.g. one or more of $5\text{-}HT_{1A}$, $5\text{-}HT_{1B}$, $5\text{-}HT_{1C}$, $5\text{-}HT_{1D}$, $5\text{-}HT_{1E}$, $5\text{-}HT_{1F}$), $5\text{-}HT_2$ receptors (e.g. one or more of $5\text{-}HT_{2A}$, $5\text{-}HT_{2B}$, $5\text{-}HT_{2C}$); $5\text{-}HT_3$ receptors; $5\text{-}HT_4$ receptors; $5\text{-}HT_5$ receptors (e.g. $5\text{-}HT_{5A}$); $5\text{-}HT_6$ receptors; and $5\text{-}HT_7$ receptors may be modulated.

In various embodiments, the present compounds or compositions may be full agonist, partial agonist, antagonist, inverse agonist, etc. atone or more receptors described herein (e.g. one or more serotonin receptors).

In some embodiments, the invention provides for partial agonists at one or more receptors described herein (e.g. one or more serotonin receptors) specifically. In some embodiments, the present compounds or compositions are not full agonists at one or more receptors described herein (e.g. one or more serotonin receptors). In some embodiments, such partial agonism may provide constant, weak level of activity at the receptor, as compared to a full agonist. Further, without wishing to be bound by theory, such partial agonism may prevent adaptive regulatory mechanisms that may develop after repeated exposure to potent full agonists or antagonists. Further, in embodiments relating to serotonin receptor modulation, partial agonism of the present compounds or compositions may reduce or eliminate the risk of serotonin syndrome (e.g., fever, cardiac arrhythmia, seizures, loss of consciousness). For example, some $5\text{-}HT_1$ agonists (e.g. triptans) are known to cause serotonin syndrome. Partial agonism is believed to avoid this deleterious side effect.

In various embodiments, the dual partial agonist binds to one or more of the serotonin $5\text{-}HT_7$ and $5\text{-}HT_{1A}$ receptor at physiologically relevant levels. In various embodiments, the dual partial agonist binds to the serotonin $5\text{-}HT_7$ receptor with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM. In various embodiments, the dual partial agonist binds to the serotonin $5\text{-}HT_7$ receptor with a binding affinity ($K_i$) of about 100 nM, or about 90 nM, or about 80 nM, or about 75 nM, or about 70 nM, or about 60 nM, or about 50 nM, or about 40 nM, or about 30 nM, or about 25 nM, or about 20 nM, or about 10 nM, or about 5 nM, or about 4 nM, or about 3 nM, or about 2 nM, or about 1 nM. In various embodiments, the dual partial agonist binds to the serotonin $5\text{-}HT_{1A}$ receptor with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM. In various embodiments, the dual partial agonist binds to the serotonin $5\text{-}HT_{1A}$ receptor with a binding affinity ($K_i$) of about 100 nM, or about 90 nM, or about 80 nM, or about 75 nM, or about 70 nM, or about 60 nM, or about 50 nM, or about 40 nM, or about 30 nM, or about 25 nM, or about 20 nM, or about 10 nM, or about 5 nM, or about 4 nM, or about 3 nM, or about 2 nM, or about 1 nM.

In various embodiments, the dual partial agonist does not bind one or more of the serotonin $5\text{-}HT_{2A}$ and $5\text{-}HT_{2C}$ receptors at physiologically-relevant levels. In various embodiments, the dual partial agonist binds one or more of the serotonin 5-HT$_{2A}$ and 5-HT$_{2C}$ receptors with an affinity of greater than about 300 nM, or greater than about 400 nM, or greater than about 500 nM, or greater than about 750 nM, or greater than about 1 µM. In some embodiments, the dual partial agonist binds one or more of the serotonin 5-HT$_{2A}$ and 5-HT$_{2C}$ receptors with an affinity of about 10 µM, or about 5 µM, or about 1 µM, or about 900 nM, or about 800 nM, or about 750 nM, or about 700 nM, or about 600 nM, or about 500 nM, or about 400 nM, or about 250 nM.

Accordingly, in some embodiments, the present dual partial agonist selectively binds to serotonin 5-HT$_7$ and 5-HT$_{1A}$ receptors over other serotonin receptors. In various embodiments, the dual partial agonist binds one or more of the serotonin 5-HT$_7$ and 5-HT$_{1A}$ receptors with at least about 10-fold, or at least about 20-fold, or at least about 30-fold, or at least about 40-fold, or at least about 50-fold, or at least about 75-fold, or at least about 100-fold higher affinity than one or more of the serotonin 5-HT$_{2A}$ and 5-HT$_{2C}$ receptors. In various embodiments, the dual partial agonist binds one or more of the serotonin 5-HT$_7$ and 5-HT$_{1A}$ receptors with about a 10-fold, or 20-fold, or 25-fold, or 30-fold, or 40-fold, or 50-fold, or 60-fold, or 70-fold, or 75-fold, or 80-fold, or 90-fold, or 100-fold higher affinity than one or more of the serotonin 5-HT$_{2A}$ and 5-HT$_{2C}$ receptors.

In some embodiments, the selective binding to certain serotonin receptors over other serotonin receptors (e.g. a preference for 5-HT$_7$ and 5-HT$_{1A}$ receptors) is enantiomer-mediated. That is, in some embodiments, one enantiomer of a compound displays the selectively binding while the other does not. For example, in some embodiments, the dual partial agonist binds one or more of the serotonin 5-HT$_7$ and 5-HT$_{1A}$ receptors with an at least about 10-fold, or at least about 20-fold, or at least about 30-fold, or at least about 40-fold, or at least about 50-fold, or at least about 75-fold, or at least about 100-fold higher affinity than a corresponding enantiomer. In some embodiments, the dual partial agonist binds one or more of the serotonin 5-HT$_7$ and 5-HT$_{1A}$ receptors with about 10-fold, or about 20-fold, or about 30-fold, or about 40-fold, or about 50-fold, or about 75-fold, or about 100-fold higher affinity than a corresponding enantiomer In various embodiments, the dual partial agonist does not bind one or more of the histamine H1 receptor, dopamine D2, and adrenergic α$_{1A}$ and α$_{1B}$ receptors at physiologically-relevant levels.

In various embodiments, the dual partial agonist binds one or more of the histamine H1 receptor, dopamine D2, and adrenergic α$_{1A}$ and α$_{1B}$ receptors with an affinity of greater than greater than about 500 nM, or greater than about 750 nM, or greater than about 1 µM. In various embodiments, the dual partial agonist binds one or more of the histamine H1 receptor, dopamine D2, and adrenergic au and CHB receptors with an affinity of 10 µM, or about 5 µM, or about 1 µM, or about 900 nM, or about 800 nM, or about 750 nM, or about 700 nM, or about 600 nM, or about 500 nM, or about 400 nM, or about 250 nM.

Accordingly, in some embodiments, the present dual partial agonist selectively binds to serotonin 5-HT$_7$ and 5-HT$_{1A}$ receptors over one or more of the histamine H1 receptor, dopamine D2, and adrenergic aw and α$_{1B}$ receptors. In various embodiments, the dual partial agonist binds one or more of the serotonin 5-HT$_7$ and 5-HT$_{1A}$ receptors with at least about 10-fold, or at least about 20-fold, or at least about 30-fold, or at least about 40-fold, or at least about 50-fold, or at least about 75-fold, or at least about 100-fold higher affinity than one or more of the histamine H1 receptor, dopamine D2, and adrenergic α$_{1A}$ and α$_{1B}$ receptors. In various embodiments, the dual partial agonist binds one or more of the serotonin 5-HT$_7$ and 5-HTw receptors with about a 10-fold, or 20-fold, or 25-fold, or 30-fold, or 40-fold, or 50-fold, or 60-fold, or 70-fold, or 75-fold, or 80-fold, or 90-fold, or 100-fold higher affinity than one or more of the histamine H1 receptor, dopamine D2, and adrenergic α$_{1A}$ and α$_{1B}$ receptors.

In various aspects, the present invention relates to a compound or pharmaceutical composition of the structure represented by Formula (Ia):

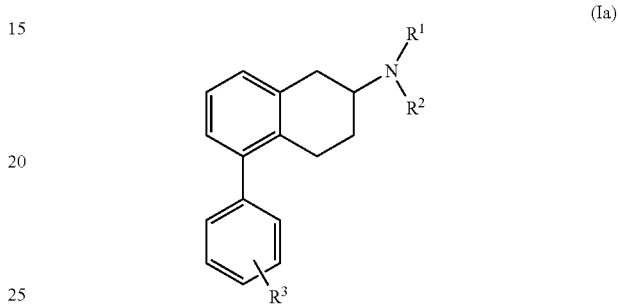

(Ia)

or pharmaceutically acceptable salt thereof, where each of R$^1$, R$^2$, and R$^3$ are defined as above for Formula I.

In some embodiments, the compound or pharmaceutical composition is the (+) enantiomer. In some embodiments, the compound or pharmaceutical composition is the (−) enantiomer.

In some embodiments, each of R$^1$ and R$^2$ is independently hydrogen, alkyl, aryl, halo, nitro, amino, heteroaryl, cycloalkyl, heterocyclic, or alkoxy.

In some embodiments, R$^1$ and R$^2$ are identical. In some embodiments, R$^1$ and R$^2$ are not identical. In some embodiments, one or both of R$^1$ and R$^2$ are methyl.

In some embodiments, R$^3$ is a halo. In some embodiments, R$^3$ is fluoro. In some embodiments, R$^3$ is chloro. In some embodiments, R$^3$ is bromo. In some embodiments, R$^3$ is iodo.

In some embodiments, R$^3$ is in the ortho position. In some embodiments, R$^3$ is in the meta position. In some embodiments, R$^3$ is in the para position.

In some embodiments, both of R$^1$ and R$^2$ are methyl and R$^3$ is halo. In some embodiments, both of R$^1$ and R$^2$ are methyl and R$^3$ is fluoro. In some embodiments, both of R$^1$ and R$^2$ are methyl and R$^3$ is chloro. In some embodiments, both of R$^1$ and R$^2$ are methyl and R$^3$ is chloro, with the proviso that the chloro is not in the meta position. In some embodiments, both of R$^1$ and R$^2$ are methyl and R$^3$ is bromo. In some embodiments, both of R$^1$ and R$^2$ are methyl and R$^3$ is iodo.

In some embodiments, the compound of Formula Ia is enantiomerically pure. In some embodiments, the compound of Formula Ia is substantially the (+) enantiomer. In some embodiments, the compound of Formula Ia is substantially devoid of the (+) enantiomer. In some embodiments, the compound of Formula Ia is substantially the (−) enantiomer. In some embodiments, the compound of Formula Ia is substantially devoid of the (−) enantiomer.

In some embodiments, Formula Ia excludes R$^3$ from being a chloro at the meta position.

In various aspects, the present invention relates to a compound or pharmaceutical composition of the

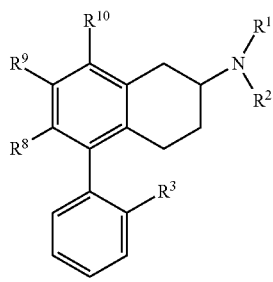

(Ib)

or pharmaceutically acceptable salt, hydrate, or solvate thereof, wherein each of $R^1$, $R^2$, $R^3$, $R^8$, $R^9$, and $R^{10}$ is defined as above for Formula I.

In some embodiments, the compound or pharmaceutical composition is the (+) enantiomer. In some embodiments, the compound or pharmaceutical composition is the (−) enantiomer.

In some embodiments, each of each of $R^1$, $R^2$, $R^8$, $R^9$, and $R^{10}$ is independently hydrogen, alkyl, aryl, halo, nitro, amino, heteroaryl, cycloalkyl, heterocyclic, or alkoxy.

In some embodiments, each of $R^1$, $R^2$, $R^8$, $R^9$, and $R^{10}$ is independently hydrogen, alkyl, alkoxyl, hydroxy, or amino.

In some embodiments, both $R^1$ and $R^2$ are methyl.

In some embodiments, $R^3$ is halo, alkoxy or haloalkyl.

In some embodiments, $R^3$ is halo. In some embodiments, $R^3$ is fluoro. In some embodiments, $R^3$ is chloro.

In some embodiments, $R^3$ is bromo. In some embodiments, $R^3$ is iodo.

In some embodiments, the compound of Formula Ib is substantially the (+) enantiomer. In some embodiments, the compound of Formula Ib is substantially devoid of the (+) enantiomer. In some embodiments, the compound of Formula Ib is substantially the (−) enantiomer. In some embodiments, the compound of Formula Ib is substantially devoid of the (−) enantiomer.

In some embodiments, the compound is:

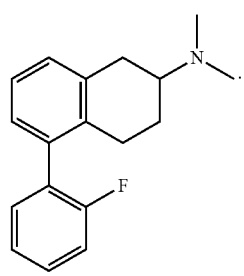 [SMILES: CN(C)C1CCc2c(cccc2-c2ccccc2F)C1]

In some embodiments, the dual partial agonist is the (+) enantiomer of the above compound.

In some embodiments, the compound is:

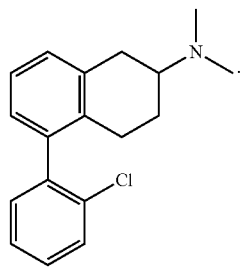

In some embodiments, the dual partial agonist is the (+) enantiomer of the above compound.

In various aspects, the present invention relates to a compound or pharmaceutical composition of the structure represented by Formula (Ic):

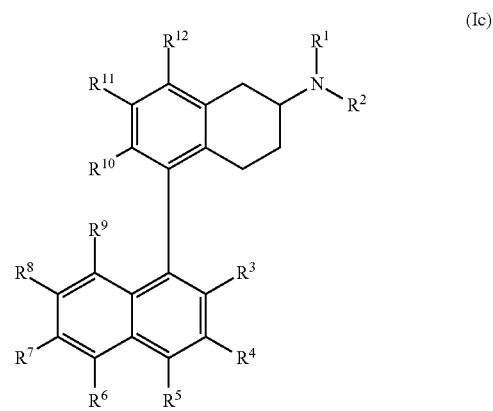

(Ic)

or pharmaceutically acceptable salt, hydrate, or solvate thereof, wherein each of $R^1$-$R^{12}$ is defined as above for Formula I.

In some embodiments, each of $R^1$ to $R^{12}$ is independently hydrogen, alkyl, aryl, halo, nitro, amino, heteroaryl, cycloalkyl, heterocyclic, or alkoxy.

In some embodiments, both $R^1$ and $R^2$ are methyl.

In some embodiments, one or more of $R^3$, $R^4$, $R^5$, $R^6$, $R^7$, $R^8$, and $R^9$ is halo.

In some embodiments, one or more of $R^3$, $R^4$, $R^5$, $R^6$, $R^7$, $R^8$, and $R^9$ is a selected from fluoro, chloro, bromo, and iodo.

In some embodiments, $R^3$ is selected from fluoro, chloro, bromo, and iodo. In some embodiments, $R^3$ is selected from fluoro, chloro, bromo, and iodo and each of $R^4$-$R^9$ is hydrogen.

In some embodiments, the compound of Formula Ic is enantiomerically pure. In some embodiments, the compound of Formula Ic is substantially the (+) enantiomer. In some embodiments, the compound of Formula Ic is substantially devoid of the (+) enantiomer. In some embodiments, the compound of Formula Ic is substantially the (−) enantiomer. In some embodiments, the compound of Formula Ic is substantially devoid of the (−) enantiomer.

In some embodiments, the compound is:

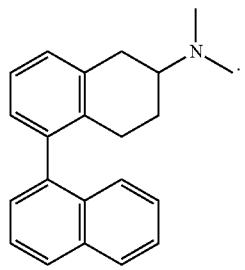 [SMILES: CN(C)C1CCc2c(cccc2-c2cccc3ccccc23)C1]

In some embodiments, the dual partial agonist is the (−) enantiomer of the above compound.

In various embodiments, the compounds may be any one of:

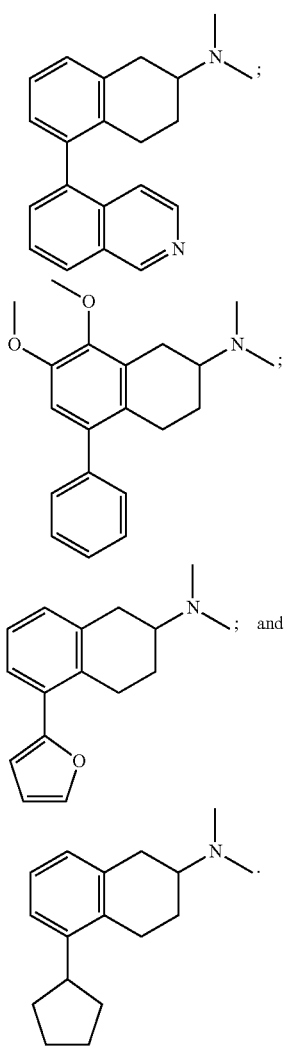

In some embodiments, the compounds and compositions of the present invention may take the form of a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In some embodiments, the compounds and compositions of the present invention can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used.

In one embodiment, the pharmaceutically acceptable excipients are sterile when administered to a subject. Water, saline solutions and aqueous dextrose and glycerol solutions can also be employed as liquid excipients. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

The compounds and compositions of the present invention can be present in various formulations. Any compound and composition (and/or additional agents) described herein can take the form of solutions, suspensions, emulsion, drops, tablets, pills, pellets, capsules, capsules containing liquids, powders, sustained-release formulations, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the compounds and compositions can also include a solubilizing agent. Also, the compounds and compositions can be delivered with a suitable vehicle or delivery device as known in the art. Combination therapies outlined herein can be co-delivered in a single delivery vehicle or delivery device.

The formulations comprising the compounds and compositions of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In some embodiments, the administering is effected orally. In some embodiments, the administering is by absorption through epithelial or mucocutaneous linings (e.g., oral mucosa). Various delivery systems are known, e.g., encapsulation in liposomes, microparticles, microcapsules, capsules, etc., and can be used to administer. In various embodiments, the compounds and compositions of the present invention are formulated to be suitable for oral delivery. In various embodiments, the compounds and compositions of the present invention are formulated to be suitable for transmucosal delivery (see, e.g. Msatheesh, et al. Expert Opin Drug Deliv. 2012 June; 9(6):629-47, the entire contents of which are hereby incorporated by reference).

Compositions or compounds for oral delivery can be in the form of tablets, lozenges, aqueous or oily suspensions, granules, powders, emulsions, capsules, syrups, or elixirs, for example. In some embodiments, the compounds and compositions of the present invention are in the form of a capsule, tablet, patch, or lozenge. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active capsule containing a driving compound capable of driving any compound or composition described herein is also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the compounds and compositions of the present invention, or formulations thereof, substantially accumulate in the brain. In various embodiments, the compounds and compositions, or formulations thereof, deliver a physiological amount of dual partial agonist to the brain for at least about 6 hours, or at least about 9 hours, or at least about 12 hours, or at least about 15 hours, or at least about 18 hours, or at least about 21 hours, or at least about 24 hours. In various embodiments, the compounds and compositions, or formulations thereof, deliver a physiological amount of dual partial agonist to the brain for about 6 hours, or about 9 hours, or about 12 hours, or about 15 hours, or about 18 hours, or about 21 hours, or about 24 hours. In some embodiments, the duration of activity is longer for the compounds and compositions of the present invention in which the total number of atoms that comprise substituents $R^3$ to $R^7$ are at least about 5, and not more than about 20 atoms, not including hydrogen atoms (e.g. between about 5 to about 10 non-hydrogen atoms, or between about 5 to about 15 non-hydrogen atoms, or between about 10 to about 15 non-hydrogen atoms). In some embodiments, the duration of activity is longer for the compounds and compositions of the present invention which are not substantially metabolized, for instance, via P450 and any subtype or family member thereof.

In some embodiments, when orally administered to a mammal, the unit dosage of any compound or composition of the invention herein is less than about 100 mg, or less than about 90 mg, or less than about 80 mg, or less than about 70 mg, or less than about 60 mg, or less than about 50 mg, or less than about 40 mg, or less than about 30 mg, or less than about 25 mg, or less than about 20 mg, or less than about 15 mg. In some embodiments, when orally administered to a mammal, the unit dosage of any compound or composition of the invention herein is about 10 to about 100 mg, or about 10 to about 90 mg, or about 10 to about 80 mg, or about 10 to about 70 mg, or about 10 to about 60 mg, or about 10 to about 50 mg, or about 10 to about 40 mg, or about 10 to about 30 mg, or about 10 to about 20 mg, or about 10 to about 15 mg. In some embodiments, when orally administered to a mammal, the unit dosage of any compound or composition of the invention herein is about 5 mg, or about 7.5 mg, or about 10 mg, or about 12.5 mg, or about 15 mg, or about 17.5 mg, or about 20 mg, or about 22.5 mg, or about 25 mg, or about 30 mg, or about 40 mg, or about 50 mg.

While the dose of the compounds or compositions of the present invention are provided above, in general, the doses of additional therapeutic agents that are useful are known to those in the art. For example, doses may be determined with reference *Physicians' Desk Reference*, 66th Edition, PDR Network; 2012 Edition (Dec. 27, 2011), the contents of which are incorporated by reference in its entirety. In some embodiment, the present invention allows a patient to receive doses that exceed those determined with reference Physicians' Desk Reference.

Any compound or composition (and/or additional therapeutic agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromoi. Sci. Rev. Macromol. Chem.* 23:61; see also Levy et al, 1985, Science 228:190; During et al., 1989, *Ann. Neurol.* 25:351; Howard et al., 1989, *J. Neurosurg.* 71:105).

Administration of any compounds or compositions (and/or additional agents) described herein can, independently, be one to four times daily. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

The present compounds and compositions also find use in various therapeutic methods.

In some aspects, the present invention relates to a method of treating or preventing a neuropsychiatric disease or disorder, comprising administering an effective amount of a compound or composition described herein to a patient in need thereof.

In some embodiments, the neuropsychiatric disease or disorder is one or more of ASD (including autism), anxiety, depression, obsessive-compulsive disorders, schizophrenia, suicide, migraine, emesis, alcoholism and neurodegenerative disorders.

In some embodiments, the neuropsychiatric disease or disorder is one or more of autism spectrum disorder (ASD); Asperger syndrome, Fragile X syndrome (FXS), Prader-Willi syndrome, Rett syndrome, Tourette syndrome, attention-deficit hyperactivity disorder (ADHD), obsessive-compulsive disorder, psychotic disorders, psychostimulant addiction and generalized anxiety.

In some embodiments, the neuropsychiatric disease or disorder is a neuropsychiatric disorder that is associated with altered dopamine function and includes, for example, movement disorders, such as, Huntington's chorea, periodic limb movement syndrome, restless leg syndrome (akathesia), Tourrette's syndrome, Sundowner's syndrome, schizophrenia, Pick's disease, Punch drunk syndrome, progressive subnuclear palsy, Korsakow's (Korsakoff's) syndrome, Multiple Sclerosis or Parkinson's disease; medication-induced movement disorders, such as, neuroleptic-induced Parkinsonism, malignant syndrome, acute dystonia, stroke, trans-ischaemic attack, tardive dyskiesia or multiple systems atrophy (Parkinson's plus); eating disorders, such as, anorexia cachexia or anorexia nervosa; and cognitive disorders, such as, Alzheimer's disease or dementia, for example, pseudo dementia, hydrocephalic dementia, subcortical dementia or dementia due to Huntington's chorea or Parkinson's disease; psychiatric disorders characterized by anxiety such as panic disorder, agoraphobia, obsessive-compulsive disorder, post traumatic stress disorder, acute stress disorder, generalized anxiety disorder and anxiety disorders due to other medical disorders, such as, depression.

In some embodiments, diagnosis and/or drug effectiveness for any of these disorders is evaluated with reference to the Diagnostic and Statistical Manual of Mental Disorders, 5th Edition (DSM-5).

In some embodiments, the treatment comprises a reduction in the frequency of one or more of stereotypy, self-injurious behaviors, compulsions, and tics.

In some aspects, the present invention provides a method of treating one or more ASD comprising administering an effective amount of a compound or composition described herein to a patient in need thereof. ASD are a group of diseases characterized by varying degrees of impairment in communication skills, social interactions, and restricted, repetitive and stereotyped patterns of behavior. The difference in the diseases depends on the time of onset, the rate of symptom development, the severity of symptoms, and the exact nature of the symptoms. These disorders range from mild to severe impairment and include such diseases as autism, Asperger's syndrome, PDD-NOS, Rett's disorder, childhood disintegrative disorder, semantic communication disorder, non-verbal learning disabilities, high functioning autism, hyperlexia and some aspects of attention deficit hyperactivity disorder.

In various embodiments, the present methods may be useful in treating one or more symptoms or characteristics of ASD, which include, by way of non-limiting example, include stereotyped movements, social withdrawal and averted gaze including an inability to make eye contact, repetitive behaviors and obsessions, anxiety, attention deficit, hyperactivity, depression, a reclusive personality, and the inability to understand feelings.

Patients afflicted with ASD may have an aversion to physical affection or contact, ignore communication from others, or if socially engaged, demonstrate a marked inability to communicate or relate to others. Communication difficulties may manifest as a monotone voice, an inability to control the volume of their voice, echolalia or an inability to talk at all. Individuals with autism spectrum disorders may also suffer from visual difficulties, comprehension difficulties, sound and light sensitivity and mental retardation.

The effectiveness of the compositions for these and related conditions can be routinely demonstrated according to a variety of methods, including, for example, by measuring markers such as those measured in the Checklist of Autism in Toddlers (CHAT), the modified Checklist for Autism in Toddlers (M-CHAT), the Screening Tool for Autism in Two-Year-Olds (STAT), the Social Communication Questionnaire (SCO), the Autism Spectrum Screening Questionnaire (ASSQ), the Australian Scale for Asperger's Syndrome, the Childhood Asperger Syndrome Test (CAST), the Autism Diagnosis Interview-Revised (ADI-R), the Autism Diagnostic Observation Schedule (ADOS-G), the Childhood Autism Rating Scale (CARS), audiologic hearing evaluation, Administered PTSD Scale, the Eysenck Personality Inventory, the Hamilton Anxiety Scale, or in various animal models such as the well-known Vogel (thirsty rat conflict) test, or the elevated plus maze test. Effective amounts of the present compounds and compositions (and, optionally, an additional therapeutic agent) will measurably prevent, decrease the severity of, or delay the onset or duration of, one or more of the foregoing autism spectrum disorders or related disorders of symptoms of such disorders in a patient. Further, the DSM-5, e.g. the section entitled "ASD and Social Communication Disorder," which is hereby incorporated by reference in its entirety, and the International Statistical Classification of Diseases and Related Health Problems-10th Revision (ICD-10) can be used as diagnostic classifications for ASD. In some embodiments, stereotypy is useful as a diagnostic for ASD, including in children with autism.

In some embodiments, the present compounds and compositions, or formulations thereof, are combined with or further comprise one or more additional therapeutic agent. In some embodiments, there is provided a method of treatment of any of the diseases or disorders described herein by administering an effective amount of a present compound or composition and an additional therapeutic agent. In some embodiments, there is provided a method of treatment of any of the diseases or disorders described herein by administering an effective amount of a present compound or composition to a patient that is undergoing treatment with an additional therapeutic agent. In some embodiments, the compound of composition of the present invention is co-formulated with one or more additional therapeutic agent. In various embodiments, the present compounds and compositions and the additional therapeutic agent has a synergistic effect and/or allow for a reduction of effective dose of one or both of the present compounds and compositions and the additional therapeutic agent.

In some embodiments, including, by way of non-limitation, in the treatment of ASD, the additional therapeutic agent is one or more of a serotonin reuptake inhibitors, selective serotonin reuptake inhibitors including, but not limited to, fluoxetine, fluvoxamine, sertraline, clomipramin; antipsychotic medications including, but not limited to, haloperidol, thioridazine, fluphenazine, chlorpromazine, risperidone, olanzapine, ziprasidone; anti-convulsants, including, but not limited to, carbamazepine, lamotrigine, topiramate, valproic acid, stimulant medications including, but not limited to, methylphenidate, α2-adrenergic agonists, amantadine, and clonidine; antidepressants including, but not limited to, naltrexone, lithium, and benzodiazepines; antivirals, including, but not limited to, valtrex; secretin; axiolytics including, but not limited to, buspirone; immunotherapy agents anesthetic, and hypnotic or muscle relaxant agent(s). Additional adjunctive therapeutic agents include vitamins including, but not limited to, B-vitamins (e.g. B6, B12, thiamin), vitamin A, and essential fatty acids. Additional therapeutic agents may also include melatonin, omega-3 fatty acids, glutamate receptor related medications, and oxytocin. Additional therapies may also include behavioral modification (including, without limitation, the Lovaas Model based on Applied Behavior Analysis (ABA) and the Early Start Denver Model, as well as floortime, Pivotal Response Therapy and Verbal Behavior Therapy) and changes in diet such as a gluten-casein free diet.

In some embodiments, the subject of the present invention is not undergoing ASD treatment with risperidone or aripiprazole, as such agents may worsen stereotypy.

In some aspects, the present invention relates to a method of treating stereotypy, comprising administering an effective amount of a compound or composition described herein to a patient in need thereof. In various embodiments, the present methods pertain to the treatment of stereotypic behaviors or stereotypy. In various embodiments, the present methods pertain to the treatment of restricted repetitive behaviors (RRB).

Stereotypic behaviors may be verbal or nonverbal, fine or gross motor-oriented, as well as simple or complex. Additionally, they may occur with or without objects. Some forms involve stereotyped and repetitive motor mannerisms or use of language. Common examples of stereotypy are hand flapping, body rocking, toe walking, spinning objects, sniffing, immediate and delayed echolalia, and running objects across one's peripheral vision. Other forms involve more complex behaviors, such as restricted and stereotyped patterns of interest or the demand for sameness. These forms may involve a persistent fixation on parts of objects or an inflexible adherence to specific, nonfunctional routines or rituals. For example, a child engaging in stereotypic behavior may attend only to specific parts of objects (e.g., car wheels, doll eyes). Alternatively, a child may insist on playing with his or her toys in a very specific fashion (e.g., lining blocks up in identical rows repetitively). In various embodiments, the present methods treat any of these stereotypy behaviors. Further feature of stereotypy are described in Cunningham et al. Res Autism Spectr Disord. 2008; 2(3): 469-479, the contents of which are hereby incorporated by reference in their entirety.

Additional stereotypy behaviors that are treated include the following. Stereotypic behaviors of the face include grimacing, lips or tongue movements, opening the mouth, mouth stretching, licking, smoking, puffing noise, and sucking objects. Stereotypic behaviors of the head and neck include head tilting, shaking, nodding, hair twirling, head banging, neck stretching, teeth grinding, hair pulling, tongue wagging, biting bottoms, and neck extension. Stereotypic behaviors of the trunk include body rocking, spin and spinning or rotation of entire body. Stereotypic behaviors of the shoulders include ending, scrunching; arching the back; and shrugging the shoulders. Stereotypic behaviors of the arm/leg include arm flapping, bilateral repetitive movements involving the arms and hands such as crossing the arms on the chest, stamping the feet, tapping one's feet, and heel and toe walking. Stereotypic behaviors of the hand/finger include hand flapping, slapping, nail biting, finger wiggling, shaking, tapping, waving, clapping, opening-closing, rotating or twirling the hand or fingers, thumb-sucking, pointing, fanning fingers, fluttering fingers in front of the face, picking skin, scratch self, and arrange objects. Stereotypic behaviors of the hand/finger with object include shaking, tapping, banging, twirling an object, tapping pencils, touching, rubbing, repetitive ordering, arrange toys in patterns, adding objects to a line, and manipulating of objects. Stereotypic behaviors of the gait include pacing, jumping, running, skipping, and spinning. Self-directed stereotypic behaviors include covering the ears, mouthing, smelling, rubbing the eyes, tapping the chin, slapping self or an object or surface, touching genitals, and self-mutilating behavior. Visual stereotypic behaviors include atypical visual explanatory behaviors such as staring at an object or the fingers 'out of the corner of the eyes, eyelid closure, and squinting eyes. Stereotypic behaviors of the vocal and speech include vocalization, humming, tongue clucking, echolalic words/phrases, and telling or asking.

In some embodiments, stereotypic behaviors are treated in the context of ASD (inclusive of autisim, Aspeger's syndrome, Rett's disorder, childhood disintegrative disorder, and Pervasive Developmental Disorder, Not Otherwise Specified (PDD-NOS)). However, in various embodiments, the present methods also relate to treatment of stereotypic behaviors in the context of other diseases, including by way of example, other sensory, intellectual, or developmental disabilities such as mental retardation and developmental delay or sensory deprivation syndromes such as Smith-Magenis Syndrome and Cri-du-Chat syndrome. Moreover, repetitive motor behavior, including stereotypy and higher-order restrictive behaviors (e.g. compulsions), are also observed in other neurodevelopmental and neuropsychiatric disorders, such as Fragile X syndrome (FXS, stereotypy), Prader-Willi syndrome (self-injurious behaviors [SIB] and compulsions), Rett syndrome (stereotypy, compulsions, SIB), Tourette syndrome (tics, SIB, compulsions), attention-deficit hyperactivity disorder, obsessive-compulsive disorder, psychotic disorders, psychostimulant addiction and generalized anxiety (e.g. akathisia), with many instances of co-morbidity In some embodiments, including, for example, in the treatment of stereotypy, the present methods may include an additional therapeutic agent that is an antipsychotic agent, including, by way of example, haloperidol and risperidone (see, e.g., Malone et al. CNS Drugs. 2005, 19(11):923-34, the contents of which are hereby incorporated by reference). Also, risperidone and pentoxifylline, alone or in combination may be used. Further additional therapeutic agents include Serotonin reuptake inhibitors (SRIs) such as fluvoxamine and serotonin non-specific reuptake inhibitor of clomipramine and divalproex.

Stereotypies can be assessed using, for example, the 43-item questionnaire of Repetitive Behavior Scale-Revised (RBS-R) (Bodfish et al., 2000 J Autism Dev Disord. 2000; 30(3):237-43, the contents of the which are hereby incorporated by reference in their entirety) and/or the Repetitive and Restricted Behaviour Scale (RRB) (Bourreau et al., Eur Child Adolesc Psychiatry. 2009; 18(11):675-82, the contents of the which are hereby incorporated by reference in their entirety).

In some aspects, the present invention relates to a method of selectively modulating serotonin 5-HT$_7$ and 5-HT$_{1A}$ receptors, comprising contacting a cell with a compound or composition described herein, wherein the modulation is partial antagonism.

In some aspects, the present invention relates to a method of synthesizing a compound that is stereoselective for one or more serotonin receptors. In some embodiments, the synthesis of various 5-PAT compounds using Scheme 1 below is provided.

The invention provides kits that can simplify the administration of any agent described herein. An illustrative kit of the invention comprises any composition described herein in unit dosage form. In one embodiment, the unit dosage form is a container, containing any compound or agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

In some embodiments, the present invention provides a compound or a pharmaceutical composition of the structure represented by Formula II:

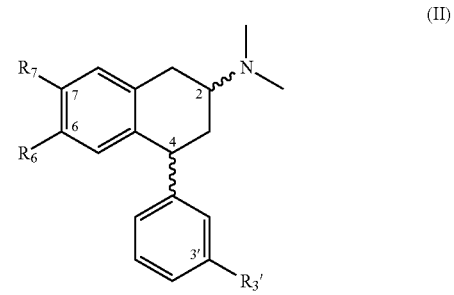

or a pharmaceutically acceptable salt, hydrate, or solvate thereof, wherein $R_3$ is H, Cl, or Br, $R_6$ is OCH$_3$ or OH, and $R_7$ is H or Cl. In some embodiments, the compound of Formula II is the (+) enantiomer. In some embodiments, the compound of Formula II is the (−) enantiomer. In various embodiments, the compound of Formula II is in the (+)-cis, (+)-trans, (−)-cis, or (−)-trans configuration. In an embodiment, the compound of Formula II is in the (−)-trans configuration.

Illustrative compounds of the Formula II are listed in Table 5 below:

TABLE 5

| Compound | Configuration | $R_3$ | $R_6$ | $R_7$ |
|---|---|---|---|---|
| 7a | (+)-trans | H | OCH$_3$ | Cl |
| 7b | (−)-trans | H | OCH$_3$ | Cl |
| 7c | (+)-cis | H | OCH$_3$ | Cl |
| 7d | (−)-cis | H | OCH$_3$ | Cl |
| 7e | (+)-trans | Cl | OCH$_3$ | Cl |
| 7f | (−)-trans | Cl | OCH$_3$ | Cl |
| 7g$^a$ | (+)-cis | Cl | OCH$_3$ | Cl |
| 7h$^a$ | (−)-cis | Cl | OCH$_3$ | Cl |
| 7i | (+)-trans | Br | OCH$_3$ | Cl |
| 7j | (−)-trans | Br | OCH$_3$ | Cl |
| 7k | (+)-trans | Cl | OCH$_3$ | H |
| 7l | (−)-trans | Cl | OCH$_3$ | H |
| 7m | (+)-trans | H | OH | Cl |
| 7n | (−)-trans | H | OH | Cl |

In some embodiments, the present invention provides a compound or a pharmaceutical composition of the structure represented by Formula IIa:

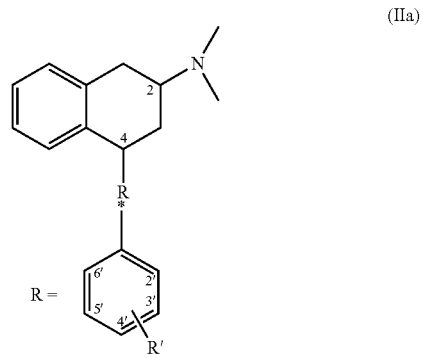

or a pharmaceutically acceptable salt, hydrate, or solvate thereof. In some embodiments, the 2' and 6' positions of R' are independently F, Cl, Br, or I. In other embodiments, the 3' and 5' positions of R' are independently F, Cl, Br, or I. In some embodiments, the compound of Formula IIa is the (+)

enantiomer. In some embodiments, the compound of Formula IIa is the (−) enantiomer. In various embodiments, the compound of Formula IIa is in the (+)-cis, (+)-trans, (−)-cis, or (−)-trans configuration.

In various embodiments, the present compounds and compositions of Formula II and Formula IIa comprise at least about 70%, or at least about 80%, or at least about 85%, or at least about 90%, or at least about 95%, or at least about 97%, or at least about 99% of a single enantiomer. In various embodiments, a least about 85%, or at least about 90%, or at least about 95%, or at least about 97%, or at least about 99% of a single enantiomer. In some embodiments, the compositions of the present invention comprises less than about 30%, or less than about 20%, or less than about 15%, or less than about 10%, or less than about 5%, or less than about 3%, or less than about 1% of a single enantiomer. In some embodiments, the present compounds and compositions of Formula II and Formula IIa are substantially in the form of a single enantiomer and essentially free of the corresponding enantiomer. In various embodiments, the present invention pertains to separation of a racemate into its components, the pure enantiomers, i.e. chiral resolution. In further embodiments, the present compounds and compositions of Formula II and Formula IIa are enantiopure drugs. However, in instances in which corresponding enantiomers provide different but desirable properties (e.g. physiologically relevant modulation at different serotonin receptors), such enantiomers may be combined as a combination composition of known amounts.

In various embodiments, the present compounds or compositions of Formula II and Formula IIa modulate one or more serotonin receptors. For example, one or more of $5\text{-HT}_1$ receptors (e.g. one or more of $5\text{-HT}_{1A}$, $5\text{-HT}_{1B}$, $5\text{-HT}_{1C}$, $5\text{-HT}_{1D}$, $5\text{-HT}_{1E}$, $5\text{-HT}_{1F}$); $5\text{-HT}_2$ receptors (e.g. one or more of $5\text{-HT}_{2A}$, $5\text{-HT}_{2B}$, $5\text{-HT}_{2C}$); $5\text{-HT}_3$ receptors; $5\text{-HT}_4$ receptors; $5\text{-HT}_5$ receptors (e.g. $5\text{-HT}_{5a}$); $5\text{-HT}_6$ receptors; and $5\text{-HT}_7$ receptors may be modulated. In an embodiment, the present compounds or compositions of Formula II and Formula IIa modulate the $5\text{-HT}_{2A}$ receptor. In another embodiment, the present compounds or compositions of Formula II and Formula IIa modulate the $5\text{-HT}_{2B}$ receptor. In a further embodiment, the present compounds or compositions of Formula II and Formula IIa modulate the $5\text{-HT}_{2C}$ receptor. In a further embodiment, the present compounds or compositions of Formula II and Formula IIa modulate two of, or three of the $5\text{-HT}_{2A}$ receptor, $5\text{-HT}_{2B}$ receptor, and $5\text{-HT}_{2C}$ receptor.

In various embodiments, the present compounds or compositions of Formula II and Formula IIa may be full agonist, partial agonist, antagonist, inverse agonist, etc. at one or more receptors described herein (e.g. one or more serotonin receptors). In some embodiments, the invention provides for partial agonists at one or more receptors described herein (e.g. one or more serotonin receptors) specifically. In some embodiments, the present compounds or compositions are not full agonists at one or more receptors described herein (e.g. one or more serotonin receptors). In some embodiments, such partial agonism may provide constant, weak level of activity at the receptor, as compared to a full agonist.

In various embodiments, the present compounds or compositions of Formula II and Formula IIa modulate the $5\text{-HT}_{2A}$ receptor. In an embodiment, the present compound or composition is an inverse agonist of the $5\text{-HT}_{2A}$ receptor. In an embodiment, the present compound or composition is an antagonist of the $5\text{-HT}_{2A}$ receptor. In various, the present compounds or compositions do not activate the $5\text{-HT}_{2A}$ receptor.

In various embodiments, the present compounds or compositions of Formula II and Formula IIa modulate the $5\text{-HT}_{2B}$ receptor. In an embodiment, the present compound or composition is an inverse agonist of the $5\text{-HT}_{2B}$ receptor. In an embodiment, the present compound or composition is an antagonist of the $5\text{-HT}_{2B}$ receptor. In various, the present compounds or compositions do not activate the $5\text{-HT}_{2B}$ receptor.

In various embodiments, the present compounds or compositions of Formula II and Formula IIa modulate the $5\text{-HT}_{2C}$ receptor. In an embodiment, the present compound or composition is an agonist of the $5\text{-HT}_{2C}$ receptor.

In an embodiment, the present compound or composition of Formula II and Formula IIa is an inverse agonist of the $5\text{-HT}_{2A}$ receptor and $5\text{-HT}_{2B}$ receptors and an agonist of the $5\text{-HT}_{2C}$ receptor. In another embodiment, the present compound or composition is an antagonist of the $5\text{-HT}_{2A}$ receptor and $5\text{-HT}_{2B}$ receptors and an agonist of the $5\text{-HT}_{2C}$ receptor. In a further embodiment, the present compound or composition is an inverse agonist of the $5\text{-HT}_{2A}$ receptor and an agonist of the $5\text{-HT}_{2C}$ receptor, and does not activate the $5\text{-HT}_{2B}$ receptor.

In various embodiments, the compound or composition of Formula II and Formula IIa does not bind one or more of $5\text{-HT}_1$ receptors, $5\text{-HT}_3$ receptors, $5\text{-HT}_4$ receptors, $5\text{-HT}_5$ receptors, $5\text{-HT}_6$ receptors, and/or $5\text{-HT}_7$ receptors.

In various embodiments, the compound or composition of Formula II and Formula IIa does not bind one or more of the dopamine D1, dopamine D2, norepinephrine a, norepinephrine p, histamine H1, and adrenergic $\alpha_{1A}$ and $\alpha_{1B}$ receptors at physiologically-relevant levels. In an embodiment, the compound or composition of Formula II and Formula IIa does not bind/activate the histamine H1 receptor. In an embodiment, the compound or composition of Formula II and Formula IIa does not bind/activate the hERG ion channel.

Pharmaceutically acceptable salts, administration routes, pharmaceutical compositions, pharmaceutical excipients, formulations, etc. applicable to compounds or compositions of Formula II and Formula IIa are described above.

In various embodiments, the present invention provides methods of preventing or treating neuropsychiatric disorders, comprising administering an effective amount of a pharmaceutical composition and/or formulation (and/or additional therapeutic agent) described herein, including for example compounds or compositions of Formula II and Formula IIa, to a subject in need thereof. Illustrative neuropsychiatric disorders include, but are not limited to, obesity, substance abuse, addiction (e.g., cocaine addiction and amphetamine/methamphetamine addiction), psychosis anxiety, depression, dementia, schizophrenia, psychosis, attention-deficit hyperactivity, sleep disorders, compulsive behavioral disorders (e.g., binge eating). In various embodiments, the neuropsychiatric disorders are associated with inattention, impulsivity, and memory deficit. In an embodiment, methods of the invention prevent or treat the cognitive dysfunctions associated with neuropsychiatric disorders. For example, methods of the invention may enhance attention, reduce impulsivity, and/or improve memory in treated subjects. In an embodiment, methods of the invention reduce hyperactivity in treated subjects. Various methods for evaluating the cognitive function of treated subjects are known in the art. In an embodiment, methods of the invention reduce hunger and/or reduce weight gain in treated subjects.

In various embodiments, the present invention provides methods of preventing or treating neurodegenerative disorders, comprising administering an effective amount of a pharmaceutical composition and/or formulation (and/or additional therapeutic agent) described herein to a subject in need thereof. Illustrative neurodegenerative disorders include, but are not limited to, Parkinson's Disease and Alzheimer's Disease.

In various embodiments, the present invention provides methods of preventing or treating gastrointestinal disorders (e.g., irritable bowel syndrome), comprising administering an effective amount of a pharmaceutical composition and/or formulation (and/or additional therapeutic agent) described herein to a subject in need thereof.

In various embodiments, the present invention provides methods of preventing or treating genitor-urinary tract disorders (e.g., bladder control), comprising administering an effective amount of a pharmaceutical composition and/or formulation (and/or additional therapeutic agent) described herein to a subject in need thereof.

Additional diseases or disorders that may be treated using methods of the invention include those described in WO 2010/129048, the entire contents of which are incorporated herein by reference.

In various, administration the present compounds or compositions of Formula II and Formula IIa causes minimal or no side effects in treated subjects. In an embodiment, administration of the present compounds or compositions is not associated or minimally associated with those side effects caused by activation of the $5\text{-}HT_{2A}$ receptor such as hallucination. In an embodiment, administration of the present compounds or compositions is not associated or minimally associated with those side effects caused by activation of the $5\text{-}HT_{2B}$ receptor such as valvular heart disease and/or pulmonary hypertension. In an embodiment, administration of the present compounds or compositions is not associated or minimally associated with those side effects caused by $5\text{-}HT_{2B}$ receptor inactivation such as weight gain.

In various embodiments, the present compounds or compositions of Formula II and Formula IIa do not have stimulant and/or sedative properties. In various embodiments, the present compounds or compositions of Formula II and Formula IIa are not addictive.

Definitions

The term "acyl" means both substituents of the formula Rx-C(O)—, where Rx is alkyl, heteroalkyl, alkenyl, alkynyl, cycloalkyl, heterocycloalkyl, aryl, arylalkyl, heteroaryl, and heteroarylalkyl.

The term "alkyl" means both "unsubstituted alkyls" and "substituted alkyls," the latter of which refers to alkyl moieties having substituents replacing a hydrogen on one or more carbons of the hydrocarbon backbone.

Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonate, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively. In some embodiments, the alkyl group may have from 1 to 12 carbon atoms, e.g. about 1 carbon atom, or about 2 carbon atoms, or about 3 carbon atoms, or about 4 carbon atoms, or about 5 carbon atoms, or about 6 carbon atoms, or about 7 carbon atoms, or about 8 carbon atoms, or about 9 carbon atoms, or about 10 carbon atoms, or about 11 carbon atoms, or about 12 carbon atoms. Illustrative alkyl groups include methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms. Illustrative alkoxy substituents include, but are not limited to, methoxy, ethoxy, propoxy, isopropoxy, cyclopropyloxy and cyclohexyloxy. In some embodiments, the alkoxy is a lower alkoxy (containing one to six carbon atoms). The alkoxy substituent is optionally substituted.

The terms "alkenyl" and "alkynyl" refer to unsaturated aliphatic groups analogous in length and possible substitution to the alkyls described above, but that contain at least one double or triple bond, respectively. In some embodiments, the "alkenyl" or "alkynyl" group may have from 2 to 12 carbon atoms, e.g. about 2 carbon atoms, or about 3 carbon atoms, or about 4 carbon atoms, or about 5 carbon atoms, or about 6 carbon atoms, or about 7 carbon atoms, or about 8 carbon atoms, or about 9 carbon atoms, or about 10 carbon atoms, or about 11 carbon atoms, or about 12 carbon atoms.

Amino or "amine" substituents include those of the formula —N($R_b$)$_2$, where $R_b$ is hydrogen, alkyl, (halo)alkyl, alkenyl, alkynyl, carbocyclyl, carbocyclylalkyl, aryl, aralkyl, heterocycloalkyl, heterocycloalkylalkyl, heteroaryl heteroarylalkyl, or other substituent described herein. When —N($R_b$)$^2$ has two $R_b$ substituents other than hydrogen, they can be combined with the nitrogen atom to form a 4-, 5-, 6- or 7-membered ring. For example, —N($R_b$)$^2$ is intended to include, for example, pyrrolidinyl and morpholinyl.

Amide or "amido" substituents include those of the formula —C(O)N($R_y$)$_2$ or —NHC(O)$R_y$, where $R_y$ is selected from the group consisting of hydrogen, alkyl, alkenyl, alkynyl, carbocyclyl, carbocyclylalkyl, cycloalkyl, aryl, heteroaryl, or other substituent described herein. The $R^y$ of —N($R_y$)$_2$ of the amide may optionally be taken together with the nitrogen to which it is attached to form a 4-, 5-, 6- or 7-membered ring.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "halogen" and "halo" designate fluoro, chloro, bromo or iodo.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The terms "heterocyclic" or "heterocyclo" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring, which typically contains from 3 to 14 ring atoms, from 3 to 8 ring atoms, from 3 to 6 ring atoms, or from 5 to 6 ring atoms. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, anthracene, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The term "heteroatom" as used herein means an atom of any element other than carbon or hydrogen. Preferred heteroatoms are nitrogen, oxygen, sulfur and phosphorus.

The term "hydroxyl" means —OH.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, the group substituents described above and for example, hydroxy, halogen, cyano, nitro, $C_1$-$C_8$alkyl, $C_2$-$C_8$ alkenyl, $C_2$-$C_8$alkynyl, $C_1$-$C_{8alkoxy}$, $C_2$-$C_5$alkyl ether, $C_1$-$C_8$alkanone, $C_1$-$C_{8alkylthio}$, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —$CONH_2$, mono- or di-($C_1$-$C_8$alkyl)aminocarbonyl, —$SO_2NH_2$, and/or mono or di($C_1$-$C_6$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

"Substituted" means having substituents replacing an atom and includes one or more of halo, acyl, acyloxy, alkyl, heteroalkyl, alkenyl, heteroalkenyl, alkynyl, heteroalkynyl, alkoxy, alkoxycarbonyl, cycloalkyl, heterocycloalkyl, aryl, arylalkyl, heteroaryl, heteroarylalkyl, hydroxy, cyano, trifluoromethyl, trifluoromethoxy, nitro, and trimethylsilanyl, ether, ester, sulfide, disulfide, sulfonyl, sulfinyl, sulfonamidyl, sulfonate, sulfoxyl, phosphate ester, phosphine, borate ester, carbonyl, carboxylate, carbamate, amine, imide, and quinidine. Such substituents can also include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety.

The term "sulfhydryl" or "thiol" means —SH.

The term "treat" or "treatment" means any degree of reduction of symptoms or causation of a disease or medical condition. The term "prevent" or "prevention" means any degree of avoiding the onset or acquisition of a disease or medical condition.

As used herein, "consisting essentially of" allows the inclusion of materials or steps that do not materially affect the basic and novel characteristics of the claim. Any recitation herein of the term "comprising" can be exchanged with "consisting essentially of" or "consisting of".

This invention is further illustrated by the following non-limiting examples.

5-Pat Synthetic Examples

Example 1: 5-PAT Synthesis

Synthesis of compounds described herein is shown in Scheme 1, which involves 6-steps. Briefly, 5-Br-tetralone (1), obtained by reacting 1-tetralone with bromine/$AlCl_3$, was reduced to give the corresponding alcohol (2) that was treated with pTSA to obtain the olefin (3) to obtain the epoxide (4), that was treated with pTSA to obtain key intermediate 5-Br-2-tetralone (5). 5-Br-2-tetralone can be reacted with a wide variety of commercially-available boronic acid derivatives (6). These organoboron when used in the Suzuki-Miyaura cross coupling reaction allow synthesis of the compounds described herein. Thus, in Scheme 1, 5-bromo-2-tetralone (5) was reacted with Tetrakis triphenylphosphine Pd [0], the mixture was degassed, and the 2'-F- or 2'-Cl-phenylboronic acid was added. The reaction mixture was stirred at 80° C. for 3h and then cooled to room temperature before adding $H_2O_2$ to quench excess boronic acid to obtain the 5-(2'-F- or 2'-Cl)-phenyl-2-tetralones (7). Reductive amination with dimethylamine gave 5-(2'[o]-F or Cl)-phenyl-2-dimethylaminotetralin racemates (8), resolved by polysaccharide-based chiral stationary phase (CSP)-HPLC to obtain 25 mg each (2R) and (2S)-o-F-PAT and -o-Cl-5-PAT. Other compounds synthesized herein involve this general process.

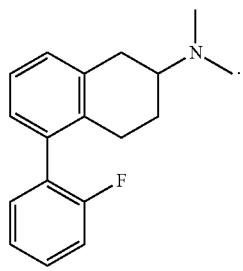 [SMILES: CN(C)C1CCc2c(cccc2-c2ccccc2F)C1]

Characterization of o-F-5-PAT as HCl salt: 1H NMR (500 MHz, $CDCl_3$): δ 12.82 (brs, 1H), 7.36-7.31 (m, 1H), 7.23-7.15 (m, 4H), 7.11-7.07 (m, 2H), 3.56-3.47 (m, 1H), 3.38-3.33 (m, 1H), 3.20 (t, J=12.0 Hz, 1H), 2.84-2.74 (brs, 7H), 2.65-2.56 (m, 1H), 2.38 (dd, J=11.0, 5.0 Hz, 1H), 1.90-1.76

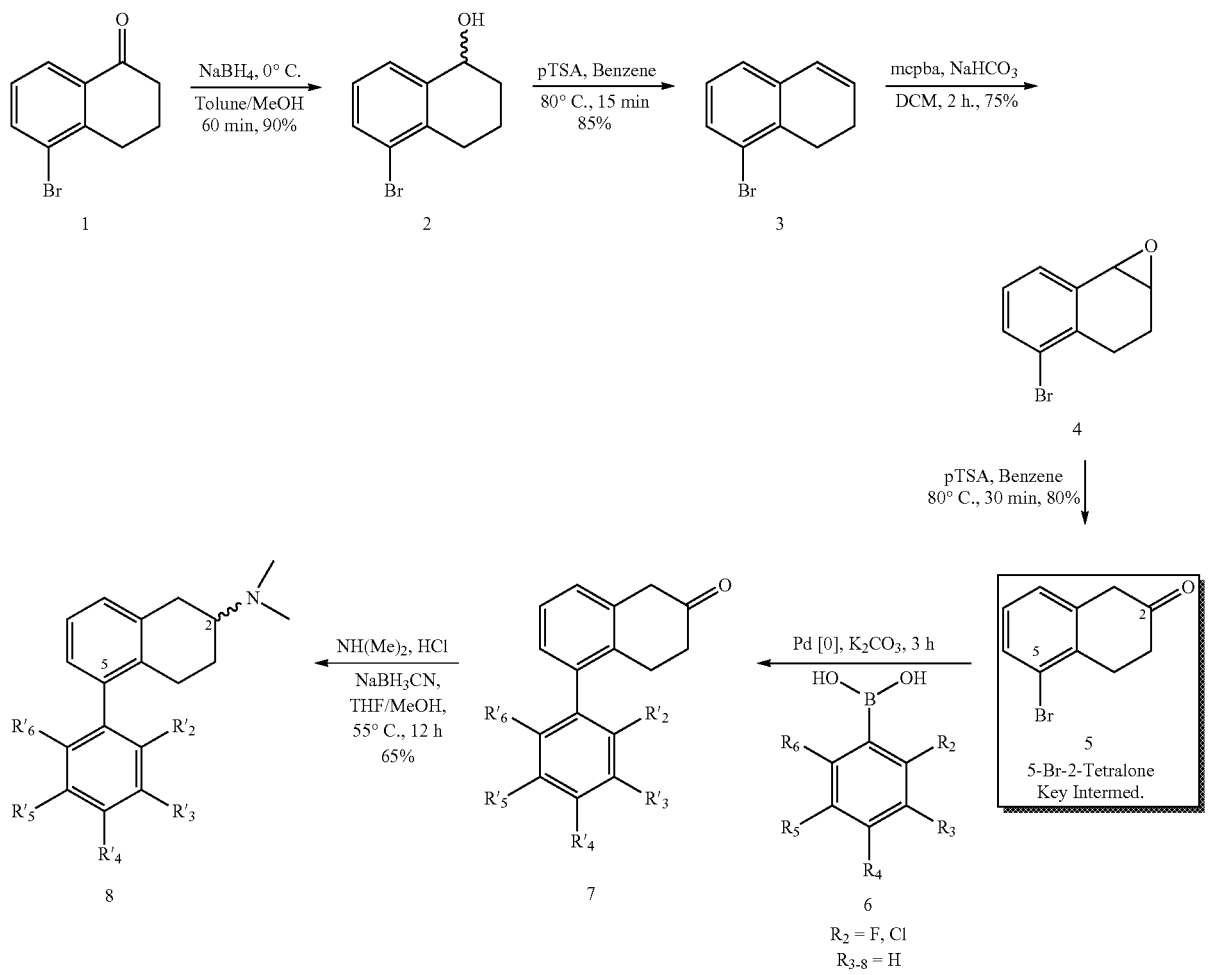

Scheme 1

The following compound, o-F-5-PAT (5-(2'-fluorophenyl)-N,N-dimethyl-1,2,3,4-tetrahydronaphthalen-2-amine) was synthesized:

(m, 1H). M.P: 232-235° C. HPLC (s-prep): solv. sys=EtOH: Hexane (10:90)+0.1% of diethylamine (modifier)+0.1% trifluoroacetic acid (modifier); flow rate=2.0 ml/min. (+)-(2S)- o-F-5-PAT: t=24.2 min [α]²²_D=(+) 5.65° (c 0.32, CH2Cl2). (−)-(2R)-o-F-5-PAT: t=26.5 min. [α]₂₅^D=(−) 5.45° (c 0.22, CH₂Cl₂).

The following compound, o-Cl-5-PAT (5-(2'-chlorophenyl)-N,N-dimethyl-1,2,3,4-tetrahydronaphthalen-2-amine) was synthesized:

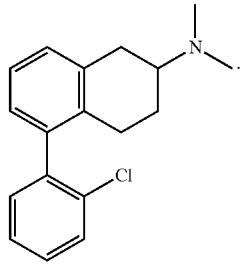 [SMILES: CN(C)C1CCc2c(cccc2-c2ccccc2Cl)C1]

Characterization of o-Cl-5-PAT as HCl salt: 1H NMR: δ 12.56 (brs, 1H), 7.44-7.38 (m, 1H), 7.30-7.27 (m, 2H), 7.21-7.18 (dt, J=7.0, 2.5 Hz, 1H), 7.15-7.10 (m, 2H), 6.99 (t, J=6.0 Hz, 1H), 3.52-3.44 (m, 1H), 3.38-3.33 (m, 1H), 3.18 (t, J=13.5 Hz, 1H), 2.78-2.83 (m, 6H), 2.72-2.45 (m, 2H), 2.34 (dd, J=9.5, 2.0 Hz, 1H), 1.88-1.79 (m, 1H). M. P: 228-230° C. HPLC (same conditions): (+)-(2S)-o-Cl-5-PAT: t=22.4 min [α]₂₅^D=(+) 6.53° (c 0.196, CH₂Cl₂). (−)(2R)-o-Cl-5-PAT: t=25.3 min [α]²¹_D=(−) 6.80° (c 0.42, CH₂Cl₂).

5-(2-furanyl)-N,N-dimethyl-1,2,3,4-tetrahydronaphthalen-2-amine was synthesized

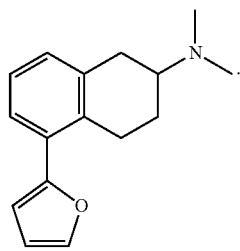 [SMILES: CN(C)C1CCc2c(cccc2-c2ccco2)C1]

5-(2-furanyl)-N,N-dimethyl-1,2,3,4-tetrahydronaphthalen-2-amine was obtained from the corresponding 2-tetralone (0.32 mmol) as yellow oil, yield: 61% (0.046 g); ¹H NMR (500 MHz, CDCl₃): δ_H 1.83-1.91 (m, 1H), 2.56-2.59 (m, 1H), 2.85 (bs, 6H), 2.97-3.04 (m, 2H), 3.14-3.22 (m, 2H), 3.35 (dd, J=15.0, 3.0 Hz, 1H), 3.48-3.56 (m, 1H), 6.47-6.51 (m, 2H) 7.10 (d, 7.5 Hz, 1H), 7.23 (t, 7.5 Hz), 7.5-7.54 (m, 2H).

5-naphthyl-N,N-dimethyl-1,2,3,4-tetrahydronaphthalen-2-amine was synthesized

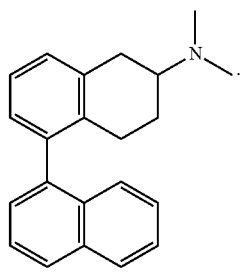 [SMILES: CN(C)C1CCc2c(cccc2-c2cccc3ccccc23)C1]

5-naphthyl-N,N-dimethyl-1,2,3,4-tetrahydronaphthalen-2-amine was obtained from the corresponding 2-tetralone (0.49 mmol) as yellow oil, yield: 71% (0.1 g); ¹H NMR (500 MHz, CDCl₃): δ_H 1.55-1.63 (m, 1H), 1.98-2.07 (m, 1H), 2.32-2.41 (m, 1H), 2.49-2.52 (m, 1H), 2.58 (bs, 6H), 2.97-3.06 (m, 2H), 3.17-3.23 (m, 1H), 7.12 (dd, J=7.5, 6.5 Hz, 1H), 7.21-7.23 (m, 1H), 7.25-7.28 (m, 2H), 7.31 (dd J=6.0, 1.0 Hz, 1H), 7.34-7.4 (m, 1H), 7.44-7.54 (m, 2H), 7.89 (dd, J=18.0, 8.5 Hz, 2H); HPLC (s-prep): solv. sys: MeOH: EtOH (85:15)+0.1% DEA (Modifier), 0.1% TFA (Modifier); flow rate=2.0 mL/min; t₁=16.15 min, t₂=21.05 min.

5-phenyl-N,N-dimethyl-7,8-dimethyoxy-1,2,3,4-tetrahydronaphthalen-2-amine was synthesized

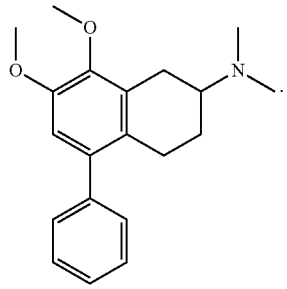

5-phenyl-N,N-dimethyl-7,8-dimethyoxy-1,2,3,4-tetrahydronaphthalen-2-amine was obtained from the corresponding 2-tetralone (0.76 mmol) as colorless solid yield: 49% (0.115 g); ¹H NMR (500 MHz, CDCl₃): δ_H 1.64-1.71 (m, 1H), 2.23 (d, J=11.5 Hz, 1H), 2.69-2.72 (m, 2H), 2.83-2.87 (bs, 7H), 3.36 (dd, J=16, 5 Hz, 1H), 3.44-3.50 (m, 1H), 3.83 (s, 3H), 3.98 (s, 3H), 6.73 (s, 1H), 7.23-7.26 (m, 2H), 7.32-7.36 (m, 1H), 7.38-7.41 (m, 2H); HPLC (s-prep): solv. sys: MeOH: EtOH (85:15)+0.1% TEA (Modifier), 0.1% TFA (Modifier); flow rate=2.0 mL/min; t₁=20.86 min, t₂=24.65 min.

5-(cyclopentyl)-N,N-dimethyl-1,2,3,4-tetrahydronaphthalen-2-amine was synthesized

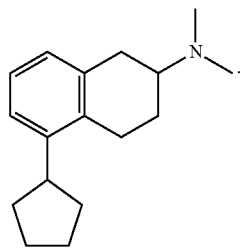 [SMILES: CN(C)C1CCc2c(cccc2C2CCCC2)C1]

5-(cyctopentyl)-N,N-dimethyl-1,2,3,4-tetrahydronaphthalen-2-amine was obtained from the corresponding 2-tetralone (0.16 mmol) as colorless oil, yield: 10% (0.004 g); ¹H NMR (500 MHz, CDCl₃): 1.5-1.59 (m, 2H), 1.66-1.73 (m, 2H), 1.79-1.84 (m, 2H), 1.95-2.05 (m, 2H), 2.43-2.47 (m, 1H), 2.85 (bs, 7H), 3.03-3.14 (m, 2H), 3.16-3.21 (m, 2H), 3.42-3.49 (m, 1H), 6.96 (d, J=7 Hz, 1H), 7.14-7.19 (m, 2H).

5-(isoquinolin-5-yl)-N,N-dimethyl-1,2,3,4-tetrahydronaphthalen-2-amine was synthesized

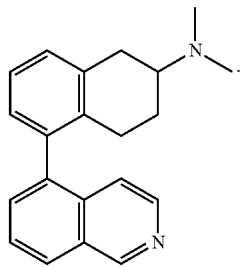 [SMILES: CN(C)C1CCc2c(cccc2-c2cccc3cnccc23)C1]

5-(isoquinolin-5-yl)-N,N-dimethyl-1,2,3,4-tetrahydronaphthalen-2-amine was obtained from the corresponding 2-tetralone (0.16 mmol) as dark red oil, yield: N/A from crude starting material (0.031 g); ¹H NMR (500 MHz, CDCl₃): 1.53-1.61 (m, 1H), 1.99-2.05 (m, 1H), 2.31-2.39 (m, 1H), 2.47 (bs, 6H), 2.81 (bs, 1H), 2.94-3.03 (m, 1H), 3.18 (d, J=15.5 Hz, 1H), 7.1-7.15 (m, 1H), 7.28-7.3 (m, 2H), 7.31-7.53 (m, 1H), 7.63-7.66 (m, 2H), 8.05-8.08 (m, 1H), 8.4 (d, J=19.5 Hz, 1H), 9.29 (s, 1H).

In addition, the boronic acid derivatives in Chart 1 are available to synthesize the corresponding 5-substituted-PAT analogs, according to Scheme 1. Thus analogs are proposed with multiple substitutions to the 5-phenyl moiety, as listed under Hydrogen and Halogen Binding Moieties in Chart 1. Thus, racemic analogs will be synthesized and separated to yield (+)- and (−)-5 (2R)-5-PAT analogs and/or (2R) and (2S)-5-PAT analogs.

Chart 1

Hydrogen and Halogen Binding Moieties | Hydrophobic and Aromatic

-continued
Chart 1
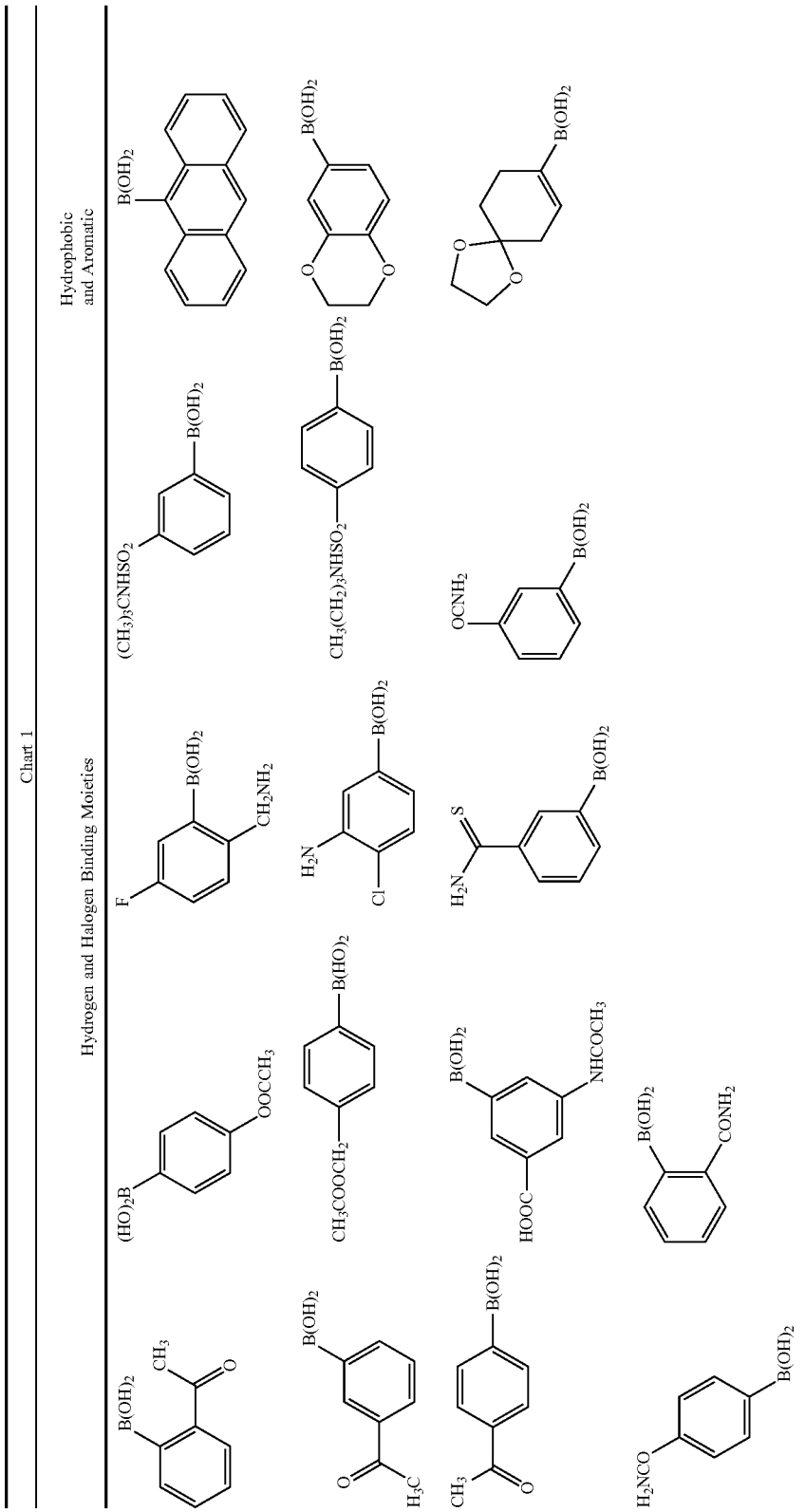

Additional 5-PATs with substitutions to 5-phenyl plus tetrahydronaphthyl moieties (Scheme 2 and Chart 2) are synthesized. These compounds bear substitutions to the 6-, 7-, and/or 8-positions of the tetrahydronaphthyl moiety of the 5-PAT molecular scaffold. Scheme 2 shows the commercially-available phenylbutryic acid (1) starting materials with OCH3 substituents at the indicated ($R_{1-5}$) positions, which undergo reaction with $Br_2$ followed by cyclization with polyphosphoric acid (PPP) to obtain the 5-Br-1-tetralones (3), followed by isomerization to the olefins (4) to obtain the key intermediate 5-Br-2-tetralones (5), that can be further derivatized at the 5-phenyl moiety via the Suzuki coupling reaction of Scheme 1. Chart 2 summarizes the 5-PATs to be obtained with substitutions at both the tetrahydronaphthyl (6,7,8-positions) and 5-phenyl moieties. Such compounds will be chirally resolved.

Scheme 2

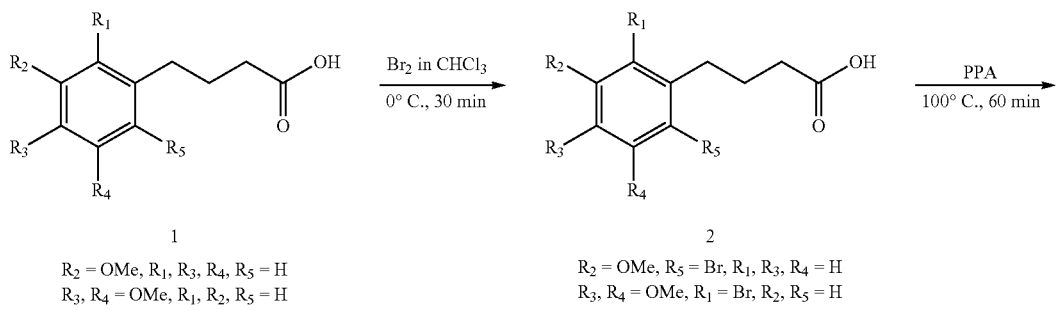

1
$R_2$ = OMe, $R_1$, $R_3$, $R_4$, $R_5$ = H
$R_3$, $R_4$ = OMe, $R_1$, $R_2$, $R_5$ = H

2
$R_2$ = OMe, $R_5$ = Br, $R_1$, $R_3$, $R_4$ = H
$R_3$, $R_4$ = OMe, $R_1$ = Br, $R_2$, $R_5$ = H

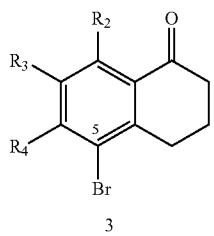

3
5-Br-1-Tetralone
$R_2$ = OMe; $R_3$, $R_4$, = H
$R_3$, $R_4$ = OMe; $R_2$, = H 1. NaBH$_4$, 0° C.  |  2. pTSA,
Tolune/MeOH         |  Benzene, 80° C.,
60 min, 90%         |  15 min, 85%

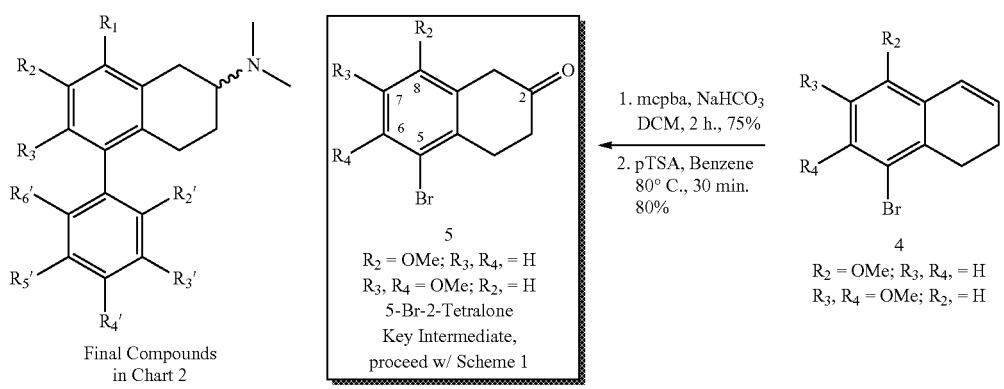

Final Compounds in Chart 2

5
$R_2$ = OMe; $R_3$, $R_4$, = H
$R_3$, $R_4$ = OMe; $R_2$, = H
5-Br-2-Tetralone
Key Intermediate, proceed w/ Scheme 1

1. mcpba, NaHCO$_3$ DCM, 2 h., 75%
2. pTSA, Benzene 80° C., 30 min. 80%

4
$R_2$ = OMe; $R_3$, $R_4$, = H
$R_3$, $R_4$ = OMe; $R_2$, = H

New 5-substituted-2-dimethylaminotetralin analogs (Chart 1) are synthesized. A third series of analogs substitutes the C(5)-phenyl moiety with alternative cycloalkyl, aromatic, or heteroaromatic moieties. To this end, boronic acids listed in Chart 1 with Hydrophobic or Aromatic Moieties are reacted with key intermediate 5-Br-2-tetralone (5), according to Scheme 1. Such compounds will be chirally resolved.

Chart 2

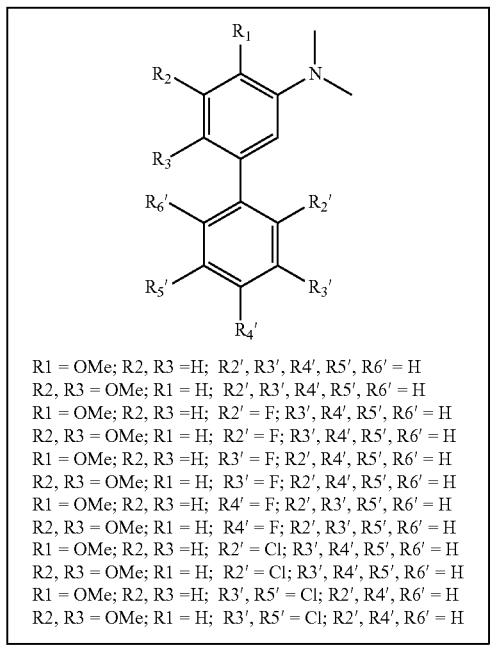

R1 = OMe; R2, R3 =H; R2', R3', R4', R5', R6' = H
R2, R3 = OMe; R1 = H; R2', R3', R4', R5', R6' = H
R1 = OMe; R2, R3 =H; R2' = F; R3', R4', R5', R6' = H
R2, R3 = OMe; R1 = H; R2' = F; R3', R4', R5', R6' = H
R1 = OMe; R2, R3 =H; R3' = F; R2', R4', R5', R6' = H
R2, R3 = OMe; R1 = H; R3' = F; R2', R4', R5', R6' = H
R1 = OMe; R2, R3 =H; R4' = F; R2', R3', R5', R6' = H
R2, R3 = OMe; R1 = H; R4' = F; R2', R3', R5', R6' = H
R1 = OMe; R2, R3 =H; R2' = Cl; R3', R4', R5', R6' = H
R2, R3 = OMe; R1 = H; R2' = Cl; R3', R4', R5', R6' = H
R1 = OMe; R2, R3 =H; R3', R5' = Cl; R2', R4', R6' = H
R2, R3 = OMe; R1 = H; R3', R5' = Cl; R2', R4', R6' = H

5-Pat Biological Examples

Example 2: (+I-5-FPT is a Stereoselective High Affinity 5-HT$_7$ and 5-HT$_{1A}$ Partial Agonist Novel 5-substituted-phenyl-2-dimethylaminotetralin compounds to target 5-HT$_7$ receptors, for example, 5-o-F-PAT and 5-o-Cl-PAT (FIG. 1A), were developed.

Figure 1B:
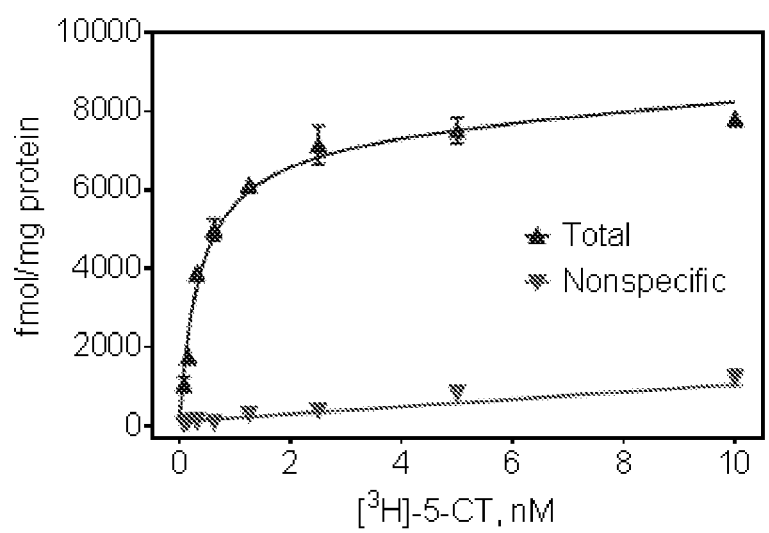
FIG. 1B shows HEK293 cells stably expressing a high density of human 5-HT7a receptors.

HEK293 cells stably expressing human 5-HT$_7$ receptors were generated to assess 5-HT$_7$ pharmacology of 5-FPT enantiomers. Receptor binding site density in the clone with the highest specific binding ("CHTR7 beta") was assessed with [$^3$H]5-CT saturation binding, which revealed a mean (SEM) receptor binding site density, B$_{MAX}$, of 7.7 (0.4) pmol/mg protein (FIG. 1B). At such a high 5-HT$_7$ receptor density, a 5-HT$_7$ partial agonist is not expected to appear as a full agonist, because receptor reserve is not an issue. In addition, 5-FPT pharmacology was evaluated in HEK293 cells transiently over-expressing relevant human 5-HT receptors (5-HT$_{1A, 2A, 2B, 2C}$), and potential 'off-targets', including the dopamine D2, adrenergic $\alpha_{1A, 1B}$, and histamine H$_1$ receptors. Notably, D2 can display high affinity for the 2-aminotetralin scaffold, depending on substitution pattern and stereochemistry, and α1 and H$_1$ receptors are common off-targets of antipsychotics used to treat irritability in ASD. Studies also were conducted using HEK293 cells transiently expressing the mouse 5-HT$_{2A}$ and 5-HT$_{2C}$ receptors, given their relevance to the translational studies.

Figure 3:
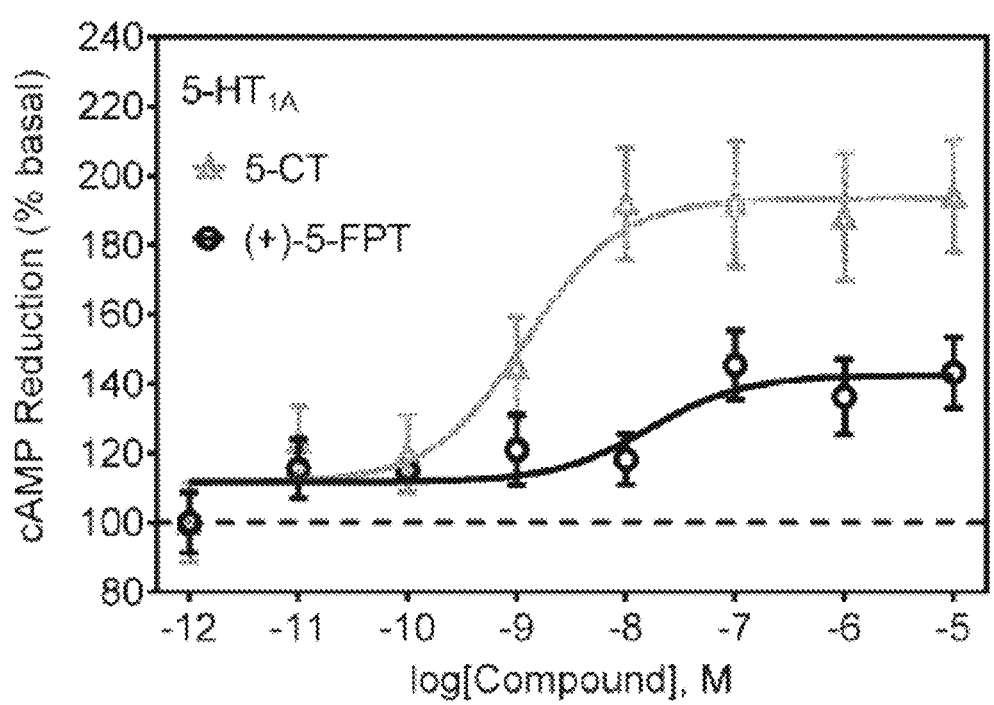
FIG. 3 shows 5-HT$_{1A}$ partial agonist effects of (+)-5-FPT, relative to 5-CT. Representative functional assay results show the mean±SEM of the concentration data points.
Figure 4A:
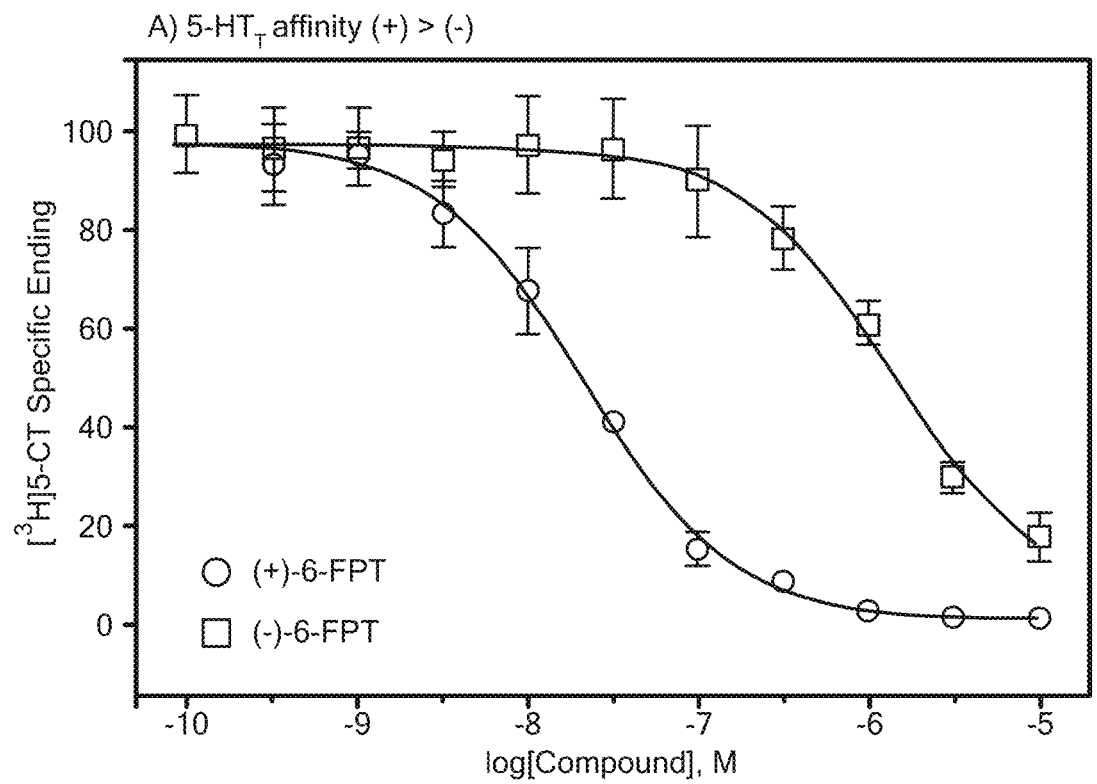
FIGS. 4A-4C show the effects of 5-FPT are stereospecific. Relative to the (−) enantiomer, the (+) enantiomer has higher affinity at 5-HT$_7$ receptors (FIG. 4A) and 5-HT$_{1A}$ receptors (see Table 1), greater potency for activating 5-HT$_7$ receptors (FIG. 4B), and greater potency for reducing (±)-2,5-dimethoxy-4-iodoamphetamine (DOI) (1 mg/kg)-elicited HTR (head-twitch response), (FIG. 4C). The left-hand bar includes data shown in FIG. 7 for comparison. Note, for competition binding shown in FIG. 4A, 2.37 nM (calculated) [$^3$H]5-CT was used to label 5-HT$_7$ receptors, and its K$_D$ was set at 0.7 nM. Data are expressed as the mean±SEM.
Figure 4B:
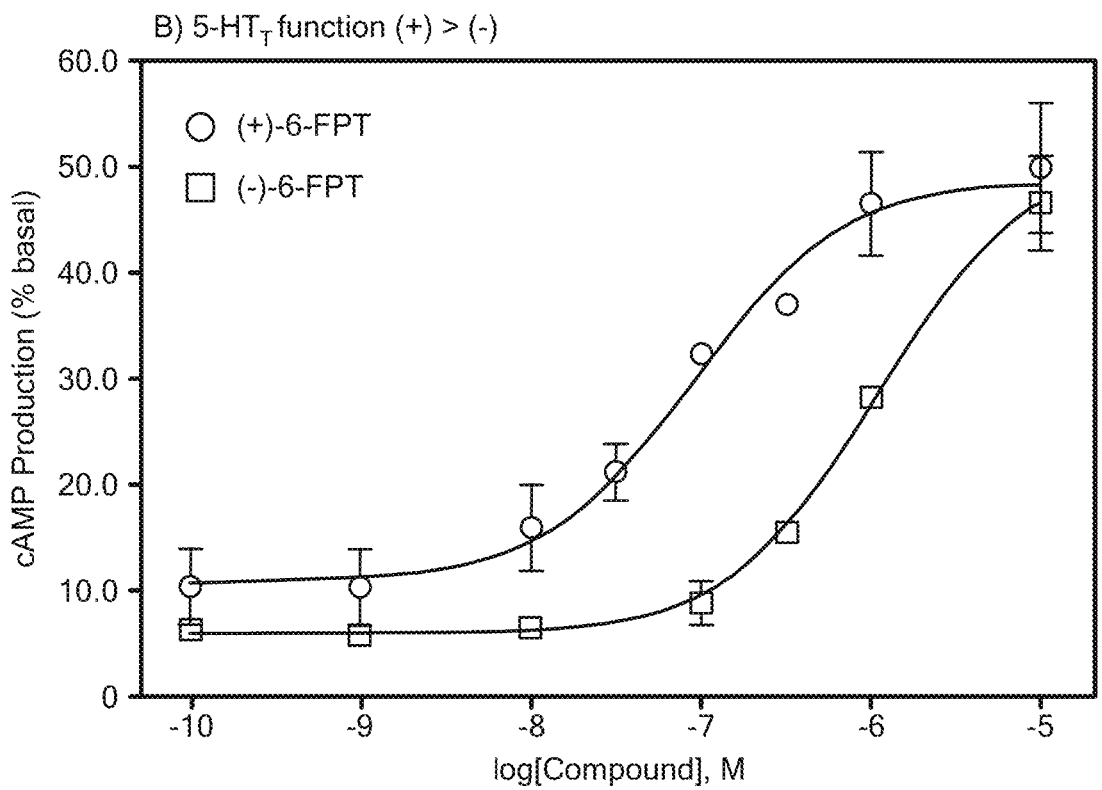
Figure 4C:
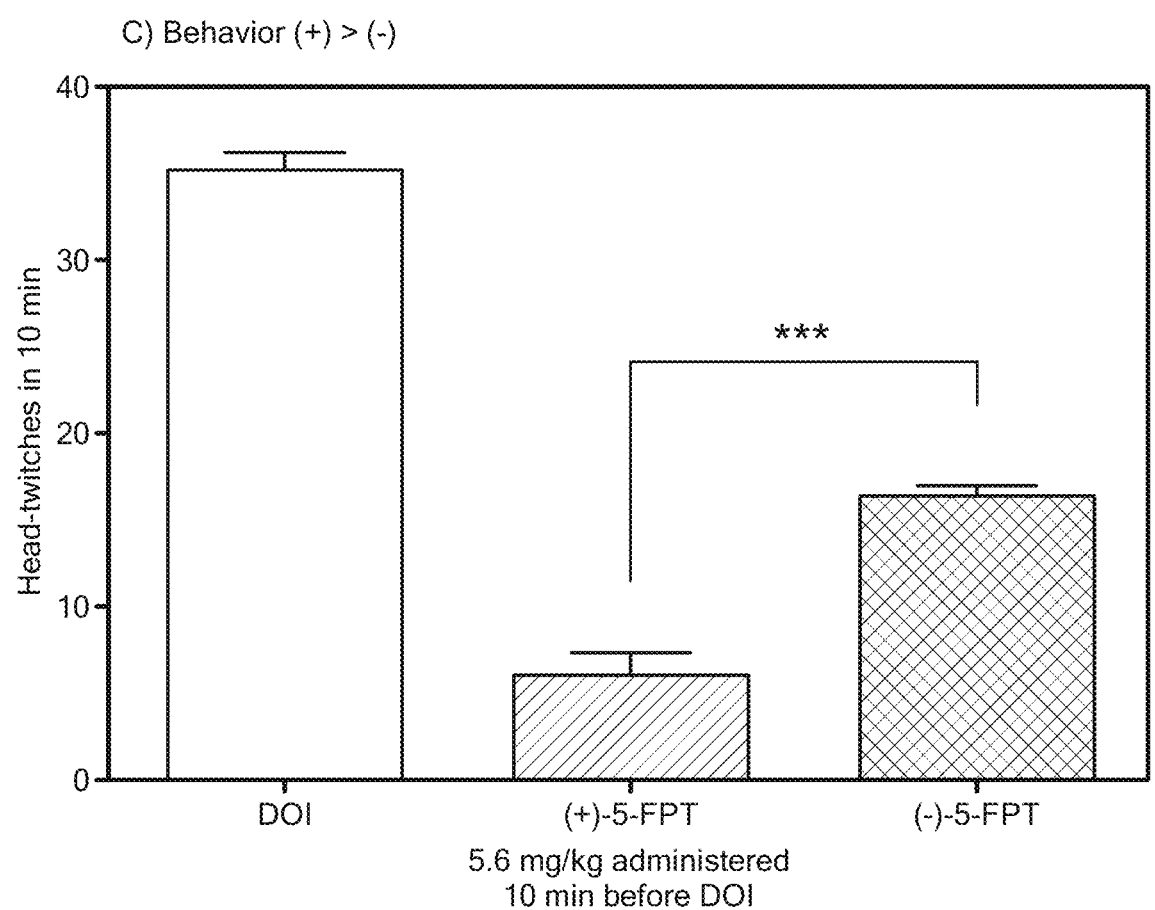
Figure 11:
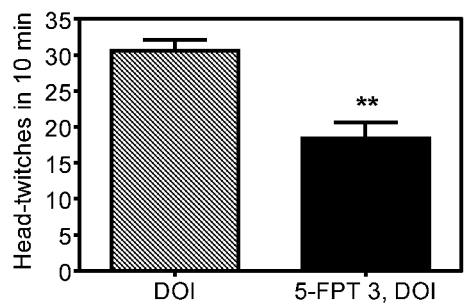
FIG. 11 shows (+)-5-FPT is orally active. Oral gavage administration of 3 mg/kg (+)-5-FPT 10 min prior to subcutaneous administration of 1 mg/kg DOI attenuates the HTR in C57BI/6J mice. Bar graphs show the mean±SEM.

As shown in Table 1, 5-FPT demonstrated high, stereoselective affinity at 5-HT$_7$ receptors, with the (+)-enantiomer (K$_i$=5.8) being about 80-times more potent than the (−)-enantiomer (K$_i$=460 nM). (+)-5-FPT behaved as a 5-HT$_7$ partial agonist regarding Gs-cAMP signaling (EC$_{50}$=34 nM, E$_{MAX}$ vs AS-19=33%) and the (−)-enantiomer also demonstrated partial agonism (EC$_{50}$=378 nM, E$_{MAX}$ vs AS-19=29%) with similar kinetics, albeit, with about 11-times less potency than the (+)-isomer (FIGS. 2A-2B and 11, Table 2). Further in vitro pharmacological studies with 5-FPT revealed that the (+)-enantiomer also had high affinity, partial agonist properties at 5-HT$_{1A}$ receptors (K$_i$=22, EC$_{50}$=40 nM, E$_{MAX}$ vs 5-CT=48%) (Tables 1 and 2, FIG. 3). (−)-5-FPT, however, had no appreciable affinity at 5-HT$_{1A}$ receptors. The striking stereoselective high-affinity of (+) over (−)-5-FPT at 5-HT$_7$ and 5-HT$_{1A}$ receptors indicated subsequent translational studies to assess efficacy to modulate stereotypy in mice should focus on the (+)-enantiomer (see FIG. 4C).

Regarding activity at other 5-HT receptors, as shown in Table 1, (+)-5-FPT affinity at 5-HT$_{2A}$ receptors was very low, and it was a very low potency, partial agonist (Table 2, FIG. 2B). In contrast to 5-HT$_{2A}$ receptors, (+)-5-FPT bound with appreciable affinity at 5-HT$_{2B}$ (K$_i$=60 nM) and 5-HT$_{2C}$ (K$_i$=269 nM) receptors. In functional assays, (+)-5-FPT was devoid of 5-HT$_{2B}$ activity up to 100 μM, suggesting neutral antagonism (Table 2, FIG. 2B). It is noted that 5-HT$_{2B}$ agonist activity is untenable regarding drug development, because it can lead to cardiac valvulopathy. 5-HT$_{2B}$ antagonism, on the other hand, is proving useful to treat attention deficits in persons with FXS, as illustrated by the efficacy of the 5-HT$_{2B}$ antagonist, metadoxine, in clinical trials of adults with attention deficit hyperactivity disorder. At 5-HT$_{2C}$ receptors, (+)-5-FPT was a nearly full-efficacy agonist (Table 2, FIG. 2B), with modest potency (EC$_{50}$=230 nM), consistent with its affinity. At the mouse 5-HT$_{2A}$ receptor, (+)-5-FPT had very low affinity (K$_i$=632 nM), similar to the human receptor, however, its affinity at the mouse 5-HT$_{2C}$ receptor (K$_i$=644 nM) was nearly 2.5-times higher than at the human receptor.

Unexpectedly, it was observed that at mouse and human 5-HT$_{2A}$ receptors, the (−)-5-FPT enantiomer had ~4 and 8-fold higher affinity, respectively, than (+)-5-FPT (Table 1). In functional assays, (−)-5-FPT was a low-potency 5-HT$_7$ and 5-HT$_{2C}$ agonist, but it did not activate 5-HT$_{2A}$ or 5-HT$_{2B}$ receptors up to 100 μM. Neither 5-FPT enantiomer had appreciable affinity at ADFA$_{1A}$, ADRA$_{1B}$, H$_1$, and D$_2$ receptors (i.e. K$_i$>1 μM).

TABLE 1

Affinity values expressed as mean (SEM) K$_i$ nM obtained from at least three independent experiments.

| | 5-HT$_7$ | 5-HT$_{1A}$ | 5-HT$_{2A}$ | 5-HT$_{2B}$ | 5-HT$_{2C}$ | α$_{1A}$ | α$_{1B}$ | H$_1$ | D$_2$ | m5-HT$_{2A}$ | m5-HT$_{2C}$ |
|---|---|---|---|---|---|---|---|---|---|---|---|
| (+)-5-FPT | 5.8(0.7) | 22(2.5) | 886(64) | 60(9) | 269(18) | >10 μM | >10 μM | >1 μM | >1 μM | 632(43) | 644(92) |
| (−)-5-FPT | 460(53) | >1 μM | 119(22) | 684(131) | >1 μM | >10 μM | >10 μM | >1 μM | >1 μM | 147(14) | >1 μM |

All receptors were human, except for m = mouse.
5-HT$_{2C}$ = 5-HT$_{2C-INI}$, m5-HT$_{2C}$ = m5-HT$_{2C-VNV}$, 5-HT$_7$ = 5-HT$_{7a}$.

TABLE 2

Functional activity of (+)-5-FPT at human 5-HT$_7$, 5-HT$_{1A}$, and 5-HT$_2$ receptors.

| | | 5-HT$_7$ | 5-HT$_{1A}$ | 5-HT$_{2A}$ | 5-HT$_{2B}$ | 5-HT$_{2C}$ |
|---|---|---|---|---|---|---|
| (+)-5-FPT | EC$_{50}$ | 34(13) | 40(15) | 3526(826) | Inactive | 230(69) |
| | E$_{MAX}$ | 33(11)% | 48(10)% | 39(4)% | Inactive | 87(13)% |

Data are expressed as mean (SEM) EC$_{50}$, nM, and E$_{MAX}$, % of maximal response, relative to AS-19 (5-HT$_7$), 5-CT (5-HT$_{1A}$), and 5-HT (5-HT$_2$).
Inactive = no activation up to 100 µM.

Figure 5:
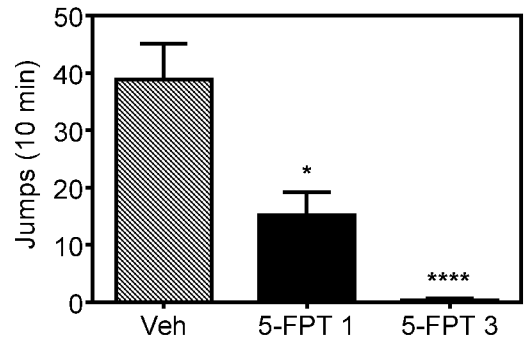
FIG. 5 shows (+)-5-FPT (1 and 3 mg/kg) dose-dependently eliminates idiopathic, stereotypic jumping in C58/J mice. Bar graphs show the mean±SEM.

Example 3: (+)-5-FPT Attenuates Motor Stereotypy without Affecting Locomotion (+)-5-FPT was tested in three, heterogeneous models of stereotypy, each with different scales of validity: 1) idiopathic stereotypic jumping in C58/J mice; 2) (±)-2,5-dimethoxy-4-iodoamphetamine (DOI)-elicited stereotypic head-twitching; 3) and (5P, 10S)-(+)-5-methyl-10,11-dihydro-5H-dibenzo[a,d]cyclohepten-5,10-imine (MK-801)-elicited stereotypic rotations in C57Bl/6J mice. (+)-5-FPT was also tested for efficacy to attenuate d-amphetamine (AMP)-elicited hyperlocomotion in C57Bl/6J mice to assess potential pharmacological utility for psychostimulant abuse. C58/J mice naturally develop repetitive, stereotypic jumping when housed under standard laboratory conditions, and this behavior has been used as a model of stereotypy responsive to drug treatment. As shown in FIG. 5, (+)-5-FPT potently eliminated stereotypic jumping in C58/J mice in a dose-dependent manner, without altering locomotor behavior (see FIG. 8). (+)-5-FPT showed greater efficacy in this model than the recently reported mGluR5 negative allosteric modulator, GRN-529, which was underdevelopment to treat ASD.

Figure 6A:
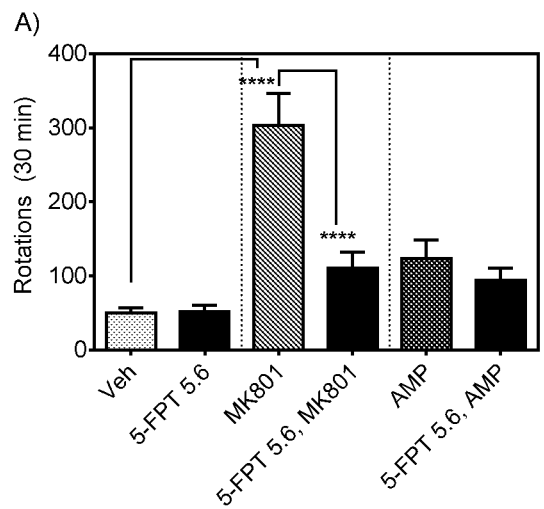
FIG. 6A shows (+)-5-FPT (5.6 mg/kg) significantly reduces stereotypic rotations elicited by MK-801 (0.3 mg/kg) in C57BI/6J mice.
Figure 6B:
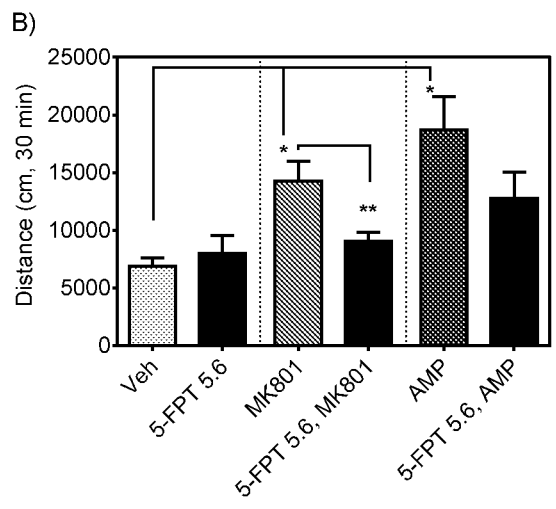
FIG. 6B: (+)-5-FPT, 5.6 mg/kg blocks MK-801 (0.3 mg/kg), but not amphetamine (AMP, 3 mg/kg) hyperlocomotion during a 30 min session. Despite significantly increasing locomotion, AMP does not cause stereotypic rotational behavior. Bar graphs show the mean±SEM.
Figure 8:
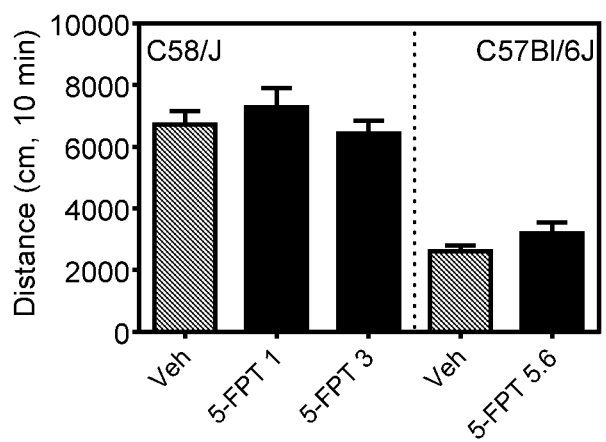
FIG. 8 shows (+)-5-FPT does not alter locomotor behavior. Data are from stereotypy assays using C58/J (left) and C57BI/6J (right) mice. (+)-5-FPT doses were 1, 3, and 5.6 mg/kg. Bar graphs show the mean±SEM.

Regarding glutamate neurotransmission in stereotypy, the NMDA receptor antagonist, MK-801, characteristically elicits stereotypic rotations that appear to mimic monogenetic stereotypy observed in Fmr1 KO mice. Furthermore, mutations and autoantibodies of the NMDA glutamate receptor that decrease its function are causally linked to ASD, intellectual disabilities, and psychiatric symptoms in humans. As shown in FIG. 6A, (+)-5-FPT (5.6 mg/kg) significantly reduced stereotypical rotations in C57Bl/6J mice treated with MK-801. Note, neither (+)-5-FPT nor AMP caused stereotypic rotational behavior (FIG. 6A). Additionally, (+)-5-FPT (5.6 mg/kg) significantly decreased hyperlocomotion caused by MK-801, but did not reduce hyperlocomotion caused by AMP (FIG. 6B). Importantly, on its own, (+)-5-FPT also did not alter locomotion in C57Bl/6J mice (FIG. 6B and FIG. 8).

Figure 7:
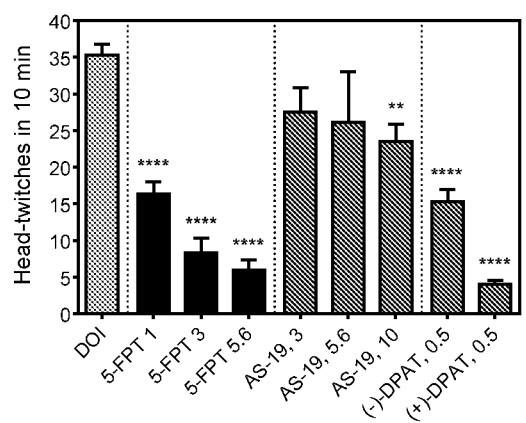
FIG. 7 shows (+)-5-FPT dose-dependently blocks the DOI-elicited HTR in C57BI/6J mice. In comparison, AS-19 (10 mg/kg) attenuated the HTR, and DPAT (0.5 mg/kg) stereoselectively attenuated the HTR. Bar graphs show the mean±SEM.

The DOI-elicited HTR is a behavioral model of cortical 5-HT$_{2A}$ activation, and also has face validity for stereotyped tics. The 5-HT$_{2A}$ receptor is a predominant 5-HT receptor in the cortex, and serves important excitation modulation functions on glutamate pyramidal and GABA neurons. 5-HT$_{2A}$ receptor function in cortical neurons is altered in Fmr1 KO mice, and 5-HT$_{2A}$ function also is disrupted in persons with ASD and Tourette syndrome. Moreover, 5-HT$_{2A}$ antagonists such as ketanserin (tritiated version used here as the 5-HT$_{2A}$ radiolabel) treat tics in Tourette syndrome, and when infused in subthalamic nuclei, reduce stereotypies in rats, supporting the DOI-elicited HTR as a model of stereotypy and/or tics. Relevant, too, the 5-HT$_{1A}$ receptor partial agonist buspirone, in clinical trials to treat children with ASD, has clinically, germane affinity (K$_i$~40 nM) at 5-HT$_{2A}$ receptors. As shown in FIG. 7, (+)-5-FPT dose-dependently attenuated the DOI-elicited HTR, with significant attenuating effects observed with each dose. Notably, DOI has weak affinity at both 5-HT$_{1A}$ and 5-HT$_7$ receptors (Ki>1 µM, our unreported observations), and (+)-5-FPT has weak activity at 5-HT$_{2A}$ receptors, which mediate the DOI-elicited HTR in C57Bl/6J mice, suggesting the effect of (+)-5-FPT was not due to competition with DOI for receptor sites, but was indirectly modulating DOI-elicited 5-HT$_{2A}$ receptor activity to impact behavior. Importantly, although (+)-5-FPT showed weak partial agonist activity at HEK cells over-expressing human 5-HT$_{2A}$ receptors, it did not elicit an HTR on its own (Table 3). To further support the assertion that (+)-5-FPT reduced the DOI HTR via receptor mechanisms other than 5-HT$_{2A}$, tests of (−)-5-FPT, AS-19, (+)-DPAT, and (−)-DPAT in this assay were also conducted. The (−)-5-FPT enantiomer that has the same physicochemical properties as (+)-5-FPT, but substantially higher affinity at human and mouse 5-HT$_{2A}$ receptors, with neutral antagonist function, was substantially less efficacious than (+)-5-FPT at the 5.6 mg/kg dose to reduce the HTR (see FIG. 4C). Furthermore, AS-19 and both enantiomers of DPAT, all of which have weak affinity at 5-HT$_{2A}$, 5-HT$_{2B}$, and 5-HT$_{2C}$ receptors, but, clinically relevant affinity at 5-HT$_7$ and 5-HT$_{1A}$ receptors, suppressed the DOI HTR (FIG. 7). Notably, (+)-DPAT, a 5-HT$_{1A}$ full agonist caused severe hypolocomotion and obvious serotonin syndrome in this assay, whereas neither (−)-DPAT, a 5-HT$_{1A}$ partial agonist, nor AS-19 affected locomotor behavior or caused obvious serotonin syndrome (data not shown). Overall, our results support previous assertions that DPAT, via 5-HT$_{1A}$ activation, suppresses the DOI HTR, and also suggest that 5-HT$_7$ receptor activation may additionally contribute to the effect, which may translate as suppression of stereotyped behaviors. Furthermore, relative to full agonists, 5-HT$_{1A}$ partial agonists appear to translate with fewer untoward effects, such as behaviors associated with serotonin syndrome (see below).

Figure 9:
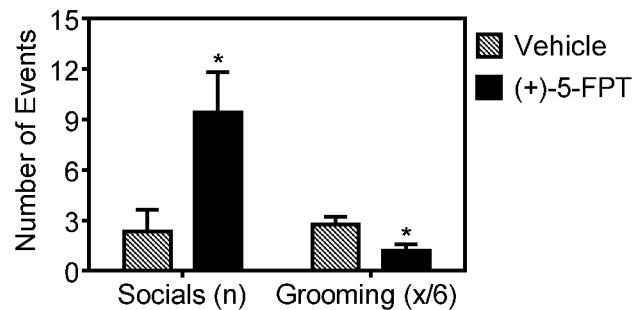
FIG. 9 shows (+)-5-FPT, 5.6 mg/kg, increases social interactions with vehicle-treated littermates, while subsequently decreasing grooming. Shown are mean (SEM) number of social interactions across six, one min. observation sessions, and mean (SEM) number of sessions (out of six) in which mice displayed grooming. Data are from C57BI/6J mice.

Example 4: (+)-5-FPT Increases Social Interactions and does not Cause Symptoms of Serotonin Syndrome As shown in FIG. 9, (+)-5-FPT (5.6 mg/kg) significantly increased the number of initiated social interactions in C57Bl/6J mice, while also decreasing grooming. Furthermore, as shown in Table 3, (+)-5-FPT, at the highest behaviorally-effective dose tested (5.6 mg/kg), did not result in symptoms of serotonin syndrome, including flat body, forepaw treading, moon walking, piloerection, Straub tail, or tremor, but did significantly decrease rearing, suggestive of 5-HT$_{1A}$ activation. Of note, after behavioral testing was complete, blind scorers categorized mice into two groups based on number of rears and initiated social interactions, and the two groups differentiated vehicle from (+)-5-FPT-treated mice with 100% accuracy.

TABLE 3

Test for serotonin syndrome.

| Treatment | Flat Body | Forepaw Tread | Head Weave | HTR (n) | Moon Walk | Pilo-erection | Rears (n) | Straub Tail | Tremor |
|---|---|---|---|---|---|---|---|---|---|
| Vehicle | 0(0) | 0(0) | 0(0) | 1.1(0.5) | 0.1(0.1) | 0(0) | 27(5) | 0(0) | 0(0) |
| (+)-5-FPT, 5.6 mg/kg | 0(0) | 0(0) | 0(0) | 0(0) | 0.3(0.2) | 0(0) | 9(3)**** | 0(0) | 0(0) |

Shown are mean (SEM) number of sessions, from a total of six, one-min. observation sessions, in which mice displayed the behavior (score/6 possible), except for (n) = mean of the total number of responses across all six sessions.

Figure 10:
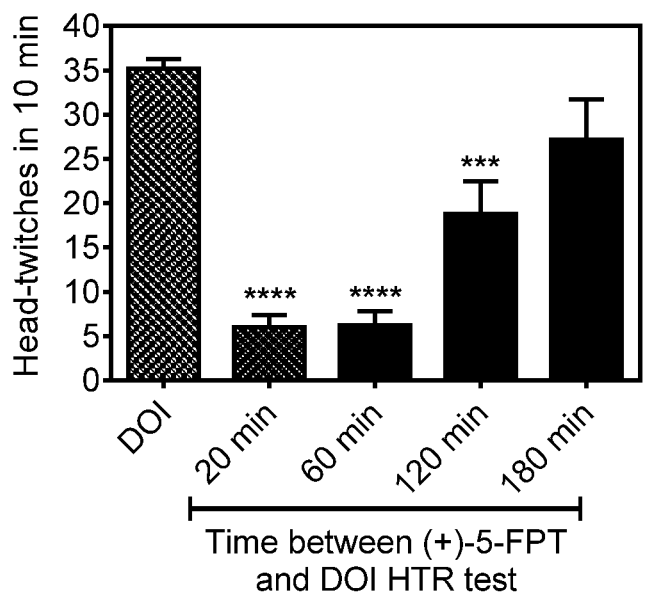
FIG. 10 shows efficacy time course of (+)-5-FPT (5.6 mg/kg). 5-FPT retains efficacy for blocking the DOI (1 mg/kg) HTR when administered 120 min, but not 180 min before testing. Data are from C57BI/6J mice. The two bars at left include data shown in FIG. 7 for comparison. Bar graphs show the mean±SEM.

Example 5: (+)-5-FPT is Orally Active And Readily Crosses the Blood-Brain Barrier As shown in FIGS. 10 and 11, respectively, (+)-5-FPT significantly attenuated the DOI HTR after subcutaneous and oral administration. In addition, (+)-5-FPT readily crosses the blood-brain barrier, as evidenced by detection of μg levels 30, 60, and 90 min after systemic administration (Table 4). Notably, levels of (+)-5-FPT were substantially lower in plasma relative to brain tissue as soon as 30 min post-administration, indicating that (+)-5-FPT is rapidly cleared in the periphery. Meanwhile, the attenuating effects of (+)-5-FPT (5.6 mg/kg) on the DOI HTR remained significant for up to 2 hrs. post-administration; at 3 hrs. post-administration, (+)-5-FPT did not block the DOI HTR.

Given the poor affinity of (+)-5-FPT at $D_2$ receptors, and the observations that (+)-5-FPT (5.6 mg/kg) did not significantly decrease hyperlocomotion elicited by amphetamine, and without wishing to be bound by theory, (+)-5-FPT may not be working directly through dopaminergic mechanisms. Because of (+)-5-FPT's high affinity at $5\text{-}HT_{1A}$ and $5\text{-}HT_7$ receptors, and because (+)-5-FPT considerably affected behavior elicited by MK-801 and DOI, without wishing to be bound by theory, (+J-5-FPT may work in vivo via $5\text{-}HT_{1A}$ and $5\text{-}HT_7$ partial agonism mechanisms that regulates glutamatergic and/or $5\text{-}HT_2$ receptor signaling.

TABLE 4

Plasma and brain concentrations of (+)-5-FPT after 3.0 mg/kg subcutaneous administration. Data are expressed as mean (SEM).

| | Time after injection | | |
|---|---|---|---|
| | 30 min | 60 min | 90 min |
| Plasma (μg/mL) | 0.114(0.03) | 0.118(0.01) | 0.070(1.01) |
| Brain (μg/g) | 1.78(0.24) | 2.16(0.17) | 1.46(0.09) |

Example 6: Survey of 5-PAT Activity at Serotonin Receptors

FIG. 12 shows various synthesized 5-PAT compounds and their affinities at serotonin receptor types, $5\text{-}HT_{1A}$, $5\text{-}HT_{2A}$, $5\text{-}HT_{2B}$, $5\text{-}HT_{2C}$, and $5\text{-}HT_7$. Also included are affinities at histamine H1 receptor.

In FIG. 12, "+" and "−" indicate enantiomers. Further, the compounds are defined in reference to the following general structures:

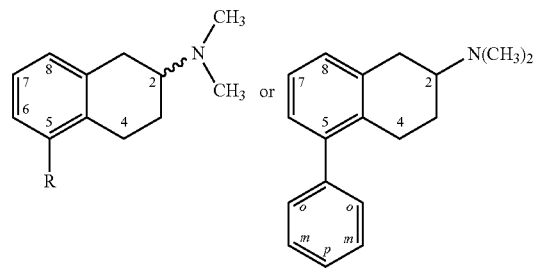

In which, when R is an unsubstituted phenyl ring, the compound is "5-PAT." Substituents to the phenyl ring are indicated by the ortho ("0"), meta ("m"), and para ("p") designations. The designation "di" means two substituents. Further, R is also rings other than phenyl, as indicated in FIG. 12 (e.g. isoquinoline, naphthalene, 2 Furanyl, cyclopentyl, etc.).

4-PAT Synthetic Examples

Example 7: 4-PAT Synthesis

Synthesis of compounds of Formula IIa as described herein is shown in Scheme 1. Generally, reaction of 2-, 3-, 4-, 2,6-, or 3,5-substituted styrene with TFAA provides the tetralen-2-ol phenyl acetate that is reduced to the tetral-2-ol, followed by tosylation and SN2 inversion with dimethylamine. The cis/trans racemates are separated by column chromatography and enantiomer resolution is by chiral stationary phase (CSP)-HPLC.

Scheme 1

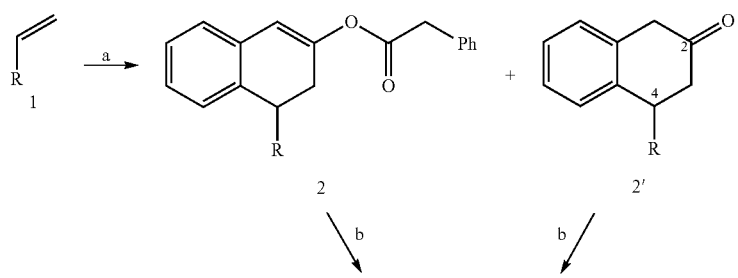

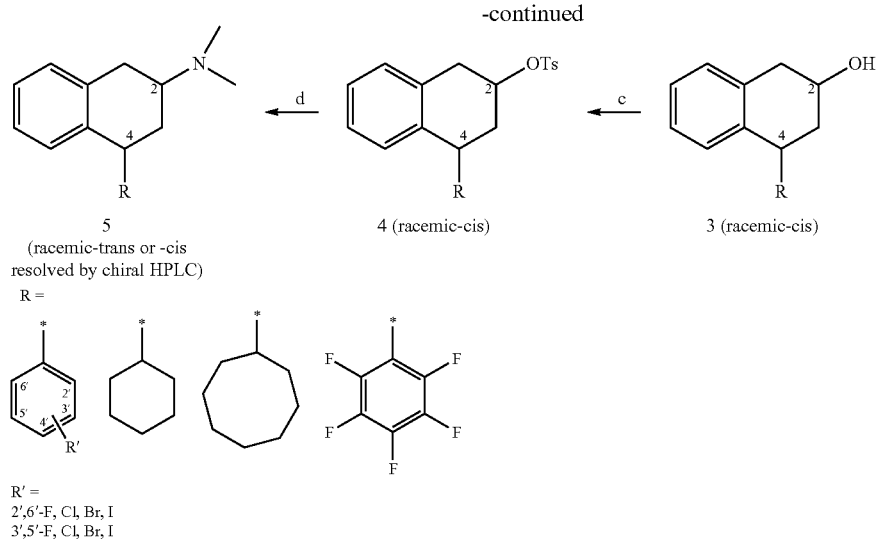

5 (racemic-trans or -cis resolved by chiral HPLC)

R =

R' =
2',6'-F, Cl, Br, I
3',5'-F, Cl, Br, I

In step a, phenyl acetic acid (3 eq.) was reacted with TFAA (3 eq.) at 0° C.-room temperature for 24 hours or for 0.5 hours for 2'a-b. In step b, NaBH4/MeOH was added at 50° C. for 15 hours. In step c, TsCl/pyridine was added at room temperature for 20 hours. In step d., aqueous NMe2 was added, the tube was sealed, and left at 80° C. for 24 hours.

Synthesis of compounds of Formula II as described herein is shown in Schemes 2 and 3 (see Table 5 above for naming of compounds).

Scheme 2 shows the synthetic route to obtain 4-aryl-N,N-dimethy-6,7-substituted-tetrahydronaphthalene-2-amines (7a-l). Either, 4-methoxyphenyl acetic acid (2a) or 2-(3-chloro-4-methoxyphenyl) acetic acid (2b), was reacted with the 3'-halogenated styrene via a cascade trifluoroacetic anhydride (TFM)-mediated carbonyl-ene reaction followed by tandem Friedel-Craft cyclization and O-acylation procedure to give 4-(3'-Cl or Br- phenyl)-6-methoxy-7-(H or Cl)-3,4-dihydronaphthalene-2-yl phenylacetates, 3a-c. The phenylacetates (3a-c) were reduced to yield cis-tetralols (4a-c) as the major products (≥97%), as deduced from $^1$H NMR spectra and TLC, thus, the reaction could be considered as stereospecific. Assignment of cis and trans geometry was based on comparison of $^1$H NMR data. Specifically, for the trans-isomer, the C(4) proton spectrum appeared as a triplet due to greater de-shielding in comparison to the cis-isomer, wherein, the C(4) proton spectrum appeared as a double doublet. Without removal of trace trans-diastereomers, the predominant cis-tetralols (4a-c) were used in the subsequent reactions. A batch of tetralols 4a was debrominated to afford 5a. Trans-tetralols (6a-b) were prepared from 5a or 4b using Mitsunobu reaction conditions. Tosylation of the tetralols (4a-c, 5a, 6a-b) proceeded smoothly and the tosylates were immediately treated with aqueous dimethylamine in a sealed tube to afford the racemic cis or trans tetrahydronaphthalen-2-dimethylamines (7a-l). In all the cases, the crude dimethylaminotetralin was collected as a single cis- or trans-diastereomer confirmed by comparison of the characteristic $^1$H-NMR signals (e.g., 7a: H-4 proton δ=4.49, bs; 7c: H-4 proton=4.17, dd). A polysaccaharide-based chiral stationary-phase preparative HPLC system was used to separate the (+) and (−)-enantiomers (7a-l). In previous studies, the absolute configuration of a related compound were determined by X-ray crystallography to have the (2S, 4R) absolute configuration. In this study, the (−)-trans analogs (7b, f, j, l, n) had a longer chiral elution time compared to their corresponding (+)-trans isomers.

Scheme 2

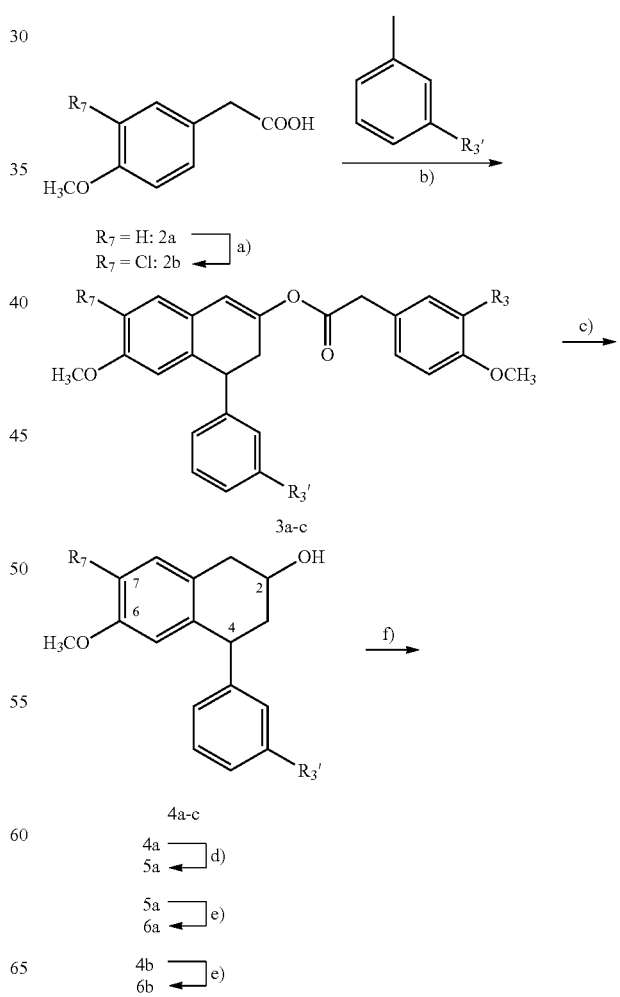

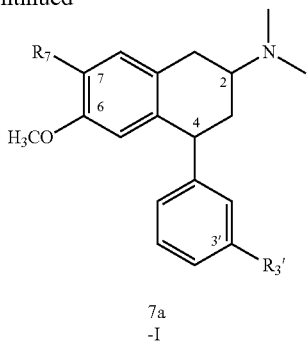

7a
-I

Scheme 3 outlines the preparation of the (+) or (−)-trans-4-phenyl-N,N,-dimethyl-6-hydroxy-7-chloro-tetrahydronaphthalene-2-amine (7m or 7n). The previously obtained analog 7a or 7b was reacted with 48% aqueous hydrobromide solution at reflux temperature for 3 hours respectively, followed by column chromatography purification. The absolute configuration of 7m was assigned as (2R, 4S) and 7n was assigned as (2S, 4R).

Scheme 3

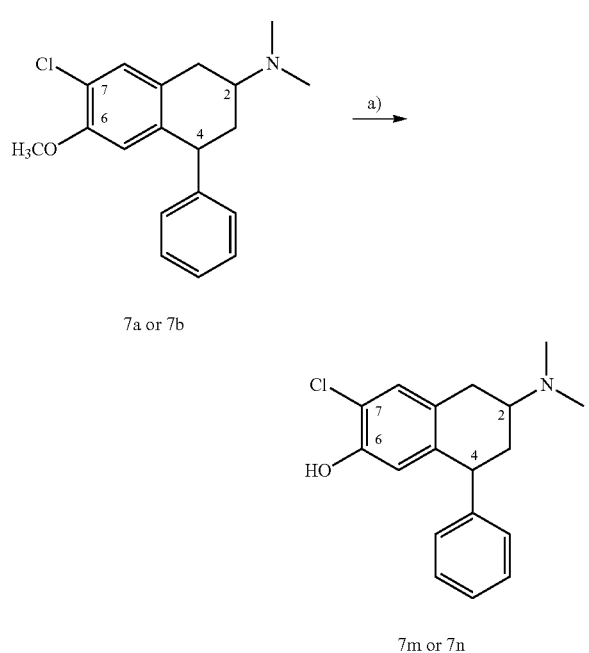

7a or 7b 7m or 7n

Preparation of 2-(3-chloro-4-methoxyphenyl) acetic acid (2b). To a solution of 4-methoxyphenyl acetic acid 2a (1 g, 6.0 mmol) in 10 mL acetone was added oxone (3.7 g, 6.0 mmol). The suspension was stirred at r.t. for 15 min and then aqueous NaCl (1.4 g in 10 mL) was added. Stirring continued for another 6 h and then the mixture was evaporated in vacuo. The residue was diluted in water and extracted with ethyl acetate. The organic layer was washed with brine, dried over $Na_2SO_4$, and concentrated under reduced pressure. The crude product was purified by recrystallization (toluene:hexane=1:9) and collected as a white needle-like solid (50% yield). $^1$H-NMR (400 MHz, $CDCl_3$): δ 7.3 (d, J=1.6 Hz, 1H), 7.13 (dd, J=8.0, 2.0 Hz, 1H) 6.88 (d, J=8.8 Hz, 1H) 3.89 (s, 3H), 3.57 (s, 2H). $^{13}$C NMR (100 MHz, $CDCl_3$) δ 39.7, 56.1, 112.1, 122.4, 126.1, 128.7, 131.1, 154.3, 177.7.

General procedure for the preparation of enol-ester 3a-c. Either 4-methoxyphenyl acetic acid (2a) or 2-(3-chloro-4-methoxyphenyl) acetic acid (2b) (9 mmol) was dissolved in trifluoroacetic anhydride (TFAA) (9.5 mmol) at room temperature under $N_2$ atm to generate the mixed anhydride, that was subsequently transferred using a double ended needle to another flask containing the appropriate 3'-halogenated styrene (3 mmol) at 0° C. The reaction mixture was stirred at room temperature overnight and then quenched with deionized water and extracted with ethyl acetate. The organic layers were washed with saturated $NaHO_3$ solution, dried over $Na_2SO_4$, filtered, and then concentrated under reduced pressure. Crude products were purified by column chromatography (hexane: ethyl acetate=20:1) to afford the product as colorless thick oils. The yields were calculated based on the styrene used in the reaction.

4-(3'-Bromophenyl)-7-chloro-6-methoxy-3,4-dihydronaphthalen-2-yl 2-(3-chloro-4-methoxyphenyl)acetate (3a). 3a was prepared from 2b and 3'-bromostyrene as a colorless oil. Yield: 70%; $^1$H-NMR (400 MHz, $CDCl_3$): δ 7.30-7.25 (m, 3H), 7.16-7.15 (m, 1H), 7.07-7.05 (d, J=8.6 Hz, 1H), 6.94-6.91 (m, 2H) 6.76-6.740 (dd, J=8.3 Hz, 2.8 Hz, 1H), 6.40-6.39 (d, J=2.4 Hz, 1H), 6.31 (s, 1H), 4.3-4.27 (t, J=8.9 Hz, 1H), 3.84 (s, 3H), 3.73 (s, 3H), 3.70 (s, 2H), 2.79-2.77 (m, 2H).

4-(3'-chlorophenyl)-6-methoxy-3,4-dihydronaphthalen-2-yl 2-(3-chloro-4-methoxyphenyl)acetate (3b). 3b was prepared from 2b and 3'-chlorostyrene as a colorless oil. Yield: 65%; $^1$H-NMR (400 MHz, $CDCl_3$): δ 7.29-7.24 (m, 3H), 7.15-7.14 (m, 1H), 7.06-7.04 (d, J=8.4 Hz, 1H), 6.92-6.91 (m, 2H) 6.76-6.74 (dd, J=8.0 Hz, 2.7 Hz, 1H), 6.40-6.39 (d, J=2.4 Hz, 1H), 6.29 (s, 1H), 4.3-4.27 (t, J=9.1 Hz, 1H), 3.84 (s, 3H), 3.73 (s, 3H), 3.69 (s, 2H), 2.74-2.70 (m, 2H).

4-(3'-Chlorophenyl)-6-methoxy-3,4-dihydronaphthalen-2-yl 2-(4-methoxyphenyl)acetate (3c). 3c was prepared from 2a and 3'-chlorostyrene as a colorless oil. Yield: 73%; $^1$H-NMR (400 MHz, $CDCl_3$): δ 7.30-6.34 (m, 11H), 6.25 (s, 1H), 4.24 (t, J=8.8 Hz, 1H), 3.80 (s, 3H), 3.72 (s, 3H), 3.69 (s, 2H), 2.65 (m, 2H).

General procedure for preparation of substituted cis-tetralols (4a-c). The enol ester 3a-c (4.7 mmol) was dissolved in MeOH (35 ml) and the solution was cooled to 0° C., followed by addition over 5 min of $NaBH_4$ (16 mmol). The reaction was kept at 0° C. for another 30 min, then the mixture was allowed to warm to room temperature, before being heated and stirred at 55° C. for 10 h. The reaction was quenched by water (25 mL), extracted with $CH_2Cl_2$, and dried over $Na_2SO_4$. The crude products were purified using silica-gel column chromatography (MeOH: $CH_2Cl_2$=1:50).

Cis-4-(3'-Bromophenyl)-7-chloro-6-methoxy-1,2,3,4-tetrahydronaphthalen-2-ol (4a). 4a was prepared from 3a as a thick oil. Yield: 70%; $^1$H-NMR (400 MHz, $CDCl_3$): δ 7.29-7.0 (m, 5H), 6.24 (s, 1H), 4.13-4.08 (m, 2H, H-2 & H-4), 3.69 (s, 3H) 3.13 (dd, J=16.4, 4.8 Hz, 1H), 2.75 (dd, J=16.2, 6.2 Hz, 1H), 2.24-2.17 (m, 1H), 1.78 (dd, J=23.8, 12.2 Hz, 1H).

Cis-7-Chloro-4-(3'-chlorophenyl)-6-methoxy-1,2,3,4-tetrahydronaphthalen-2-ol (4b). 4b was prepared from 3b as a thick oil. Yield: 72%; $^1$H-NMR (400 MHz, $CDCl_3$): δ 7.28-7.01 (m, 5H), 6.27 (s, 1H), 4.16-4.07 (m, 2H, H-2 & H-4), 3.62 (s, 3H) 3.08 (dd, J=16.4, 4.2 Hz, 1H), 2.79 (dd, J=16.5, 6.0 Hz, 1H), 2.38 (m, 1H), 1.8 (dd, J=23.6, 12.2 Hz, 1H).

Cis-4-(3-chlorophenyl)-6-methoxy-1,2,3,4-tetrahydronaphthalen-2-ol (4c). 4c was prepared from 3c as a thick oil. Yield: 75%; $^1$H-NMR (400 MHz, CDCl$_3$): δ 7.3-7.1 (m, 4H), 6.73 (m, 1H), 6.26 (s, 1H), 4.14-4.07 (m, 2H, H-2 & H-4), 3.67 (s, 3H), 3.13 (dd, J=17.3, 5.2 Hz, 1H), 2.82 (dd, J=17.1, 7.6 Hz, 1H), 2.37 (m, 1H), 1.83 (dd, J=22.8, 11.9 Hz, 1H).

Cis-7-chloro-6-methoxy-4-phenyl-1,2,3,4-tetrahydronaphthalen-2-ol (5a). To a solution of 4a (0.46 mmol) dissolved in MeOH (5 mL) was added palladium/charcoal (5.1 mg) or palladium acetate and triethylamine (80 μL). The mixture was stirred at room temperature in a hydrogen balloon for 2 h. After filtration, the solvent was evaporated in vacuo. Compound 5a was obtained as an oil. Yield: 98%; $^1$H-NMR (400 MHz, CDCl$_3$): δ 7.40-6.82 (m, 6H), 6.21 (s, 1H), 4.2-4.02 (m, 2H), 3.6 (s, 3H), 3.14-3.04 (dd, J=16.4, 4.8 Hz, 1H), 2.82-2.77 (m, 1H), 2.39 (m, 1H), 1.8 (q, J=23.4, 11.8 Hz, 1H).

General procedure for preparation of substituted trans-tetralols (6a-b). To a solution of cis-2-tetralol 5a or 4b (1.9 mmol) dissolved in dry THF (25 mL), was added triphenylphosphine (3.8 mmol) and benzoic acid (3.8 mmol). Then, diisopropyl azodicarboxylate (DIAD)(3.8 mmol) was added drop-wise. The mixture was stirred at room temperature overnight, and then the solvent was evaporated under reduced pressure. The crude product was purified by silica gel column chromatography (toluene) and then mixed with ethanol (45 mL) and NaOH solution (1N in methanol, 3.6 mL) and stirred at room temperature overnight. Following evaporation of the solvent in vacuo, the crude product was purified by silica gel column chromatography (CH$_2$Cl$_2$:MeOH=97:3).

Trans-7-Chloro-6-methoxy-4-phenyl-1,2,3,4-tetrahydronaphthalen-2-ol (6a). 6a was prepared from 5a as a thick colorless oil. Yield: 35%; $^1$H-NMR (400 MHz, CDCl$_3$): δ 7.35-7.02 (m, 6H), 6.41 (s, 1H), 4.3 (t, J=7.2 Hz. 1H), 4.28-4.15 (m, 1H), 3.6 (s, 3H), 3.14-3.10 (m, 1H), 2.79-2.72 (m, 1H), 2.21-2.17 (m, 1H), 2.04-1.98 (m, 1H).

Trans-7-Chloro-4-(3-chlorophenyl)-6-methoxy-1,2,3,4-tetrahydronaphthalen-2-ol (6b). 6b was prepared from 4b as a colorless thick oil. Yield: 42%; $^1$H-NMR (400 MHz, CDCl$_3$): δ 7.4-7.0 (m, 5H), 6.41 (s, 1H), 4.3 (m, 1H, H-4), 4.21 (m, 1H), 3.6 (s, 3H), 3.23-3.12 (m, 1H), 2.91-2.69 (m, 1H), 2.21-2.17 (m, 1H), 2.04-1.98 (m, 1H).

General procedure for preparation of substituted-N,N-dimethyl-1,2,3,4-tetrahydronaphthalen-2-amines 7a-l: The 2-tetralol 4a-c, 5a, or 6a-b (1.0 mmol) was dissolved in pyridine (7 mL) and p-toluenesulfonyl chloride (2.1 mmol) was added slowly. The mixture was stirred at room temperature for 20 hours and then the reaction was quenched by ice/water and extracted with ethyl acetate. The organic layer was dried over Na$_2$SO$_4$ and the crude product was purified by silica gel column chromatography (hexane:ethyl acetate=9:1). Immediately, the tosylated intermediate was transferred into a thick-wall flask and mixed with dimethylamine (40% in H$_2$O, 4 mL) and sealed. The mixture was stirred at 80° C. overnight. After cooling, the reaction mixture was extracted with CH$_2$Cl$_2$, and the crude product was washed with water and dried over Na$_2$SO$_4$. The crude product was purified by silica gel column chromatography (MeOH: CH$_2$Cl$_2$=1:19) to afford racemic N,N-dimethyltetrahydronaphthalen-2-amine (7a-l) that was resolved using semi-preparative chiral stationary-phase (polysaccharide-based) preparative HPLC, with a combination of solvents and modifier unique for each analog (detailed below) to elute the (+)- and (−)-enantiomer at retention time h at V respectively. The eluents containing the desired (+) or (−)-N,N-dimethyltetrahydronaphthalene-2-amine product (7a-l) were combined and concentrated under reduced pressure to afford a colorless oil. The oil was partitioned between CH$_2$Cl$_2$ and water (H$_2$O was added in first), extracted with CH$_2$Cl$_2$, dried over Na$_2$SO$_4$, and solvent was evaporated in vacuo to afford the 7a-l product for spectral characterization. The free base 7a-l was dissolved in ether/ethylacetate through which HCl gas was passed to obtain the HCl salt for use in pharmacological studies.

Trans-4-Phenyl-6-methoxy-7-chloro-N,N-dimethyl-1,2,3,4-tetrahydronaphthalen-2-amine (7a-b). 7a-b was prepared from 5a as a hygroscopic solid. Yield: 37%; $^1$H-NMR (400 MHz, CDCl$_3$): δ 7.32-7.14 (m, 4H), 6.93 (d, J=7.8 Hz, 2H), 6.54 (s, 1H), 4.49 (bs, 1H, H-4), 3.76 (s, 3H), 3.27-3.21 (m, 1H), 3.08-2.98 (m, 2H), 2.72 (s, 6H), 2.41-2.30 (m, 2H). $^{13}$C NMR (100 MHz, CDCl$_3$): δ 29.3, 31.8, 42.2, 43.7, 56.1, 58.0, 112.9, 121.8, 125.6, 127.1, 128.1, 128.5, 128.8, 130.6, 135.2, 143.9, 154.0, 162.6. HRMS: Calcd. for C$_{19}$H$_{23}$ClNO: 316.1468, 318.1439 [M+H]$^+$; Found: 316.1463, 318.1440; isotope pattern confirmed. HPLC (s-prep): solv. sys=EtOH: Hexane (8:92)+0.1% of diethylamine (modifier)+0.1% trifluoroacetic acid (modifier); flow rate=4 mL/min. 7a. [α]$^{25}_D$=(+) 42° (c 1.0, CH$_2$Cl$_2$), t$_1$=13.06 min. 7b. [α]$^{25}_D$= (−) 46° (c 1.0, CH$_2$Cl$_2$), t$_2$=14.6 min.

Cis-4-Phenyl-6-methoxy-7-chloro-N,N-dimethyl-1,2,3,4-tetrahydronaphthalen-2-amine (7c-d). 7c-d was prepared from 6a as a hygroscopic solid. Yield 29%; $^1$H-NMR (400 MHz, CDCl$_3$): δ 7.36-7.15 (m, 6H), 6.28 (s, 1H), 4.17 (dd, J=12.0, 4.8 Hz, 1H, H-4), 3.59 (s, 3H), 3.19-3.07 (m, 2H), 2.85 (s, 6H), 2.52 (dd, J=8.0, 2.0 Hz, 1H), 2.32 (t, J=7.6 Hz, 1H), 1.92 (dd, J=24.0, 12.0 Hz, 1H). $^{13}$C NMR (100 MHz, CDCl$_3$): δ 34.3, 39.2, 40.3, 46.0, 56.0, 61.1, 112.6, 121.3, 124.9, 127.4, 128.5, 129.0, 130.4, 137.5, 143.8, 153.8, 162.7, 163.1. HRMS Calcd. for C$_{19}$H$_{23}$ClNO: 316.1463, 318.1439 [M+H]$^+$; Found 316.1468, 318.1440; isotope pattern confirmed. HPLC (s-prep): solv. sys=EtOH: Hexane (8:92)+0.1% of diethylamine (modifier)+0.1% trifluoroacetic acid (modifier); flow rate=4 mL/min. 7c. [α]$^{25}_D$=(+) 111° (c 1.0, CH$_2$Cl$_2$), t$_1$=12.8 min. 7d. [α]$^{25}_D$=(−) 98° (c 1.0, CH$_2$Cl$_2$). t$_2$=14.6 min.

Trans-4-(3'-Chlorophenyi)-6-methoxy-7-chloro-N,N-dimethyl-1,2,3,4-tetrahydronaphthalen-2-amine (7e-f). 7e-f was prepared from 4b as a hygroscopic solid. Yield: 41%; $^1$H-NMR (400 MHz, CDCl$_3$): δ 7.38-7.20 (m, 3H), 6.92 (s, 1H), 6.85-6.73 (m, 1H), 6.54 (s, 1H), 4.42 (bs, 1H, H-4), 3.79 (s, 3H), 3.34-3.21 (m, 2H), 3.10-2.98 (m, 1H), 2.75 (s, 6H), 2.40-2.35 (m, 2H). $^{13}$C NMR (100 MHz, CDCl$_3$): δ 29.1, 31.8, 42.2, 43.4, 56.2, 57.9, 112.8, 122.1, 125.5, 126.4, 127.4, 128.2, 130.1, 130.7, 134.3, 134.8, 146.0, 154.1. HRMS Calcd. for C19H22Cl$_2$NO: 350.1078, 352.1049 [M+H]$^+$; Found: 350.1073, 352.1047; isotope pattern confirmed. HPLC (s-prep): solv. sys=EtOH:Hexane (8:92)+0.1% of diethylamine (modifier)+0.1% trifluoroacetic acid (modifier); flow rate=4 mL/min. 7e. [α]$^{25}_D$=(+) 14° (c 1.0, CH$_2$Cl$_2$), t$_1$=12.2 min. 7f. [α]$^{25}_D$=(−) 14° (c 1.0, CH$_2$Cl$_2$), t$_2$=14.8 min.

Cis-4-(3'-Chlorophenyl)-6-methoxy-7-chloro-N,N-dimethyl-1,2,3,4-tetrahydronaphthalen-2-amine (7g-h). 7g-h was prepared from 6b as a hygroscopic solid. Yield: 34%; $^1$H-NMR (400 MHz, CDCl$_3$): δ 7.31-7.05 (m, 5H), 6.26 (s, 1H), 4.15 (dd, J=12.0, 4.5 Hz, 1H, H-4), 3.76-3.63 (m, 1H), 3.62 (s, 3H), 3.17-2.99 (m, 2H), 2.85 (s, 6H), 2.54-2.50 (m, 1H), 1.89 (dd, J=24.0, 12.0 Hz, 1H). $^{13}$C NMR (100 MHz, CDCl$_3$): δ 28.7, 29.7, 34.4, 45.7, 56.1, 60.9, 112.4, 121.7, 125.0, 126.8, 127.7, 128.5, 130.3, 130.6, 134.8, 136.7, 146.0, 154.0. HRMS Calcd. for C$_{19}$H$_{22}$Cl$_2$NO: 350.1073, 352.1049 [M+H]$^+$; Found: 350.1073, 352.1047; isotope pattern confirmed. HPLC (s-prep); solv. sys=EtOH:Hexane (8:92)+0.1% of diethylamine (modifier)+0.1% trifluoroacetic acid (modifier); flow rate=4 mL/min. 7g. $[\alpha]^{25}_D=(+)$ 282° (c 1.0, CH$_2$Cl$_2$), ft=19.4 min. 7h. $[\alpha]^{25}_D=(-)$ 272° (c 1.0, CH$_2$Cl$_2$), t$_2$=12.7 min.

Trans-4-(3'-Bromophenyl)-6-methoxy-7-chloro-N,N-dimethyl-1,2,3,4-tetrahydronaphthalen-2-amine (7i-j). 7i-j was prepared from 4a as a hygroscopic solid. Yield: 33%; $^1$H-NMR (400 MHz, CDCl$_3$): δ 7.39 (t, J=7.4 Hz, 1H), 7.26 (d, J=4.7 Hz, 1H), 7.19 (t, J=7.4 Hz, 1H), 7.09 (s, 1H), 6.87 (d, J=7.9 Hz, 1H), 6.50 (s, 1H), 4.45-4.38 (bs, 1H, H-4), 3.78 (s, 3H), 3.29-3.23 (m, 2H), 3.09-3.02 (m, 3H), 2.76 (s, 6H), 2.38-2.34 (m, 2H). $^{13}$C NMR (100 MHz, CDCl$_3$): δ 29.1, 31.8, 42.3, 43.4, 56.2, 57.9, 112.8, 122.2, 123.1, 125.5, 126.9, 130.3, 130.8, 131.1, 134.3, 146.3, 154.2, 162.7. HRMS Calcd. for C$_{19}$H$_{22}$BrClNO: 394.0573, 396.0553 [M+H]$^+$, Found 394.0578, 396.0560; isotope pattern confirmed. HPLC (s-prep): solv. sys=EtOH:Hexane (8:92)+ 0.1% of diethylamine (modifier)+0.1% trifluoroacetic acid (modifier); flow rate=4 mL/min. 7i. $[\alpha]^{25}D=(+)$ 14° (c 1.0, CH$_2$Cl$_2$), t$_1$=13.1 min. 7j. $[\alpha]^{25}_D=(-)$ 14° (c 1.0, CH$_2$Cl$_2$). t$_2$=14.6 min.

Trans-4-(3'-Chlorophenyl)-6-methoxy-N,N-dimethyl-1,2,3,4-tetrahydronaphthalen-2-amine (7k-l). 7k-l Prepared from 4a as hygroscopic solids. Total yield: 38%. $^1$H-NMR (400 MHz, CDCl$_3$): δ 7.26 (d, J=1.6 Hz, 1H), 7.21-7.15 (m, 1H), 7.10 (d, J=8.4 Hz, 1H), 7.09 (s, 1H), 6.91 (dd, J=8.0, 2.0 Hz, 1H), 6.78 (dd, J=8.0, 2.4 Hz, 1H), 6.44 (d, J=2.0 Hz, 1H), 4.32 (t, J=4.8 Hz, 1H, H-4), 3.69 (s, 3H), 3.01 (dd, J=16.0, 5.0 Hz, 1H), 2.85-2.79 (m, 1H), 2.69, (m, 1H), 2.34 (s, 6H), 2.16-2.11 (m, 2H). $^{13}$C NMR (100 MHz, CDCl$_3$): δ 31.1, 34.4, 41.5, 44.0, 55.2, 56.6, 113.4, 114.3, 126.4, 126.8, 127.8, 128.7, 129.5, 130.3, 134.1, 137.7, 148.4, 157.9. HRMS m/z Calcd for C$_{19}$H$_{23}$ClNO 316.1468, 318.1439 [M+H]$^+$, Found 316.4163, 318.1440, isotope pattern confirmed. HPLC (s-prep): solv. sys=EtOH:Hexane (8:92)+ 0.1% of diethylamine (modifier)+0.1% trifluoroacetic acid (modifier); flow rate=4 mL/min. 7k. $[\alpha]^{25}_D=(+)$ 12° (c 1.0, CH$_2$Cl$_2$), t=12.7 min. 7l. $[\alpha]^{25}_0=(-)$ 10° (c 1.0, CH$_2$Cl$_2$). t=14.5 min.

Trans-4-Phenyl-6-hydroxy-7-chloro-N,N-dimethyl-1,2,3,4-tetrahydronaphthalen-2-amine (7m-n). The enantiomerically pure 7a or 7b (0.16 mmol) was dissolved in HBr solution (48% in water, 3 mL) and refluxed for 4 h. After cooling, the reaction mixture was quenched by saturated NaHCO$_3$ solution, extracted with CH$_2$Cl$_2$, and the organic layer was dried over anhydrous MgSO$_4$ and filtered. Solvent was removed under reduced pressure and the residue was purified by silica gel column chromatography (dichloromethane:methanol=95:5) to obtain the racemic 7m-n free base. MP: 155-158° C. $^1$H NMR (400 MHz, CD$_3$OD): δ 7.29 (t, J=7.2 Hz, 2H), 7.23-7.17 (m, 2H), 7.04 (d, J=7.2 Hz, 2H), 6.51 (s, 1H), 4.39 (t, J=4.4 Hz, 1H), 3.27-3.19 (m, 1H), 3.15 (dd, J=16.5, 5.0 Hz, 1H), 2.93 (dd, J=15.6, 10.4 Hz, 1H), 2.64 (s, 6H), 2.312.24 (m, 2H). $^{13}$C NMR (CD$_3$OD): δ 153.0, 146.6, 137.9, 131.3, 129.6, 129.5, 127.6, 127.2, 120.7, 118.3, 58.4, 44.7, 40.8, 34.1, 30.1. HRMS Calcd for C$_{18}$H$_{21}$ClNO: 302.1312, 302.1282 [M+H]$^+$; Found: 302.1311, 302.1372; isotope pattern confirmed. 7m: $[\alpha]^{25}_D=+31.6$ (c 1.2, MeOH). 7n: $[\alpha]^{25}_D=-30.0$ (c 1.2, MeOH). The 7n and 7m HCl salts for pharmacological studies were obtained by passing HCl gas through an ethereal solution of the free base.

4-PAT Biological Examples

Example 8: Binding Affinity of the Compounds

Radioreceptor competitive binding assays were carried out to assess the binding affinities of the compounds of the invention. Radioligand competitive displacement binding assays were performed in 96-well plates, using 3-5 μg of protein from membrane samples per well. Each concentration point in the binding experiments was performed in triplicates of samples, and each experiment was performed a minimum of three times. Final concentration of radioligands in the assay mixtures was ~K$_D$ concentration, i.e., 2.0 nM [$^3$H]ketanserin (5-HT$_{2A}$), 1.95 nM [$^3$H]mesulergine (5-HT$_{2B}$), 1.4 nM [$^3$H]mesulergine (5-HT$_{2C}$), or 1.0 nM [$^3$H]mepyramine (H1). Non-specific binding was determined in the presence of or 10 μM mianserin for all three 5-HT$_2$ receptors or 10 μM triprolidine for H1 receptors. Radioreceptor binding assay mixtures were incubated for 1.0 hour at 37° C., with termination by rapid filtration through Whatman GF/B filters using a 96-well cell harvester (Tomtec, Hamden, Conn.), which were subsequently washed five times with 50 mM Tris-HCl at room temperature. Filters containing bound [$^3$H]radioligand were dried, placed in vials containing 2 mL scintillation cocktail (ScintiVerse), allowed to equilibrate overnight, and then were counted for $^3$H-induced scintillation using a Beckman-Coulter LS6500 counter.

Functional responses of analog 7l and 5-HT (positive control agonist, data not shown) by measuring 5-HT$_2$ and H1 receptor-mediated inositol phosphate hydrolysis were assessed. In brief, transiently transfected HEK293 cells were labeled with 1 μCi/ml [3H]myoinositol and seeded into 48-well plates. Cells were treated with test compounds for 30 minutes. The reaction was stopped by addition of 50 mM formic acid. Anion-exchange columns (Bio-Rad Laboratories, Hercules, Calif.) were used to bind and collect [3H] inositol phosphates. 3H-induced scintillations then were measured. Each experiment included a minimum of triplicate measurements for each concentration of test compound, and each experiment was performed a minimum of three times.

Competition binding data were analyzed using nonlinear regression curve-fitting algorithms in GraphPad Prism, 6 for Windows (San Diego, Calif.). Hill slopes were not calculated as only eight data points were used to plot the graphs, thus, the algorithm for one-site fit Ki determination was used wherein the Hill slope was set to 1.0; only data from curve fits with $R^2$>0.9 were included in analyses. Ligand affinity was expressed as an approximation of K$_i$ values by conversion of the IC$_{50}$ value using the Cheng-Prusoff equation K$_i$=IC$_{50}$/I+L/K$_D$ where L was the concentration of radioligand.

Table 6 summarizes the results of the radioreceptor binding experiments. For analogs 7a-d, which have 6-methoxy and 7-chloro substitutions to the PAT tetrahydronaphthyl moiety, stereoselectivity for binding was (−)-trans>(+)-trans>(−)-cis>(+)-cis). Addition of the hydrogen and halogen binding moieties, 6-methoxy and 7-chloro, respectively, in analogs 7b-d contributed to enhanced binding interactions across 5-HT$_2$ receptors. 7a ([+]-trans enantiomer) showed relatively poor 5-HT$_{2A}$ affinity; the 6-methoxy moiety does not have the same hydrogen bonding potential as the 6-hydroxy moiety of 7m ([+]-trans enantiomer) for strong interaction with 5-HT$_{2A}$ residue S5.46.

TABLE 6

| Comp. | Config. | $R_6$ | $R_7$ | $R_3'$ | Affinity ($K_i \pm$ SEM; nM) 5-HT$_{2A}$ | 5-HT$_{2B}$ | 5-HT$_{2C}$ | H$_1$ |
|---|---|---|---|---|---|---|---|---|
| 7a | (+)-trans | OCH$_3$ | Cl | H | 240 ± 23 | 57.7 ± 11.8 | 37 ± 5.1 | 120 ± 20 |
| 7b | (−)-trans | OCH$_3$ | Cl | H | 160 ± 24 | 17.3 ± 5.33 | 24 ± 2.5 | 1.2 ± 0.6 |
| 7c | (+)-cis | OCH$_3$ | Cl | H | 2,300 ± 130 | 2,500 ± 150 | 1,600 ± 60 | >1000 |
| 7d | (−)-cis | OCH$_3$ | Cl | H | 320 ± 42 | 43 ± 5 | 96 ± 18 | 10.8 ± 0.60 |
| 7e | (+)-trans | OCH$_3$ | Cl | Cl | 95 ± 18 | 136 ± 20 | 7.0 ± 3.0 | 120 ± 17 |
| 7f | (−)-trans | OCH$_3$ | Cl | Cl | 50 ± 20 | 56 ± 4.0 | 9.0 ± 2.0 | 18.9 ± 0.70 |
| 7g[a] | (+)-cis | OCH$_3$ | Cl | Cl | n.d. | n.d. | n.d. | n.d. |
| 7h[a] | (−)-cis | OCH$_3$ | Cl | Cl | n.d. | n.d. | n.d. | n.d. |
| 7i | (+)-trans | OCH$_3$ | Cl | Br | 79 ± 14 | 169 ± 27 | 350 ± 130 | 650 ± 21 |
| 7j | (−)-trans | OCH$_3$ | Cl | Br | 61 ± 15 | 50 ± 3.0 | 130 ± 43 | 230 ± 33 |
| 7k | (+)-trans | OCH$_3$ | H | Cl | 350 ± 16 | 310 ± 41 | 280 ± 30 | 740 ± 80 |
| 7l | (−)-trans | OCH$_3$ | H | Cl | 35 ± 3.0 | 65 ± 9.0 | 17 ± 1.0 | 86 ± 18 |
| 7m* | (+)-trans | OH | Cl | H | 70 ± 2.6 | 1,200 ± 25 | 1,000 ± 80 | 109 ± 17 |
| 7n* | (−)-trans | OH | Cl | H | 60 ± 5.4 | 91 ± 5.3 | 23 ± 3.0 | 3.0 ± 1.0 |

Regarding H1 receptor affinity, the (+)-cis isomer 7c had about 10-fold lower affinity than the corresponding a related compound (+)-cis-PAT 1c analog (with reference to Formula II, (+)-cis confirmation and each of $R_6$, $R_7$, and $R_3'$ being hydrogen), which was determined to have the (2R, 4R) absolute configuration. Taken together, and without wishing to be bound by theory, the affinity results for 7a-d suggest binding at both 5-HT$_2$ and H$_1$ receptor pockets, and that the higher affinity observed for the (−)-trans-7b analog in comparison to the (−)-trans-1b analog (with reference to Formula II, each of $R_6$, $R_7$, and $R_3'$ being hydrogen) likely can be attributed to the presence of the 6-OCH$_3$ and 7-Cl moieties that result in additional hydrogen and halogen binding interactions with binding pocket amino acids.

The analogs 7e-h retain the 6-OCH$_3$ and 7-Cl moieties present in 7a-d and also include an additional Cl moiety at the 3' (meta) position of the C(4)-phenyl moiety. Stereochemical preference for binding of the (−)-trans enantiomer (7f) over the (+)-trans- enantiomer (7e) was maintained across receptors similar to the 1a-b and 7a-b analogs, except, at the 5-HT$_{2C}$ receptor where the (+)-enantiomer 7e had unusually high affinity—this was not the case when the 3'-position was substituted with bromine as in analogs 7i-j. Substituting 3'-Br rather than 3'-Cl compromised affinity at both 5-HT$_{2C}$ and H1 receptors. The cis-analogs 7c-d had significantly less affinity across receptors compared to the corresponding trans-analogs 7a-b.

In comparison to the analogs 7a-b, affinity of corresponding trans analogs 7e-f and 7i-j was reduced at histamine H1 receptors. In comparison to the corresponding (−)-trans-analog 7f that includes the 7-Cl moiety, removing the 7-Cl moiety, as in the (−)-trans enantiomer 7l, resulted in an even greater reduction in affinity at H1 receptors, without changing affinities at 5-HT$_2$ receptors; the affinity of the (+)-trans enantiomer 7k was diminished at all receptors.

Figure 13:
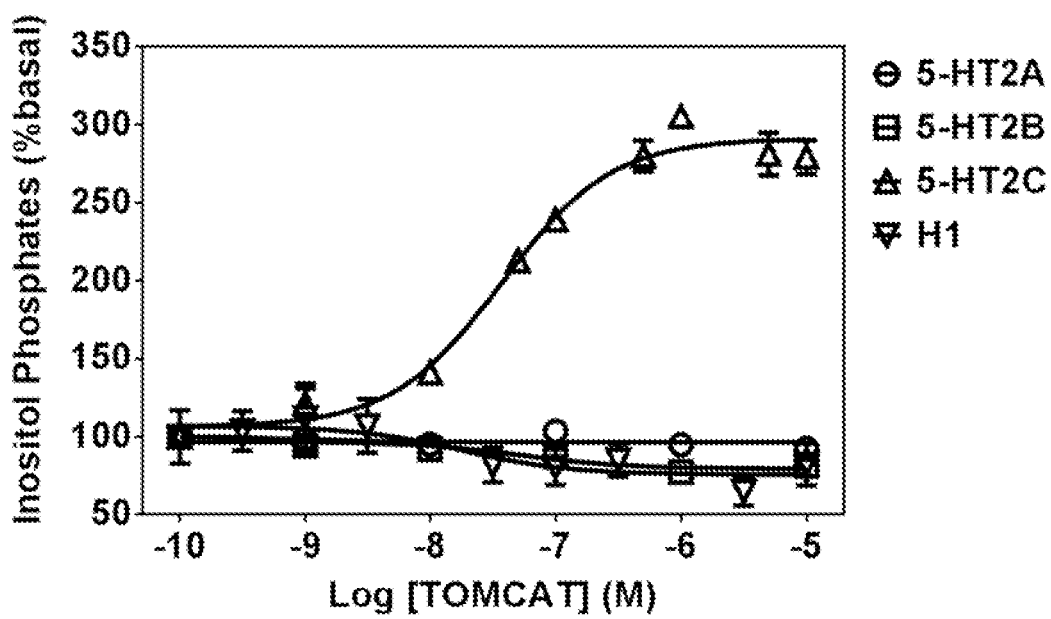
FIG. 13 shows the binding affinity of compound 71 (on X axis called "TOMCAT" i.e., trans-4-(3'-chlorophenyl)-6-methoxy-N,N-dimethyl-1,2,3,4-tetrahydronaphthalen-2-amine), a 4-PAT series compound, at 5-HT$_{2A}$, 5-HT$_{2B}$, and 5-HT$_{2C}$ receptors Also included is affinity at histamine H1 receptor.

Functional assays for compound 7l were carried out based on the observation that compound 7l has high affinity at 5-HT$_2$ receptors with selectivity over H1. As shown in FIG. 13 and Table 7, compound 7l activated exclusively 5-HT$_{2C}$ receptors. The agonist potency of 7l (EC$_{50}$=19±1 nM) was the same as 1b (20±2 nM). 7l did not activate human 5-HT$_{2A}$ receptors at concentrations up to 10 µM (FIG. 13). At 5-HT$_{2B}$ and H1 receptors compound 7l was an inverse agonist with a mean (±S.E.M.) IC50 value of 51 (6.1) and 48 (4.5) nM, respectively.

TABLE 7

| Compound | In vitro pharmacology | 5-HT$_{2A}$ | 5-HT$_{2B}$ | 5-HT$_{2C}$ | H$_1$ |
|---|---|---|---|---|---|
| 7l | Function (nM) | No activation | IC$_{50}$ = 51 ± 6.1 | EC50 = 19 ± 1 | IC$_{50}$ = 48 ± 4.5 |
|  | Efficacy (%) | N/A | $I_{max}$ = −17 ± 4.6 | EMAX = 73 ± 6 | $I_{max}$ = −25 ± 1.5 |

These results indicate that the combination of 6-OCH$_3$ and 7-Cl substitutions to the tetrahydronaphthyl moiety of (−)-trans-PAT had only modest effects on 5-HT$_2$ and H1 binding affinity, relative to unsubstituted PAT (e.g., 1 b and 7b, Table 5), but, when a chloro- group also was substituted at the 3'(meta)-position of the C(4) phenyl moiety, affinity across 5-HT$_2$ receptors was significantly enhanced while H1 affinity was significantly reduced (7f, Table 6). Thus, it is clearly achievable to reduce or eliminate H1 receptor-mediated activity that has been associated with the weight-gain effects among antipsychotic drugs that target 5-HT$_{2A}$ receptors as part of their mechanism of action. Meanwhile, analog 7l, that does not include the 7-Cl moiety but is otherwise the same as 7f, has even lower H1 affinity than 7f while maintaining robust 5-HT$_2$ receptor affinity. Differences in binding pocket steric accommodation was revealed by the corresponding 3'(mefa)-bromo analog 7j that, in comparison to 7f, maintained affinity at 5-HT$_{2A}$ and 5-HT$_{2B}$ receptors, but compromised affinity at 5-HT$_{2C}$ and H1 receptors (Table 6).

The new PAT-type compound, 7l enhanced affinity at 5-HT$_2$ receptors, but >40-fold reduced affinity at H1 receptors compared to unsubstituted PAT (7b). Furthermore, 7l exclusively activated 5-HT$_{2C}$ receptors. It showed inverse agonism at human 5-HT$_{2B}$ and histamine H1 signaling and did not activate 5-HT$_{2A}$ receptors, even at 10 µM. It is noteworthy that 7l as an inverse agonist at human 5-HT$_{2B}$ receptors would eliminate the possibility of 5-HT$_{2B}$-mediated cardiac valvulopathy, and may enhance cognition. Additionally, as 7l does not activate 5-HT$_{2A}$ receptors, concern of hallucinogenic effects is assuaged. This pharmacological profile of 7l sets it apart from all other reported, non-PAT-like, selective 5-HT$_{2C}$ agonists i.e. lorcaserin, Ro60-0175, mCPP etc, all of which also activate 5-HT$_{2A}$ and 5-HT$_{2B}$ receptors.

Example 9: In Vivo Efficacy of the Compounds in Treating Neuropsychiatric Disorder In vivo studies of the compounds of Formula II and Formula IIa are carried out in mice by examining for a reversal of MK-801-induced increase in behavioral activity. Additional studies to examine the effectiveness of these compounds in reversing the disruption in attention and working memory and increases in impulsivity produced by MK-801 are also conducted.

Administration of the glutamatergic N-methyl-D-aspartate (NMDA) antagonist MK-801 to mice is known to induce attention deficits, impulsive action, and disrupt working memory. C57Bl/6J mice are treated with MK-801. A subgroup of the mice is pre-treated with compounds of Formula II and Formula IIa. Control mice are pre-treated with saline. These studies indicate that mice pre-treated with the compounds of the invention attenuated MK-801 induced hyperactivity.

Specifically, an "observing-response" procedure is established in which attention is directly measured as an operant response. Mice obtain reinforcers by responding to one lever under mixed-schedule conditions (stimulus conditions do not indicate whether food is available or not). By making an "observing response" on a second lever, stimulus conditions change to multiple schedule where the availability of food is signaled. This procedure allows the animal to make responses so that it can come into contact with the relevant behavioral contingencies and respond more effectively (which is a definition of attending or paying attention). Under these conditions, administration of the compounds of Formula II and Formula IIa selectively increases observing without dramatically altering response rates under other conditions (e.g., no alteration in response rate for food during the multiple schedule). This selective increase in paying attention further indicates that the observing response procedure is sensitive to the attention enhancing effects of the compounds of the invention.

The effects of the compounds on impulsivity are assessed by a visual discrimination procedure. Mice are trained to respond to one of two levers, with the correct lever being signaled by a 1-second light flash over the lever. Stimulus presentations occur on average every 5 seconds. Responses that occur before presentation of the light flash are considered impulsive responses and result in a 5-second timeout. Mice treated with MK-801 exhibits an increase in impulsivity, while pre-treatment with compounds of Formula II and Formula IIa reverses this increase in impulsivity.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A pharmaceutical composition, comprising a therapeutically effective amount of an at least about 90% pure (S)-enantiomer dual partial agonist at the serotonin 5-HT$_7$ and 5-HT$_{1A}$ receptors, the dual partial agonist having the structure of Formula (I):

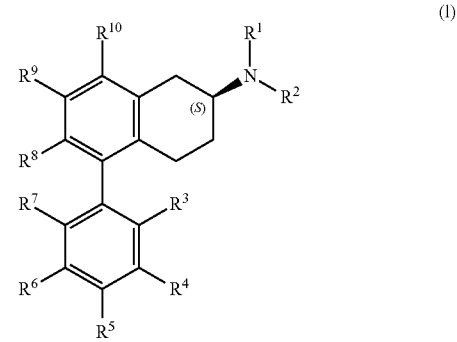

or a pharmaceutically acceptable salt, hydrate, or solvate thereof, wherein:
each of $R^1$ and $R^2$ is independently hydrogen or alkyl;
$R^3$ and $R^7$ are each independently hydrogen, chloro, fluoro, or amino;
$R^5$ is hydrogen or fluoro;
each of $R^4$ and $R^6$ is independently hydrogen, chloro, fluoro, alkoxy, or trifluoromethyl;
each of $R^8$, $R^9$, and $R^{10}$ is independently hydrogen or alkoxy, but if $R^{10}$ is alkoxy at least one of $R^8$ and $R^9$ is also alkoxy;
such that at least one of $R^3$, $R^4$, $R^5$, $R^6$, $R^7$, and $R^8$ is not hydrogen, or wherein $R^4$ and $R^5$ and $R^6$ and $R^7$ are joined to form an unsubstituted anthracene ring;
and a pharmaceutically acceptable excipient or carrier.

2. The pharmaceutical composition of claim 1, wherein the dual partial agonist binds to serotonin 5-HT$_7$ receptor and/or the 5-HT$_{1A}$ receptor with a binding affinity ($K_i$) of less than about 100 nM, or less than about 50 nM, or less than about 25 nM, or less than about 20 nM, or less than about 10 nM, or less than about 5 nM, or less than about 2 nM, or less than about 1 nM.

3. The pharmaceutical composition of claim 1, wherein the dual partial agonist does not bind one or more of the serotonin 5-HT$_{2A}$ and 5-HT$_{2C}$ receptors at physiologically-relevant levels.

4. The pharmaceutical composition of claim 1, wherein the dual partial agonist binds one or more of the serotonin 5-HT$_7$ and 5-HT$_{1A}$ receptors with at least about 10-fold, or at least about 20-fold, or at least about 30-fold, or at least about 40-fold, or at least about 50-fold, or at least about 75-fold, or at least about 100-fold higher affinity than one or more of the serotonin 5-HT$_{2A}$ and 5-HT$_{2C}$ receptors.

5. The pharmaceutical composition of claim 1, wherein the dual partial agonist binds one or more of the serotonin 5-HT$_7$ and 5-HT$_{1A}$ receptors with an at least about 10-fold, or at least about 20-fold, or at least about 30-fold, or at least about 40-fold, or at least about 50-fold, or at least about 75-fold, or at least about 100-fold higher affinity than a corresponding enantiomer.

6. The pharmaceutical composition of claim 1, wherein the dual partial agonist does not bind one or more of the histamine H1 receptor, dopamine D2, and adrenergic α$_{1A}$ and α$_{1B}$ receptors at physiologically-relevant levels.

7. The pharmaceutical composition of claim 1, wherein at least one of R$^3$, R$^4$, R$^5$, R$^6$, and R$^7$ is fluoro.

8. The pharmaceutical composition of claim 1, wherein only R$^3$ is a substituent other than H.

9. The pharmaceutical composition of claim 8, wherein R$^3$ is chloro or fluoro.

10. The pharmaceutical composition of claim 1, wherein at least one of R$^8$, R$^9$, and R$^{10}$ is methoxy.

11. The pharmaceutical composition of claim 1, wherein the dual partial agonist is:

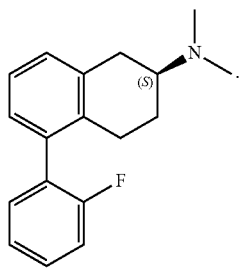

12. A compound having the structure of one of:

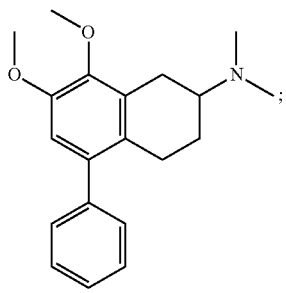

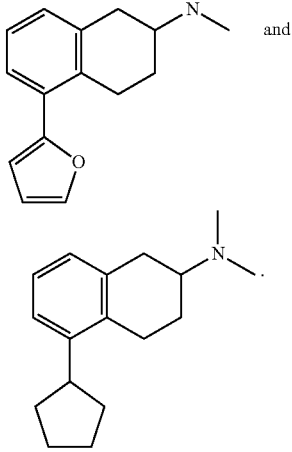

13. A method of treating or preventing a neuropsychiatric disease or disorder, comprising administering an effective amount of a composition of claim 1 to a patient in need thereof.

14. The method of claim 13, wherein the neuropsychiatric disease or disorder is one or more of autism, anxiety, depression, obsessive-compulsive disorders, schizophrenia, suicide, migraine, emesis, alcoholism and neurodegenerative disorders.

15. The method of claim 13, wherein the neuropsychiatric disease or disorder is selected from autism spectrum disorder (ASD); Asperger syndrome, Fragile X syndrome (FXS), Prader-Willi syndrome, Rett syndrome, Tourette syndrome, attention-deficit hyperactivity disorder (ADHD), obsessive-compulsive disorder, psychotic disorders, psychostimulant addiction and generalized anxiety.

16. The method of claim 13, wherein the treatment comprises a reduction in the frequency of one or more of stereotypy, self-injurious behaviors, compulsions, and tics.

17. A method of treating autism spectrum disorder (ASD), comprising administering an effective amount of a composition of claim 1 to a patient in need thereof.

18. A method of treating stereotypy, comprising administering an effective amount of a composition of claim 1 to a patient in need thereof.

19. A method of selectively modulating serotonin 5-HT$_7$ and 5-HT$_{1A}$ receptors, comprising contacting a cell with a composition of claim 1, wherein the modulation is partial antagonism.

* * * * *